(12) United States Patent
Alestra et al.

(10) Patent No.: US 11,654,869 B2
(45) Date of Patent: May 23, 2023

(54) REMOTE USER INTERFACE COMMANDED VEHICLE INTERIOR SANITIZATION

(71) Applicant: Ford Global Technologies, LLC, Dearborn, MI (US)

(72) Inventors: Maxwell Alestra, Livonia, MI (US); Ghanshyam M. Patel, Canton, MI (US); Troy Fischer, Novi, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 206 days.

(21) Appl. No.: 17/079,792

(22) Filed: Oct. 26, 2020

(65) Prior Publication Data

US 2022/0126793 A1 Apr. 28, 2022

(51) Int. Cl.
*B60S 1/64* (2006.01)
*B60K 15/03* (2006.01)
(Continued)

(52) U.S. Cl.
CPC . *B60S 1/64* (2013.01); *A61L 2/10* (2013.01); *A61L 2/26* (2013.01); *B60K 6/24* (2013.01); *B60K 6/26* (2013.01); *B60K 6/28* (2013.01); *B60K 15/03* (2013.01); *B60L 1/14* (2013.01); *B60L 58/12* (2019.02); *F01P 3/20* (2013.01); *F02D 41/062* (2013.01); *G05D 1/0016* (2013.01); *A61L 2202/11* (2013.01); *A61L 2202/14* (2013.01); *A61L 2202/25* (2013.01); *B60K 2015/0321* (2013.01); *F01P 2060/18* (2013.01)

(58) Field of Classification Search
CPC ..... B60Q 3/68; A61L 2/04; A61L 2/08; A61L 2/10; A61L 9/20; A61L 9/205; B60S 1/64; B60L 58/12–14; B60L 1/14; F02D 41/062–065
See application file for complete search history.

(56) References Cited

U.S. PATENT DOCUMENTS 8,689,617 B2 4/2014 Rollinger et al.
9,855,353 B1 * 1/2018 Stacy .................. A61L 2/10
(Continued)

FOREIGN PATENT DOCUMENTS

CN 113581133 * 11/2021
DE 102018002328 A1 9/2019
(Continued)

Primary Examiner — Syed O Hasan
(74) Attorney, Agent, or Firm — Vichit Chea; Price Heneveld LLP

(57) ABSTRACT

A vehicle comprising an interior; a heat source in thermal communication with the interior; a source of ultraviolet light disposed to emit the ultraviolet light into the interior; and a controller in communication with the heat source and the source of the ultraviolet light, the controller configured to cause (i) the heat source to increase a temperature of the interior, (ii) the source of the ultraviolet light to emit the ultraviolet light into the interior, or (iii) both (i) and (ii) upon receiving a command from a remote user interface. The vehicle can further include a combustion engine that combusts fuel to propel the vehicle. The vehicle can further include a battery in electrical communication with the source of the ultraviolet light and in communication with the controller, the battery having a voltage.

16 Claims, 31 Drawing Sheets

(51) Int. Cl.
   *F01P 3/20*    (2006.01)
   *B60L 1/14*    (2006.01)
   *B60L 58/12*   (2019.01)
   *B60K 6/24*    (2007.10)
   *B60K 6/26*    (2007.10)
   *B60K 6/28*    (2007.10)
   *G05D 1/00*    (2006.01)
   *A61L 2/26*    (2006.01)
   *A61L 2/10*    (2006.01)
   *F02D 41/06*   (2006.01)

(56) References Cited

U.S. PATENT DOCUMENTS

| | | |
|---|---|---|
| 10,576,825 B1 | 3/2020 | Salter et al. |
| 2004/0084232 A1* | 5/2004 | Obayashi .............. H02J 7/1423 180/65.28 |
| 2015/0273092 A1* | 10/2015 | Holub .................... B60Q 3/68 250/492.1 |
| 2016/0303992 A1 | 10/2016 | Lovett et al. |
| 2019/0076558 A1* | 3/2019 | Zhang-Miske ...... B60Q 11/005 |
| 2020/0148149 A1 | 5/2020 | Deng et al. |
| 2020/0254931 A1 | 8/2020 | Herman |
| 2020/0265654 A1 | 8/2020 | Kapadia et al. |
| 2020/0271046 A1 | 8/2020 | Kelly et al. |
| 2021/0245756 A1* | 8/2021 | Martin .................. F02D 41/123 |
| 2022/0031880 A1* | 2/2022 | Hwang .................... A61L 2/10 |

FOREIGN PATENT DOCUMENTS

| | | | |
|---|---|---|---|
| KR | 200418459 | * | 3/2006 |
| KR | 200418459 Y1 | * | 3/2006 |
| KR | 20150017544 | * | 2/2015 |
| KR | 20150017544 A | * | 2/2015 |

* cited by examiner

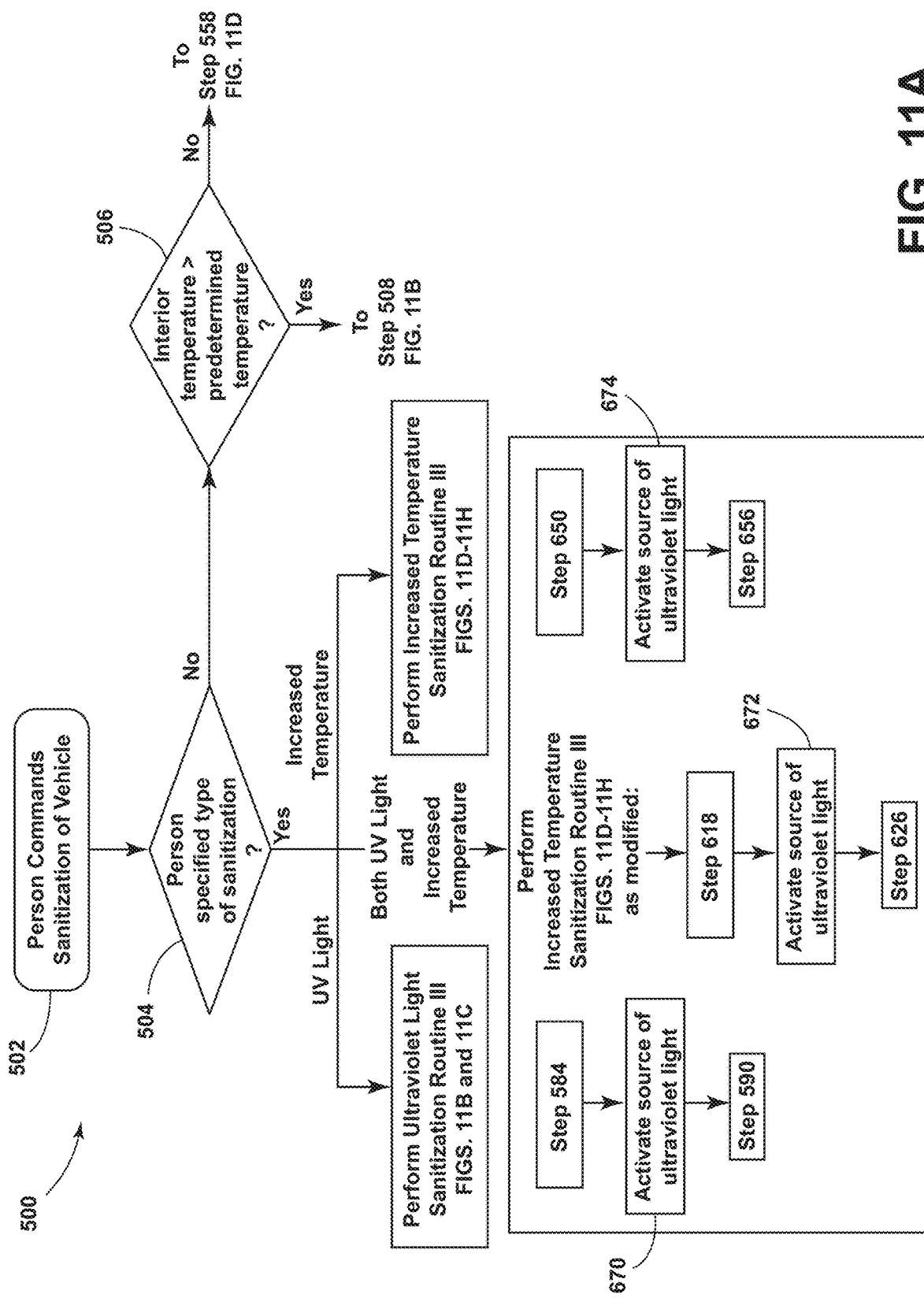

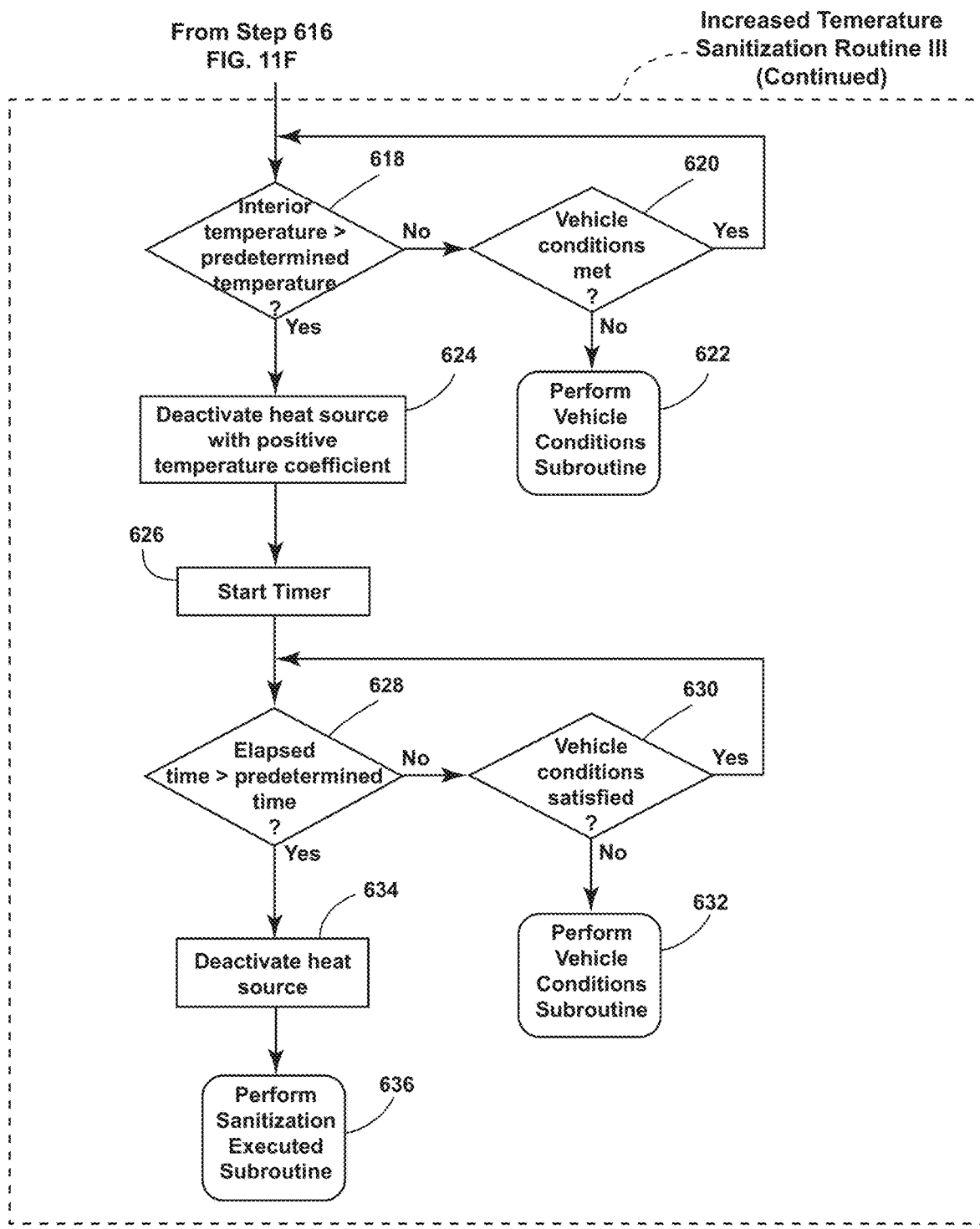

REMOTE USER INTERFACE COMMANDED VEHICLE INTERIOR SANITIZATION

FIELD OF THE DISCLOSURE

The present disclosure relates to sanitization of an interior of a vehicle and, more specifically, the vehicle executing sanitization of the interior pursuant to a command issued from a remote user interface.

BACKGROUND OF THE DISCLOSURE

There is a general desire to reduce the presence of microbes in an interior of a vehicle, and to provide feedback to a person of the vehicle that the interior has been sanitized.

SUMMARY OF THE DISCLOSURE

The present disclosure addresses that general desire with a vehicle that includes a heat source to heat an interior of the vehicle and an ultraviolet light source to emit ultraviolet light into the vehicle, and a controller configured to cause the heat source to heat and/or the ultraviolet light source to emit ultraviolet light into the interior (to sanitize the interior) upon a command from the person via a remote user interface.

According to a first aspect of the present disclosure, a vehicle comprises: an interior; a heat source in thermal communication with the interior; a source of ultraviolet light disposed to emit the ultraviolet light into the interior; and a controller in communication with the heat source and the source of the ultraviolet light, the controller configured to cause (i) the heat source to increase a temperature of the interior, (ii) the source of the ultraviolet light to emit the ultraviolet light into the interior, or (iii) both (i) and (ii) upon receiving a command from a remote user interface.

Embodiments of the first aspect of the present disclosure can include any one or a combination of the following features:
- the vehicle further comprises a combustion engine that combusts fuel to propel the vehicle;
- the vehicle does not further include an electric motor configured to propel the vehicle;
- the vehicle further comprises a battery in electrical communication with the source of the ultraviolet light and in communication with the controller, the battery having a voltage;
- upon receiving the command from the remote user interface to cause the source of the ultraviolet light to emit the ultraviolet light into the interior, and the voltage of the battery is below a predetermined voltage, the controller is further configured to start the combustion engine to increase the voltage of the battery to the predetermined voltage before causing the source of the ultraviolet light to emit the ultraviolet light into the interior;
- the vehicle further comprises: a fuel tank that contains the fuel, the fuel tank in fluid communication with the combustion engine; and a volume sensor configured to produce a signal from which a volume of the fuel within the fuel tank can be calculated or estimated, the volume sensor in communication with the controller;
- the controller, as a function of the signal from the volume sensor, determines that the volume of fuel is above a predetermined volume before starting the combustion engine to increase the voltage of the battery;
- the vehicle further comprises: a fuel tank that contains the fuel, the fuel tank in fluid communication with the combustion engine; a volume sensor configured to produce a signal from which an amount of the fuel can be calculated or estimated, the volume sensor in communication with the controller; and a heat exchanger in thermal communication with the combustion engine and the interior of the vehicle;
- the heat exchanger is the heat source;
- the controller, as a function of the signal from the volume sensor, determines that the volume of fuel is above a predetermined volume before starting the combustion engine to increase the temperature of the interior via the heat exchanger;
- the controller, as a function of the signal from the volume sensor, determines that the volume of the fuel is above a second predetermined volume before starting the combustion engine to increase the temperature of the interior;
- the second predetermined volume is greater than the predetermined volume;
- the vehicle further comprises a temperature sensor configured to produce a signal from which the temperature of the interior of the vehicle can be determined, the temperature sensor in communication with the controller;
- the controller, as a function of the signal from the temperature sensor determines that the temperature of the interior of the vehicle is less than a predetermined temperature before starting the combustion engine to increase the temperature of the interior;
- the vehicle further comprises an electric motor configured to propel the vehicle;
- the vehicle does not further include a combustion engine configured to propel the vehicle;
- the vehicle further comprises a battery in electrical communication with the source of the ultraviolet light and in communication with the controller, the battery having a voltage;
- upon receiving the command from the remote user interface to cause the source of the ultraviolet light to emit the ultraviolet light into the interior, the controller determines that the voltage of the battery is above a predetermined voltage before causing the source of the ultraviolet light to emit the ultraviolet light into the interior;
- the vehicle further comprises a second battery in electrical communication with the source of the ultraviolet light and in communication with the controller, the second battery having a state-of-charge;
- upon receiving the command from the user interface to cause the source of the ultraviolet light to emit the ultraviolet light into the interior, the controller determines that the state-of-charge of the second battery is above a predetermined state-of-charge before causing the source of the ultraviolet light to emit the ultraviolet light into the interior;
- the second battery is connected to an external power source that is external to the vehicle;
- upon receiving the command from the user interface to cause the source of the ultraviolet light to emit the ultraviolet light into the interior, the controller determines that the state-of-charge of the second battery is below a predetermined state-of-charge but additionally determines that the second battery is connected to the external power source before causing the source of the ultraviolet light to emit the ultraviolet light into the interior;

upon receiving the command from the user interface to cause the heat source to increase the temperature of the interior, the controller determines (i) that the state-of-charge of the battery is less than the predetermined state-of-charge and (ii) that the second battery is connected to the external power source causing the heat source to increase the temperature of the interior of the vehicle;

the heat source has a positive temperature coefficient;

the vehicle further comprises: a combustion engine configured to propel the vehicle; and an electric motor configured to propel the vehicle;

after the controller causes (i) the heat source to increase the temperature of the interior, (ii) the source of the ultraviolet light to emit the ultraviolet light into the interior, or (iii) both (i) and (ii), the controller causes a communication to the remote user interface that the command has been executed;

after the controller causes (i) the heat source to increase the temperature of the interior, (ii) the source of the ultraviolet light to emit the ultraviolet light into the interior, or (iii) both (i) and (ii), the controller causes the vehicle to send a communication that is sensible from an external environment that the command has been executed;

the vehicle further comprises an occupancy sensor configured to produce a signal from which an occupancy of the vehicle can be determined, the occupancy sensor in communication with the controller; and the controller, as a function of the signal from the occupancy sensor, determines that no occupant occupies the interior of the vehicle before causing the source of the ultraviolet light to emit the ultraviolet light into the interior.

According to a second aspect of the present disclosure, a method of sanitizing an interior of a vehicle comprises: receiving a command from a remote user interface to sanitize an interior of a vehicle; determining that a battery of the vehicle has a voltage that is greater than a predetermined voltage; and after so determining, sanitizing the interior of the vehicle by emitting ultraviolet light into the interior of the vehicle.

Embodiments of the second aspect of the present disclosure can include the following feature:

the method further comprises determining that the voltage of the battery of the vehicle is less than the predetermined voltage; and increasing the voltage of the battery.

These and other aspects, objects, and features of the present disclosure will be understood and appreciated by those skilled in the art upon studying the following specification, claims, and appended drawings.

BRIEF DESCRIPTION OF THE DRAWINGS

In the drawings:

FIGS. 11A-11H are schematic views of another method of sanitizing the interior of the vehicle of FIG. 1 using the remote user interface, when the propulsion system of the vehicle includes both the combustion engine and the electric motor as in FIG. 3C.

DETAILED DESCRIPTION OF THE PREFERRED EMBODIMENTS

Figure 1:
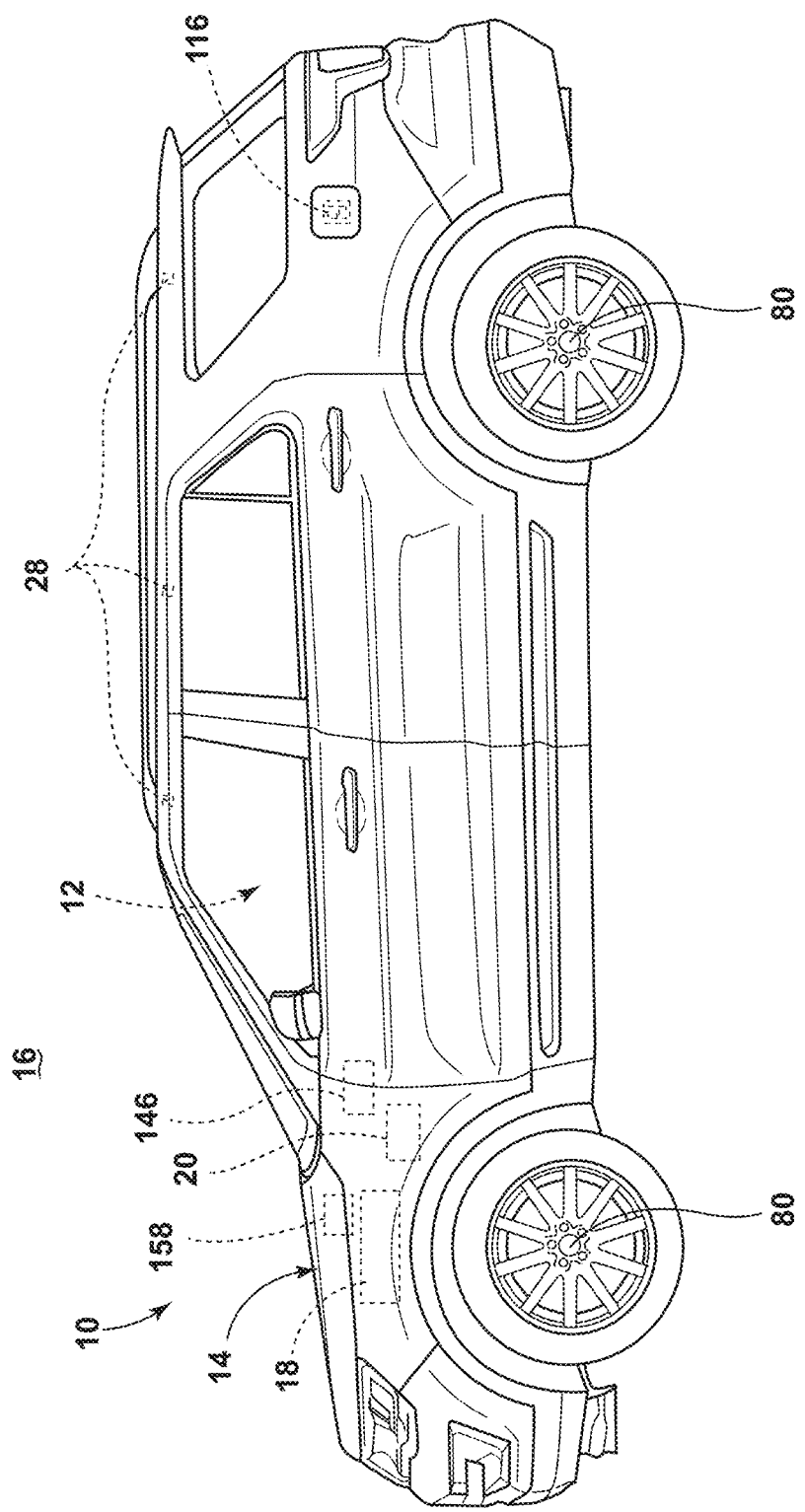
FIG. 1 is a side view of a vehicle, illustrating a heat source to heat the interior, a propulsion system to propel the vehicle, and controller in communication with the heat source.
Figure 2:
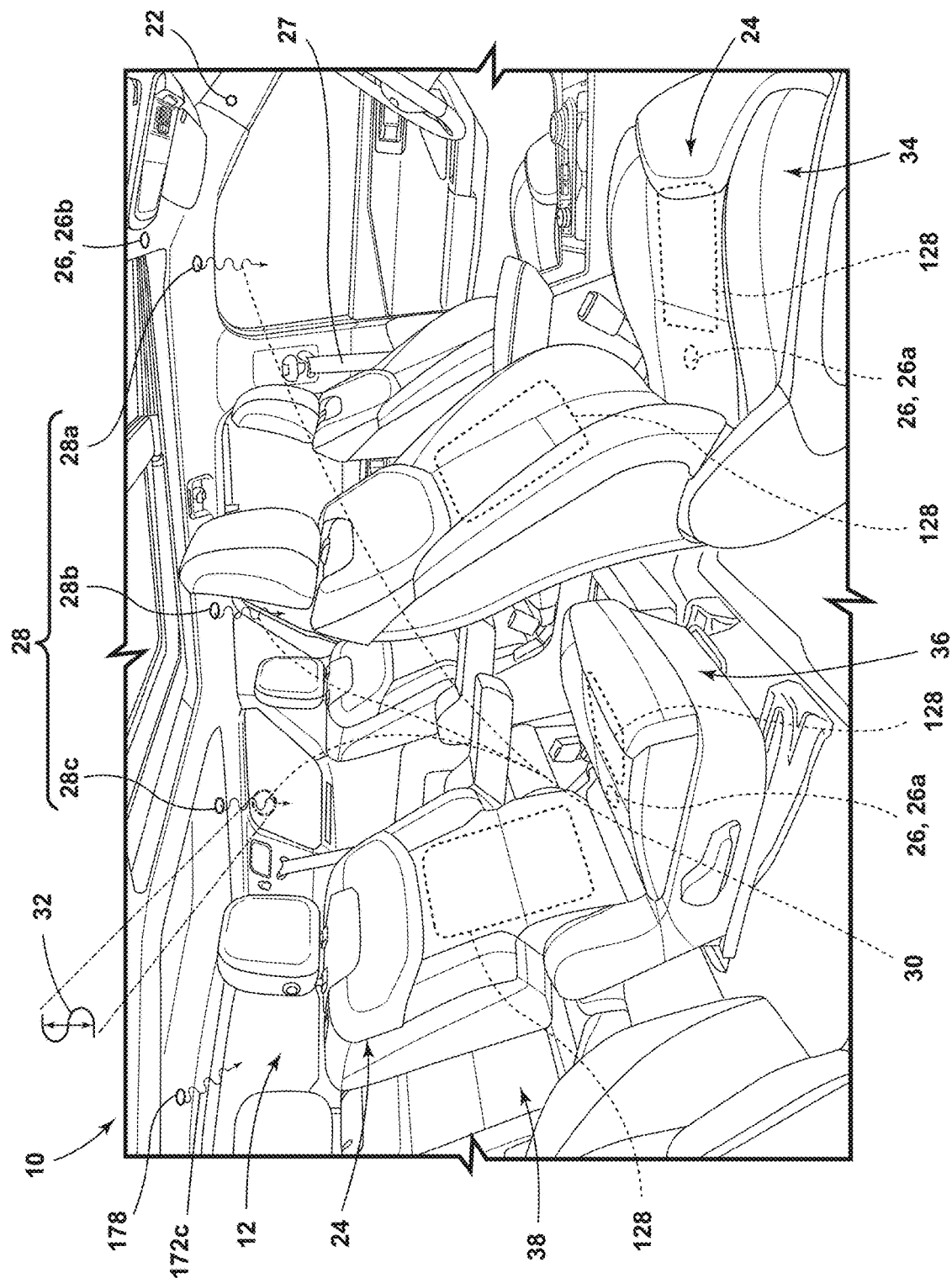
FIG. 2 is a perspective view of the interior of the vehicle of FIG. 1, illustrating the vehicle further including sources of ultraviolet light emitting ultraviolet light into the interior to sanitize the interior.

Referring now to FIGS. 1 and 2, a vehicle 10 includes an interior 12 and a body 14 that separates the interior 12 from an external environment 16. The vehicle 10 includes a propulsion system 18. The vehicle 10 further includes a heat source 20 that is in thermal communication with the interior 12. In other words, the heat source 20, when activated, increases a temperature of the interior 12 of vehicle 10. The vehicle 10 further includes a temperature sensor 22. The temperature sensor 22 outputs a signal from which the temperature of the interior 12 of the vehicle 10 (e.g., air temperature) can be determined. The vehicle 10 further includes seating assemblies 24 disposed within the interior 12. The vehicle 10 can be a car, a truck, a van, a sports utility vehicle 10, and the like. The vehicle 10 may be non-autonomous, semi-autonomous (e.g., some routine motive functions controlled by the vehicle 10), or autonomous (e.g., motive functions are controlled by the vehicle 10 without direct driver input).

In embodiments, the vehicle 10 further includes an occupancy sensor 26. The occupancy sensor 26 generates an output signal that varies as a function of whether any person is within the interior 12 of the vehicle 10. In embodiments, the occupancy sensor 26 includes a force sensor 26a (e.g., load cell, strain gauge, etc.) located in each of the seating assemblies 24 of the vehicle 10. In other embodiments, the occupancy sensor 26 includes a proximity sensor located in each of the seating assemblies 24. The proximity sensor outputs either a signal (e.g., a binary "1", a source voltage (5 V, 12 V, etc.), etc.) denoting that the seating assembly 24 is occupied by a person or a signal (e.g., a binary "0", a ground voltage (e.g., 0 V), etc.) indicating that the seating assembly 24 is not occupied by a person. In other embodiments, the occupancy sensor 26 includes a camera 26b that can sense visible or infrared electromagnetic radiation and that produces output data from which a signature of an occupant can be deciphered. In other embodiments, the occupancy sensor 26 includes a sensor that detects whether a seat strap 27 for any of the seating assemblies 24 is fastened or unfastened. The occupancy sensor 26 can be any combination of those particular sensors mentioned.

The vehicle 10 further includes a source 28 of ultraviolet light 30. The source 28 is disposed to emit the ultraviolet light 30 into the interior 12. "Ultraviolet light" means electromagnetic radiation having a wavelength 32 of 10 nm to 400 nm, including 100 nm to 280 nm and 260 nm to 280 nm, which is generally referred to as "Ultraviolet C" or "UVC" and has germicidal effects. Without being bound by theory, it is believed that the ultraviolet light 30 with the wavelength 32 of 100 nm to 280 nm damages RNA and DNA of a microorganism, which prevents the microorganism from replicating. The source 28 can be a lamp (e.g, a mercury vapor lamp), a light emitting diode, among possibly other options. In embodiments, the source 28 is a light emitting diode with the wavelength 32 of peak intensity of 260 nm to 280 nm. In embodiments, the source 28 can include the source 28a that is positioned to direct the ultraviolet light 30 to a first zone 34 within the interior 12, the source 28b that is positioned to direct the ultraviolet light to a second zone 36 within the interior, and the source 28c that is positioned to direct the ultraviolet light 30 to a third zone 38 within the interior 12. In embodiments, the first zone 34 is forward of the second zone 36, and the second zone 36 is forward of the third zone 38. In embodiments, only the source 28a for the first zone 34, and the source 28b for the second zone 36 are included with the vehicle 10.

Figure 3A:
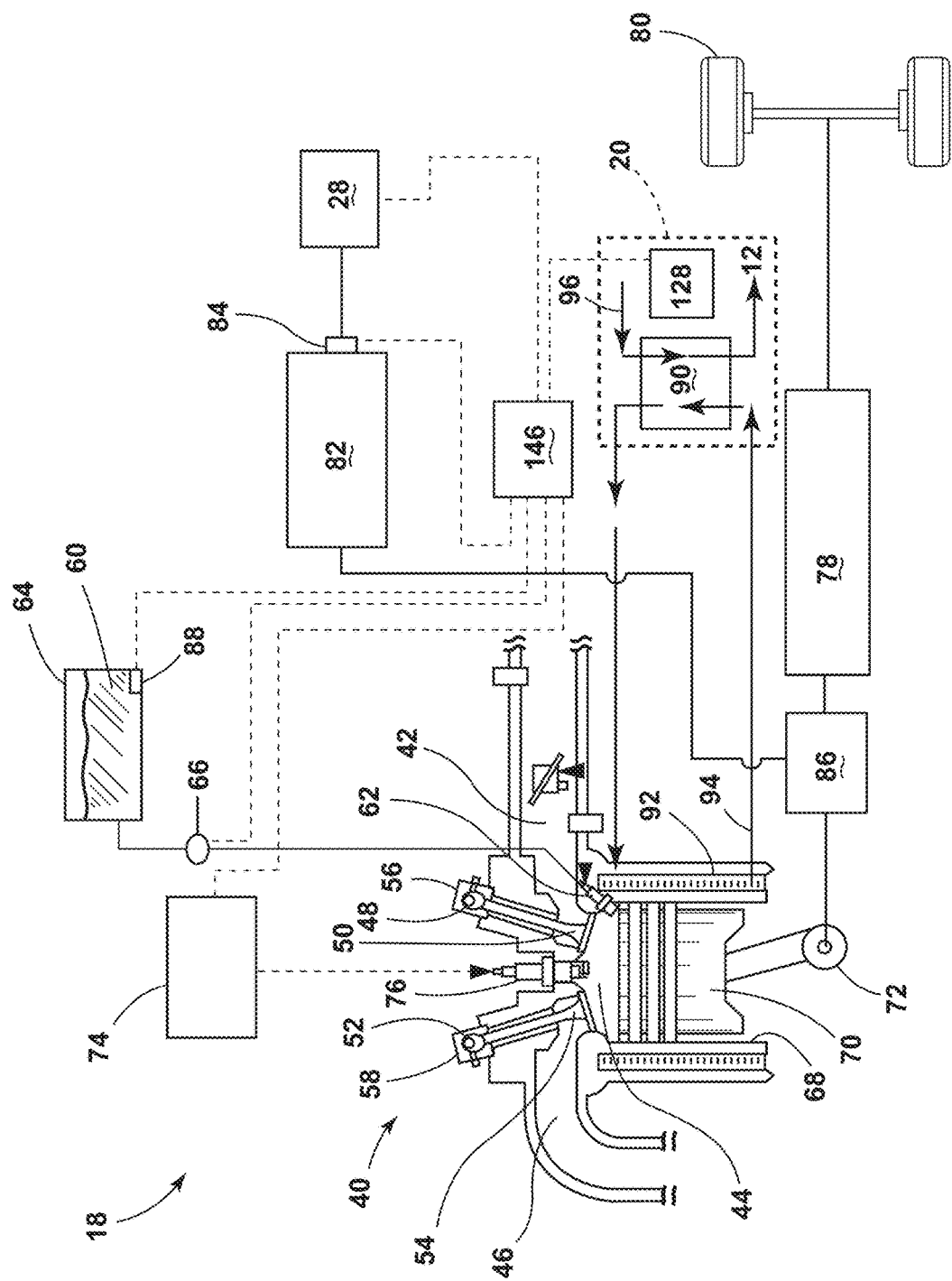
FIG. 3A is a schematic view of embodiments of the vehicle of FIG. 1, including the combustion engine as the propulsion system, the combustion engine with a coolant sleeve with coolant to exchange heat with air in a heat exchanger to heat the air to be directed into the interior thus operating as the heat source, with the air (heated) sanitizing the interior, and a low-voltage battery providing electrical power to the sources of the ultraviolet light.

In embodiments (FIG. 3A), the propulsion system 18 includes a combustion engine 40 configured to propel the vehicle 10. In embodiments, the combustion engine 40 includes an intake manifold 42, one or more combustion chambers 44 (sometimes referred to as "cylinders") in communication with the intake manifold 42, and an exhaust manifold 46 in communication with the one or more combustion chambers 44. The combustion engine 40 may include any suitable number of combustion chambers 44, including 1, 2, 3, 4, 5, 6, 8, 10, 12, or more combustion chambers 44. An intake cam 48 controls positioning of an intake valve 50 to control flow into the combustion chamber 44 from the intake manifold 42. An exhaust cam 52 controls positioning of an exhaust valve 54 to control flow from the combustion chamber 44 into the exhaust manifold 46. Actuators 56, 58 control the intake cam 48 and the exhaust cam 52, respectively. A fuel 60 is supplied to each of the one or more combustion chambers 44, such as through an injector 62. The fuel 60 is stored within the vehicle 10 within a tank 64. The tank 64 is in fluid communication with the combustion engine 40. For example, a pump 66 can be utilized to transfer the fuel 60 from the tank 64 to the injector 62. In embodiments, the fuel 60 is gasoline, alcohol blends, diesel, biodiesel, compressed natural gas, among other options, and combinations thereof. Each combustion chamber 44 includes a cylinder wall 68. A piston 70 is positioned interior of the cylinder wall 68. The piston 70 is connected to a crankshaft 72. An ignition system 74 can provide an ignition spark to the combustion chamber via a spark plug 76 to initiate combustion. Combustion could also be initiated via compression ignition in the combustion chamber 44. The combustion drives the piston 70, which drives the crankshaft 72. The crankshaft 72 drives a transmission 78. The transmission 78 may be a gearbox, a planetary gear system, or another type of transmission. The transmission 78 drives wheels 80 of the vehicle 10 thus propelling the vehicle 10. In embodiments, the vehicle 10 does not further include an electric motor to propel the vehicle 10.

Embodiments of the vehicle 10 that include the combustion engine 40 further include a low-voltage battery 82. The low-voltage battery 82 has a voltage. "Low-voltage" here means a voltage of less than 60 Volts (e.g., approximately 12 Volts). The low-voltage battery 82 is in electrical communication with the source 28 of the ultraviolet light 30 and the spark plug 76. A voltage sensor 84 is coupled to the low-voltage battery 82 to sense a voltage across terminals of the low-voltage battery 82. The battery voltage sensor 84 outputs a signal indicative of the voltage across the terminals of the low-voltage battery 82.

Embodiments of the vehicle 10 that include the combustion engine 40 further include an alternator 86. The alternator 86 is configured to convert the mechanical energy that the combustion engine 40 generates into electrical energy for storage in the low-voltage battery 82.

Embodiments of the vehicle 10 that include the combustion engine 40 further include a volume sensor 88. The volume sensor 88 produces a signal from which a volume of the fuel 60 within the tank 64 can be calculated or estimated. For example, the signal that the volume sensor 88 outputs can be responsive to a liquid pressure in the tank 64. In some examples, the volume sensor 88 can be a strain gauge configured to alter an electrical resistance in response to a liquid pressure exerted on a surface of the volume sensor 88. The greater the volume of the fuel 60 within the tank 64, the higher the liquid pressure within the tank 64, and the lower the resistance in the strain gauge. Thus, the resistance in the strain gauge may be indicative of the liquid pressure in the tank 64 in which the strain gauge is located, which is indicative of the volume of the fuel 60 within the tank 64.

Embodiments of the vehicle 10 that include the combustion engine 40 further include a heat exchanger 90. The heat exchanger 90 is in thermal communication with both the combustion engine 40 and the interior 12 of the vehicle 10. The heat exchanger 90 receives heat from the combustion engine 40 and expels to the interior 12 of the vehicle 10. For example, the cylinder wall 68 of the combustion chamber 44 of the combustion engine 40 can further include a sleeve 92. Coolant 94 flows through the sleeve 92 and extracts heat from the combustion chamber 44 that is generated via combustion of the fuel 60. The coolant 94 then flows to the heat exchanger 90. Simultaneously, air 96 also flows to the heat exchanger 90 and exchanges heat with the coolant 94. Temperature of the air 96 increases while temperature of the coolant 94 decreases at the heat exchanger 90. The air 96, heated, is then directed into the interior 12 of the vehicle 10, which thus increases the temperature of the interior 12 of the vehicle 10. The heat exchanger 90 thus, in embodiments, is the heat source 20 that increases the temperature of the interior 12 of the vehicle 10 to sanitize the interior 12. The coolant 94, cooled, is returned to the sleeve 92.

Figure 3B:
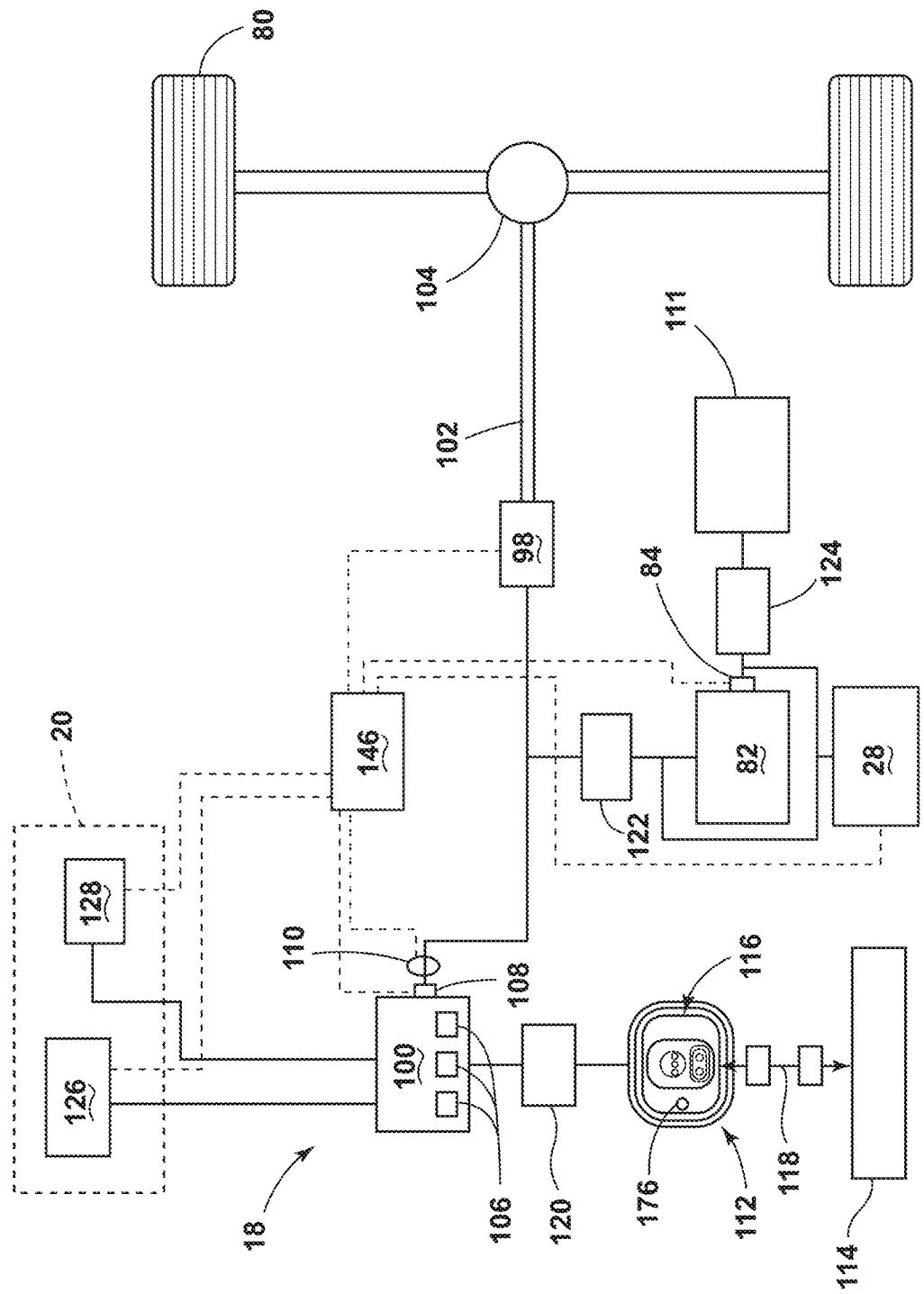
FIG. 3B is a schematic view of embodiments of the vehicle of FIG. 1, including an electric motor as the propulsion system, a low-voltage battery providing electrical power to the sources of the ultraviolet light, and a high-voltage battery providing electrical power to a heating element has the heat source.

In embodiments (FIG. 3B), the propulsion system 18 includes an electric motor 98 configured to propel the vehicle 10. A high-voltage battery 100 is in electrical communication with the electric motor 98 and provides electrical power to the electric motor 98. The high-voltage battery 100 is sometimes referred to as a "traction battery." The high-voltage battery 100 is in further electrical communication with the source 28 of the ultraviolet light 30. The electric motor 98 outputs torque to a shaft 102. The shaft 102 is coupled to a differential 104. The differential 104 can include a plurality of gears that enable the transfer of torque to the wheels 80. The differential 104 thus drives the wheels 80 of the vehicle 10, thus propelling the vehicle 10. Such a vehicle 10 is sometimes referred to as a "battery electric vehicle" or "BEV" for short. In embodiments, the vehicle 10 does not further include a combustion engine 40 to propel the vehicle 10.

In embodiments, the high-voltage battery pack includes a plurality of battery arrays 106. The battery arrays 106 can each include a grouping of battery cells arranged as a module. In embodiments, the electric motor 98 is part of a regenerative braking system that outputs electrical power to the high-voltage battery 100. The high-voltage battery 100 includes a voltage sensor 108 and a current sensor 110. As discussed further below, the high-voltage battery 100 has a state-of-charge.

In embodiments, the vehicle 10 that includes the electric motor 98 to propel the vehicle 10 additionally includes the low-voltage battery 82. In such embodiments, the low-voltage battery 82 is sometimes referred to as an "auxiliary battery." In general, the high-voltage battery 100 provides electrical power to the electric motor 98, while the low-voltage battery 82 does not. Rather, the low-voltage battery 82 can provide electrical power to various low-voltage loads 111 of the vehicle 10. Low-voltage loads 111 may include infotainment systems, lighting systems, power windows, power seats, cooling fans, AC compressors, instrument clusters, and control modules, among other things. In embodiments, the low-voltage battery 82 is in communication with the source 28 of the ultraviolet light 30. As mentioned, a battery voltage sensor 84 is coupled to the battery to sense a voltage across terminals of the low-voltage battery 82. The battery voltage sensor 84 outputs a signal indicative of the voltage across the terminals of the low-voltage battery 82.

In embodiments, the vehicle 10 that includes the electric motor 98 to propel the vehicle 10 further includes a charging system 112 to allow an external power source 114 to recharge (i.e., increase the state-of-charge of) the high-voltage battery 100. The charging system 112 can be connected to an external power source 114. The external power source 114 can be a utility-supplied electrical grid, a charging station, another battery such as located at a residence, which may be itself charged via solar, wind, or other energy sources. The charging system 112 provides electrical power to the high-voltage battery 100 and, in embodiments, the low-voltage battery 82.

In embodiments, the vehicle 10 that includes the electric motor 98 to propel the vehicle 10 further includes a charge port 116. Electric vehicle supply equipment 118 (EVSE), such as a charge cord of a charging station, can operably connect the charge port 116 to the external power source 114. The charge port 116 is adapted to receive a respective coupler of the EVSE 118. The EVSE 118 may have pins that mate with corresponding recesses of the charge port 116. The EVSE 118 may provide circuitry and controls to regulate and manage the transfer of energy between the external power source 114 and the vehicle 10. The charge port 116 can receive alternating current ("AC") electrical power or both AC electrical power and direct current ("DC") electrical power. The charge port 116 can be equipped to accommodate one or more conventional voltage sources from the external power source 114, such as 110 Volts and 220 Volts. A power converter 120 can convert AC electrical power received from the external power source 114 to DC electrical power for charging the high-voltage battery 100. For example, the power converter 120 can be an AC-to-DC inverter.

A DC-to-DC electrical power converter 122 can be disposed in electrical communication between the high-voltage battery 100 and the low-voltage battery 82. The DC-to-DC electrical power converter 122 can decrease the voltage of electrical power supplied from the high-voltage battery 100 to the low-voltage battery 82 and to the source 28 of the ultraviolet light 30. A DC-to-AC electrical power converter 124 can be disposed in electrical communication between the low-voltage battery 82 and the low-voltage loads 111. Some low-voltage loads 111 can accept DC electrical power from the low-voltage battery 82, in which case the DC-to-AC electrical power converter 124 is not disposed in electrical communication between the low-voltage battery 82 and those low-voltage loads 111.

In embodiments, the heat source 20 of the vehicle 10 that includes the electric motor 98 to propel the vehicle 10 further includes a heating element 126 that increases temperature of the air 96 in the interior 12. The air 96 is directed over the heating element 126 and then directed to the interior 12 of the vehicle 10. In embodiments, the heat source 20 of the vehicle 10 that includes the electric motor 98 further includes a seat heating element 128 disposed within each of one or more of the seating assemblies 24 of the vehicle 10. The heating element 126 and the seat heating element(s) 128 can each be a Peltier device. Alternatively, the heating element 126 and the seat heating element(s) 128 can produce heat through resistance of electrical power, such as electrical power that the high-voltage battery 100 provides. In embodiments, the heating element 126 (as the heat source 20) has a positive temperature coefficient "PTC"—that is, a resistance that is positively related to voltage applied to the heating element 126. For example, the heating element 126 may contain a doped polycrystalline ceramic, such as barium titanate ($BaTiO_3$). As a constant voltage is applied to the heating element 126 at an initial cool temperature, the resistance is initially low, and the current is initially high. As the heating element 126 generates heat, the temperature of the heating element 126 increases, and correspondingly the resistance increases and the current decreases, until the temperature, resistance, and current all reach a steady state. The steady-state temperature of the heating element 126 can therefore be controlled by selecting a voltage applied to the heating element 126. The heating element 126 thus efficiently generates heat while occupying relatively little space.

Figure 3C:
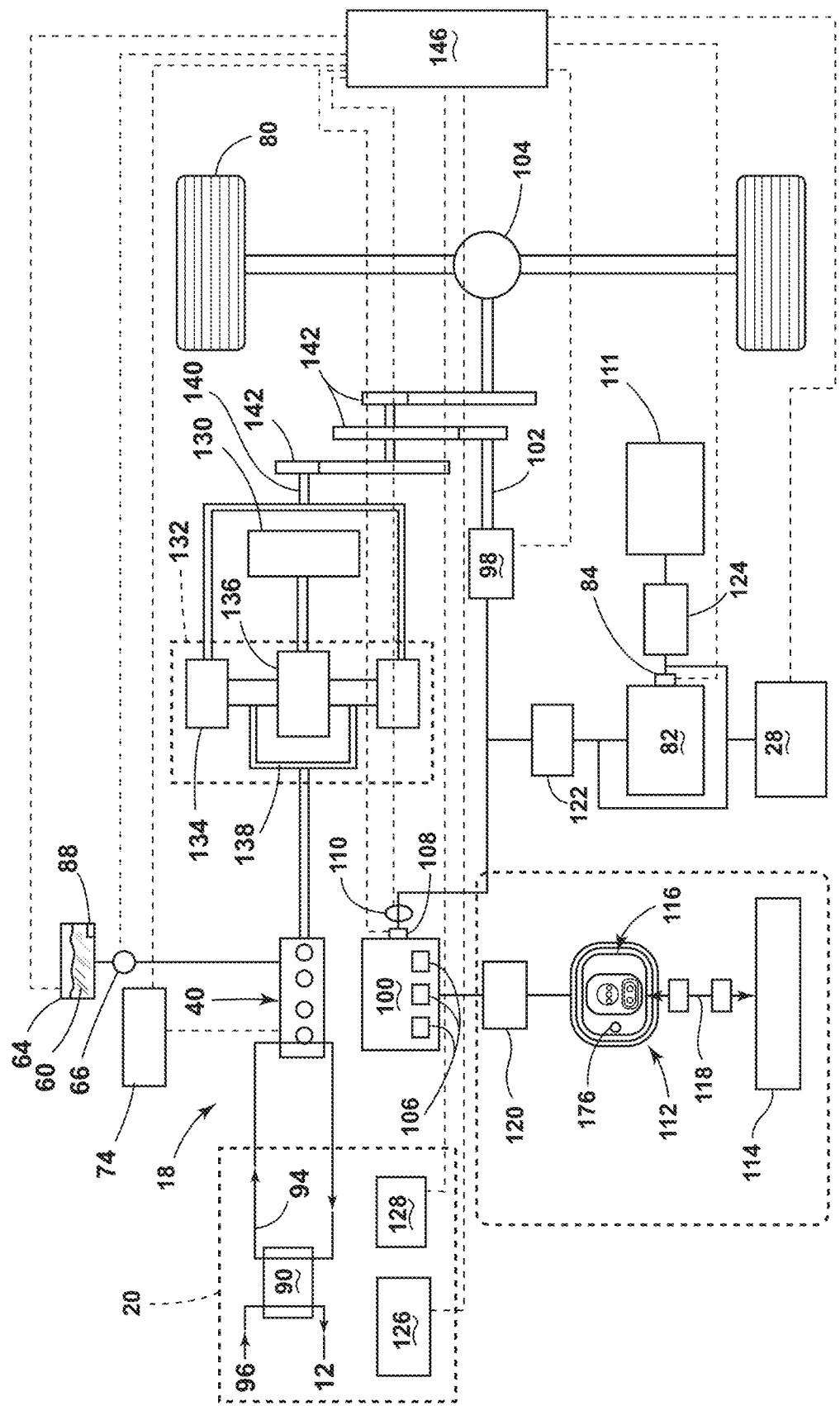
FIG. 3C is a schematic view of embodiments of the vehicle of FIG. 1, including both the combustion engine and the electric motor as the propulsion system and aspects from the embodiments of FIGS. 3A and 3B as the heat source.

In embodiments (FIG. 3C), the vehicle 10 includes both the combustion engine 40 and the electric motor 98 configured to propel the vehicle 10. Such a vehicle 10 is sometimes referred to as a "hybrid vehicle" or "hybrid electric vehicle." In such embodiments, in addition to the electric motor 98, the vehicle 10 includes the high-voltage battery 100 and the low-voltage battery 82 described in connection with the vehicle 10 illustrated at FIG. 3B. The vehicle 10 can further include the DC-to-DC power converter 122, the DC-to-AC power converter 124, and the low voltage loads 111. In embodiments, the vehicle 10 includes plug-in components, such as the power converter 120, the charging system 112 with the charge port 116, and the EVSE 118 to connect to the external power source 114, as discussed above for the vehicle 10 described in connection with FIG. 3B. In such embodiments, the vehicle 10 is sometimes referred to as a "plug-in hybrid electric vehicle" or "PHEV" for short. In other embodiments, the vehicle 10 does not include the plug-in components. In such embodiments, the vehicle 10 is sometimes referred to as a "full hybrid electric vehicle" or "FHEV" for short.

The vehicle 10 (of FIG. 3C) further includes a generator 130 and a power transfer unit 132. The power transfer unit 132 can be a planetary gear set that includes a ring gear 134, a sun gear 136, and a carrier assembly 138. The ring gear 134 can be connected to a shaft 140, which is connected to the wheels 80 of the vehicle 10 through a plurality of gears 142. The gears 142 thus transfer torque from the combustion engine 40 to the differential 104 to drive the wheels 80. In addition, the electric motor 98 can drive the wheels 80 via outputting torque to the shaft 102, which is connected to certain of the gears 142, which, in turn, drive the differential 104 to drive the wheels 80. Further, the combustion engine 40 can drive the generator 130 via the power transfer unit 132 to convert kinetic energy to electrical energy, which can then be delivered to the electric motor 98, the high-voltage battery 100, or the low-voltage battery 82. Moreover, the generator 130 can convert electrical energy into kinetic energy by outputting torque onto a shaft 144 connected to the sun gear 136 of the power transfer unit 132. The combustion engine 40 otherwise includes the features described above for the vehicle 10 described in connection with FIG. 3A. The vehicle 10 further includes the ignition system 74, the tank 64 containing the volume of fuel 60, the volume sensor 88, the pump 66, and the heat exchanger 90 to exchange heat from the coolant 94 to the air 96 directed to the interior 12, as discussed above for the vehicle 10 described in connection with FIG. 3A. The vehicle 10 further includes the voltage sensor 108 and the current sensor 110 related to the high-voltage battery 100, the heating element 126 to heat air 96 directed into the interior 12, and the heating element(s) disposed in the one or more seating assemblies 24. The heating element 126 can have a positive temperature coefficient, as explained above.

Figure 4:
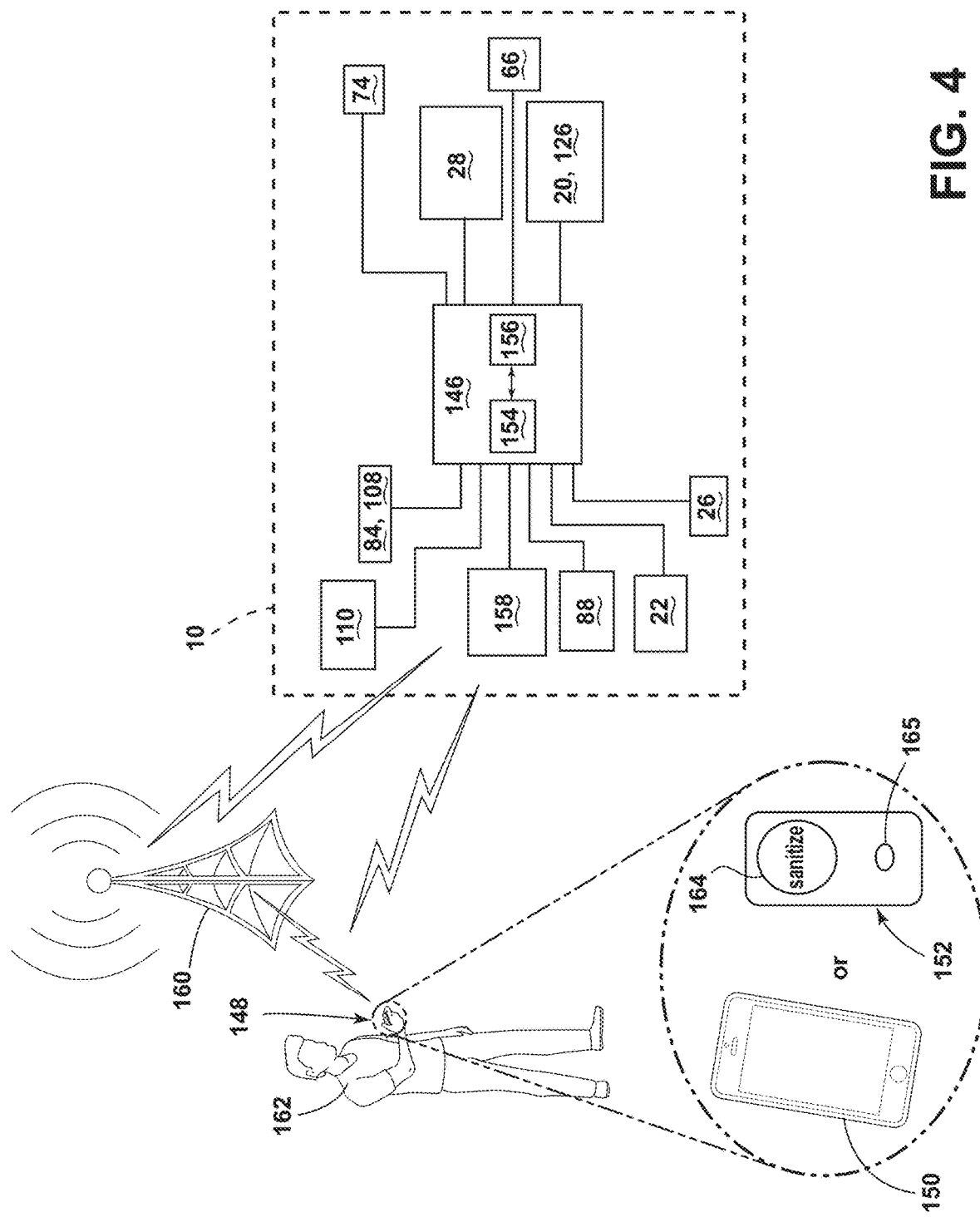
FIG. 4 is a schematic view of the controller of FIG. 1, illustrating a person commanding sanitization of the vehicle of FIG. 1 while outside of the vehicle via a remote user interface that communicates with the controller either directly or via an external network.

Referring now to FIG. 4, the vehicle 10 further includes a controller 146. The controller 146 is in communication with the heat source 20, the source 28 of the ultraviolet light 30, the temperature sensor 22, a remote user interface 148 (discussed further below), and the occupancy sensor 26. In embodiments of the vehicle 10 that include the combustion engine 40 (e.g., FIG. 3A), the controller 146 is in further communication with the low-voltage battery 82 via the battery voltage sensor 84, the pump 66, the ignition system 74, the volume sensor 88, and the seat heating element(s) 128. In embodiments of the vehicle 10 that include the electric motor 98 (e.g., FIG. 3B), the controller 146 is in further communication with the low-voltage battery 82 via the voltage sensor 84, the high-voltage battery 100 via the voltage sensor 108 and the current sensor 110, the electric motor 98, the heating element 126, and the seat heating element(s) 128. In embodiments of the vehicle 10 that include both the combustion engine 40 and the electric motor 98 (see, e.g., FIG. 3C), the controller 146 is in further communication with the pump 66, the ignition system 74, the volume sensor 88, the low-voltage battery 82 via the voltage sensor 84, the high-voltage battery 100 via the voltage sensor 108 and the current sensor 110, the electric motor 98, the heating element 126, and the seat heating element(s) 128. As mentioned above, the heat source 20 includes one or more of the heating element 126, the seat heating element(s) 128, and the combustion engine 40 heating the air 96 directed into the interior 12 via the heat exchange 90. The controller 146 controls the combustion engine 40 aspect of the heat source 20 through at least control of the pump 66 and the ignition system 74.

The controller 146 can thus cause (i) the heat source 20 to increase the temperature of the interior 12, (ii) the source 28 of the ultraviolet light 30 to emit the ultraviolet light into the interior 12, or (iii) both (i) and (ii). The controller 146 does so upon receiving a command from the remote user interface 148. In embodiments, the remote user interface 148 is provided by a mobile device 150, such as a tablet, a smart phone, a smart watch, and the like. In embodiments, the remote user interface 148 is provided a key fob 152.

The controller 146 includes a processor 154 and memory 156. The processor 154 can be any suitable processing device or set of processing devices such as, but not limited to, a microprocessor, a microcontroller-based platform, an integrated circuit, one or more field programmable gate arrays (FPGAs), one or more tensor processing units (TPUs), and/or one or more application-specific integrated circuits (ASICs). The memory 156 can be volatile memory (e.g., RAM including non-volatile RAM, magnetic RAM, ferroelectric RAM, etc.), non-volatile memory (e.g., disk memory, FLASH memory, EPROMs, EEPROMs, memristor-based non-volatile solid-state memory, etc.), unalterable memory (e.g., EPROMs), read-only memory, and/or high-capacity storage devices (e.g., hard drives, solid-state drives, etc.). The memory 156 can include multiple kinds of memory, particularly volatile memory and non-volatile memory. The memory 156 is computer readable media on which one or more sets of instructions, such as the software for operating a method or methods of the present disclosure, can be embedded. The instructions may embody one or more of the methods or logic as described herein. For example, the instructions reside completely, or at least partially, within the memory 156, the computer readable medium, and/or within the processor 154 during execution of the instructions. In other words, the processor 154 can execute programs stored in memory 156 to effectuate control of the heat source 20 and the source 28 of the ultraviolet light 30 in the manner herein described.

The vehicle 10 further includes a communication module 158 that is in communication with the controller 146. The communication module 158 includes wired or wireless network interfaces to enable communication with an external network 160. The communication module 158 also includes hardware (e.g., processors, memory, storage, antenna, etc.) and software to control the wired or wireless network interfaces. In the illustrated example, the communication module 158 includes one or more communication controllers for cellular networks (e.g., Global System for Mobile Communications (GSM), Universal Mobile Telecommunications System (UMTS), Long Term Evolution (LTE), Code Division Multiple Access (CDMA)), Near Field Communication (NFC) and/or other standards-based networks (e.g., WiMAX (IEEE 802.16m), local area wireless network (including IEEE 802.11 a/b/g/n/ac or others), Wireless Gigabit (IEEE 802.11ad), etc.). The communication module 158 is thus configured to communicate with the remote user interface 148 via the external network 160.

In embodiments, the communication module 158 is configured to communicate with the remote user interface 148 directly. In some examples, the communication module 158 includes a wired or wireless interface (e.g., an auxiliary port, a Universal Serial Bus (USB) port, a Bluetooth® wireless node, etc.) to communicatively couple with the remote user interface 148 (e.g., when the remote user interface 148 is provided by a the key fob 152, the mobile device 150, etc.).

Figure 5A:
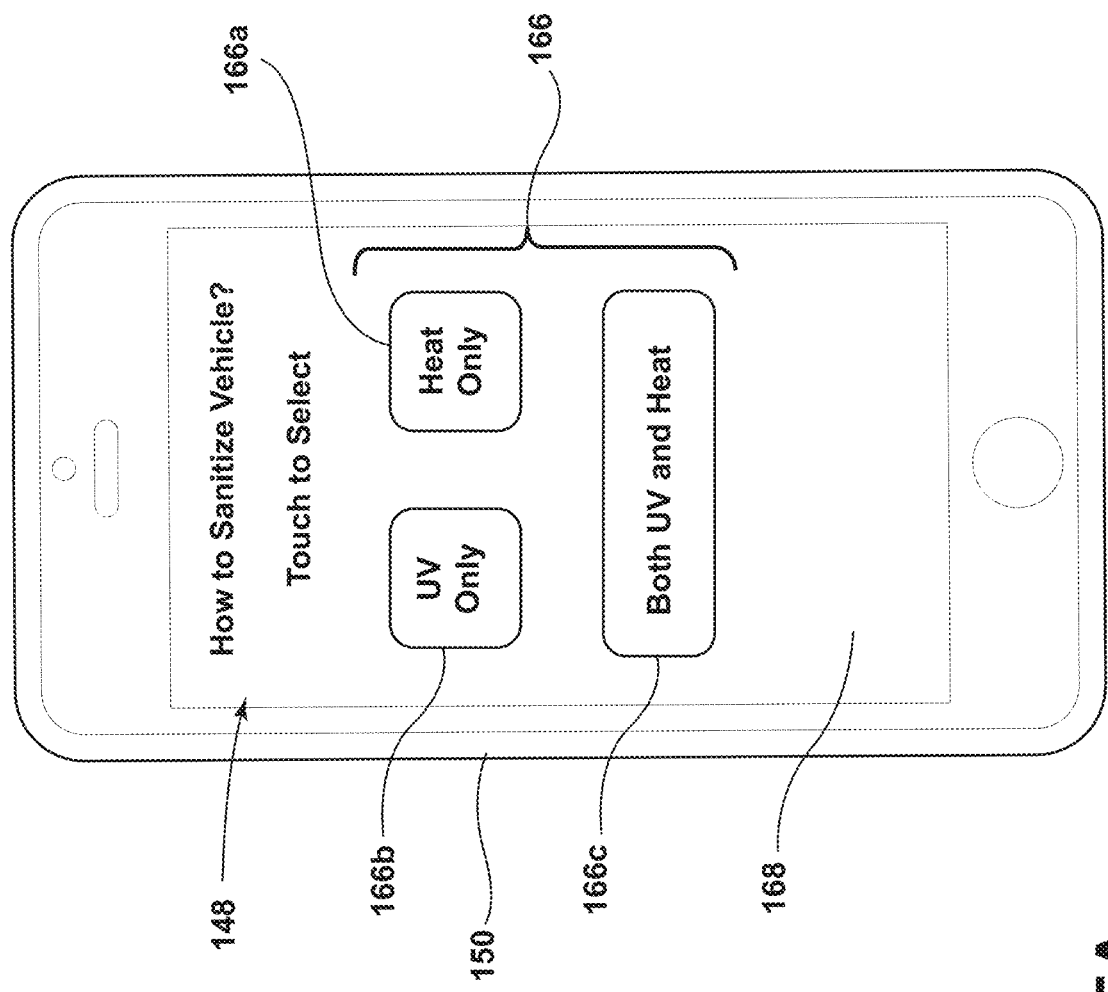
FIG. 5A is a view of an embodiment of the remote user interface, illustrating selectable options on a touch screen display for the person to touch to command the vehicle to sanitize the vehicle, such as sanitization via ultraviolet light only, sanitization via increased temperature, or both.
Figure 5B:
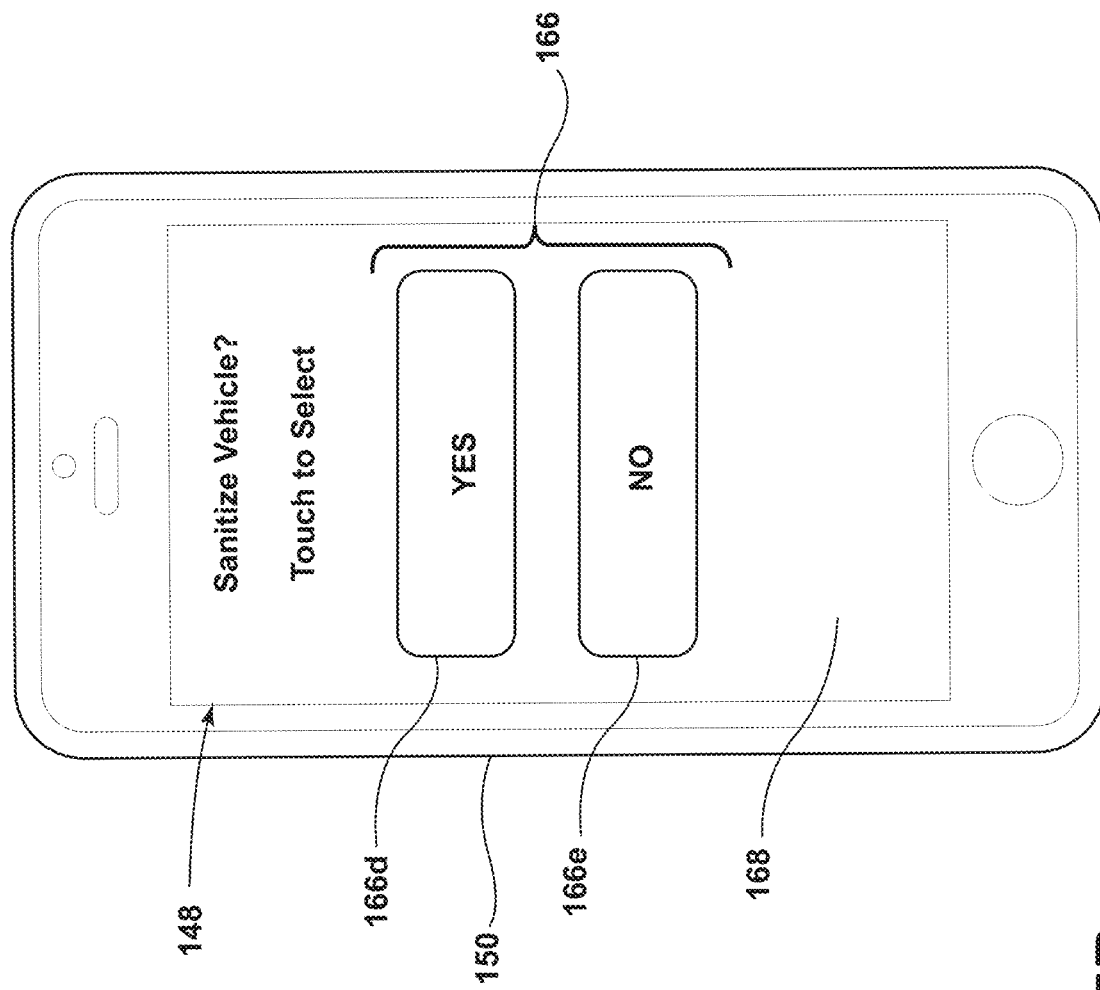
FIG. 5B is a view of the remote user interface of FIG. 5A, illustrating more limited selectable options with touchable buttons for "YES" or "NO", and the person would touch "YES" to command the sanitization and the remote user interface communicates the command to the vehicle.

Referring now additionally to FIGS. 5A and 5B, in use, a person 162 issues a command to the vehicle 10 via the remote user interface 148 for the vehicle 10 to sanitize the interior 12. In embodiments, the remote user interface 148 includes a single option, such as a "sanitize" button 164 that issues the command to the controller 146. If the person 162 presses the button 164, the remote user interface 148 sends the command to the controller 146 to the vehicle 10 via the communication module 158 and the controller 146 of the vehicle 10 causes the heat source 20 to increase the temperature of the interior 12 or the source 28 of the ultraviolet light 30 to emit the ultraviolet light into the interior 12 to sanitize the interior 12, or both. As will be further discussed below, the controller 146 can decide whether to sanitize via the heat source 20 or the source 28 of the ultraviolet light 30. In embodiments, a default is for the controller 146 to sanitize the interior 12 via both activation of the heat source 20 and the source 28 of the ultraviolet light 30. In embodiments, the remote user interface 148 is the key fob 152 that presents the "sanitize" button 164.

In embodiments, the remote user interface 148 includes one or more selectable options 166 on a touch screen 168 of the mobile device 150. For example, in embodiments (see FIG. 5A), the selectable options 166 include a first option 166a to sanitize via heat, a second option 166b to sanitize via emission of the ultraviolet light 30, and a third option 166c to sanitize via both heat and emission of the ultraviolet light 30. In embodiments, the mobile device 150 includes an application program that provides the selectable options 166 and communicates the selected option to the vehicle 10, either directly or via the external network 160. If the person 162 selected the first option 166a, then the remote user interface 148 sends the command to the controller 146 of the vehicle 10 via the communication module 158, and the controller 146 of the vehicle 10 causes the heat source 20 to increase the temperature of the interior 12 to sanitize the interior 12. If the person 162 selected the second option 166b, then the remote user interface 148 sends the command to the controller 146 of the vehicle 10 via the communications module 158 and the controller 146 of the vehicle 10 causes the source 28 of the ultraviolet light 30 to emit the ultraviolet light 30 into the interior 12 to sanitize the interior 12. If the person 162 selected the third option 166c, then the remote user interface 148 sends the command to the controller 146 of the vehicle 10 via the communication module 158 and the controller 146 of the vehicle 10 causes the heat source 20 to increase the temperature of the interior 12 and the source 28 of the ultraviolet light 30 to emit the ultraviolet light 30 into the interior 12 to sanitize the interior 12.

In other embodiments (see FIG. 5B), the selectable options 166 include an option 166d to sanitize ("YES") and an option 166e not to sanitize ("NO"). If the person 162 selected the option 166d to sanitize, then the remote user interface 148 sends the command to the controller 146 of the vehicle 10 via the communication module 158, and the controller 146 determines whether to sanitize via activation of the heat source 20 to increase the temperature of the interior 12, to sanitize via activation of the source 28 of the ultraviolet light 30, or sanitization via both activation of the heat source 20 and the source 28 of the ultraviolet light 30. In embodiments, a default is for the controller 146 to sanitize the interior 12 via both activation of the heat source 20 and the source 28 of the ultraviolet light 30.

The controller 146 causes the heat source 20 to increase the temperature of the interior 12 of the vehicle 10 sufficiently and for a sufficient period of time to sanitize the interior 12 of the vehicle 10. In embodiments, the heat source 20 raises the temperature of the interior 12 to at least 60° C. and maintains the temperature for at least 1 hour. In embodiments, the heat source 20 raises the temperature of the interior 12 to at least 65° C. and maintains the temperature for at least 45 minutes. The higher the temperature, the shorter the period of time required for the interior 12 to be maintained at that temperature to sanitize the interior 12.

The controller 146 causes the source 28 of the ultraviolet light 30 to emit the ultraviolet light 30 for a period of time sufficient to sanitize the interior 12 of the vehicle 10. In general, the closer the source 28 of the ultraviolet light 30 is to any particular surface at the interior 12 of the vehicle 10, the shorter the period of time of emitting the ultraviolet light 30 is required to sanitize that particular surface. In addition, the higher the intensity of the ultraviolet light 30 emitted, the shorter the period of time of emitting the ultraviolet light 30 is required to sanitize that particular surface. Further, causing the heat source 20 to increase the temperature of the interior 12 simultaneously with causing the source 28 of the ultraviolet light 30 to emit the ultraviolet light 30, reduces the period of time required to sanitize the vehicle 10 than if either heating or the ultraviolet light 30 were used alone.

In embodiments, the controller 146 determines that no occupant is in the interior 12 of the vehicle 10 before conducting sanitization. For example, the controller 146, as a function of the signal from the occupancy sensor 26, determines that no occupant occupies the interior 12 of the vehicle 10 before causing the source 28 of the ultraviolet light 30 to emit the ultraviolet light 30 into the interior 12. As another example, the controller 146, as a function of the signal from the occupancy sensor 26, determines that no occupant occupies the interior 12 of the vehicle 10 before causing the heat source 20 to increase the temperature of the interior 12 of the vehicle 10. In instances where the controller 146 has already caused the source 28 of the ultraviolet light 30 to emit the ultraviolet light 30 or has already caused the heat source 20 to increase the temperature of the interior 12, the controller 146 ceases so causing upon receiving the signal from the occupancy sensor 26 that an occupant is within the interior 12 of the vehicle 10.

In embodiments of the vehicle 10 (FIGS. 3A, 3C) where the propulsion system 18 includes a combustion engine 40 configured to propel the vehicle 10, upon receiving the command from the remote user interface 148 to cause of the source 28 of the ultraviolet light 30 to emit the ultraviolet light 30 into the interior 12, the controller 146 first determines from the signal from the voltage sensor 84 whether the voltage of the low-voltage battery 82 is greater than a predetermined voltage. In embodiments, if the controller 146 determines that the voltage of the low-voltage battery 82 is greater than the predetermined voltage, then the controller 146 causes the source 28 of the ultraviolet light 30 to emit the ultraviolet light 30. However, if the controller 146 determines that the voltage of the low-voltage battery 82 is not greater than the predetermined voltage, then the controller 146 starts the combustion engine 40 to increase the voltage of the low-voltage battery 82 to the predetermined voltage. For example, the controller 146 can activate the pump 66 and the ignition system 74 to activate the combustion engine 40, and the alternator 86 converts kinetic energy from the combustion engine 40 into electrical energy that is directed to the low-voltage battery 82, which increases the voltage of the low-voltage battery 82. After the voltage of the low-voltage battery 82 has increased to be greater than the predetermined voltage, then the controller 146 causes the source 28 of the ultraviolet light 30 to emit the ultraviolet light 30 into the interior 12 for the period of time to sanitize the interior 12. The controller 146 can deactivate the combustion engine 40 after the voltage of the low-voltage battery 82 is greater than the predetermined voltage.

In embodiments, before the controller 146 activates the combustion engine 40 to increase the voltage of the low-voltage battery 82, the controller 146 determines the volume of the fuel 60 within the tank 64. The controller 146 determines the volume of the fuel 60 within the tank 64 based on the signal from the volume sensor 88. If the controller 146 determines that the volume of the fuel 60 is greater than a predetermined volume, then the controller 146 starts the combustion engine 40 to increase the voltage of the low-voltage battery 82. If the controller 146 determines that the volume of the fuel 60 is not greater than the predetermined volume, then the controller 146 does not start the combustion engine 40. And, if the voltage of the low-voltage battery 82 is below the predetermined voltage, then the controller 146 does not activate the source 28 of the ultraviolet light 30.

In embodiments of the vehicle 10 (e.g., FIGS. 3A, 3C) where the propulsion system 18 includes the combustion engine 40 configured to propel the vehicle 10, upon receiving the command from the remote user interface 148 to cause the heat source 20 to increase the temperature of the interior 12, the controller 146 first determines the volume of the fuel 60 within the tank 64. The controller 146 determines the volume of the fuel 60 within the tank 64 based on the signal from the volume sensor 88. If the controller 146 determines that the volume of the fuel 60 is greater than a predetermined volume, then the controller 146 starts the combustion engine 40 to increase the temperature of the interior 12 via the heat exchanger 90. If the controller 146 determines that the volume of the fuel 60 is not greater than the predetermined volume, then the controller 146 does not start the combustion engine 40. The predetermined volume that the controller 146 compares before determining whether to start the combustion engine 40 to heat the interior 12 can be different (e.g., greater) than the predetermined volume that the controller 146 compares before determining whether to start the combustion engine 40 to increase the voltage of the battery in order activate the source 28 of the ultraviolet light 30.

In embodiments of the vehicle 10 (e.g., FIGS. 3A, 3C) where the propulsion system 18 includes the combustion engine 40 configured to propel the vehicle 10, upon receiving the command from the remote user interface 148 to sanitize the vehicle 10, the controller 146 first determines the temperature of the interior 12 of the vehicle 10. As mentioned, the remote user interface 148 can provide the "sanitize" button 164 or touchable binary selectable options 166d, 166e to the person 162 regarding whether to sanitize the interior 12 of the vehicle 10, and the controller 146 decides whether to increase the temperature of the interior 12, to emit the ultraviolet light 30, or both increase the temperature and emit the ultraviolet light 30. In embodiments, the controller 146 premises that decision on the temperature of the interior 12 of the vehicle 10. In embodiments, when the controller 146, as a function of the signal from the temperature sensor 22, determines that the temperature of the vehicle 10 is less than a predetermined temperature, then the controller 146 determines to sanitize by increasing the temperature of the interior 12 (either alone or in combination with the ultraviolet light 30) and starts the combustion engine 40 to increase the temperature of the interior 12 via the heat exchanger 90. In contrast, when the controller 146 determines that the temperature of the vehicle 10 is greater than the predetermined temperature, then the controller 146 determines to sanitize via the ultraviolet light 30 alone.

In embodiments of the vehicle 10 (e.g., FIGS. 3B, 3C) where the propulsion system 18 includes the electric motor 98 to propel the vehicle 10, upon receiving the command from the remote user interface 148 to cause of the source 28 of the ultraviolet light 30 to emit the ultraviolet light 30 into the interior 12, the controller 146 first determines from the signal from the voltage sensor 84 whether the voltage of the low-voltage battery 82 is greater than a predetermined voltage. In embodiments, if the controller 146 determines that the voltage of the low-voltage battery 82 is greater than the predetermined voltage, then the controller 146 causes the source 28 of the ultraviolet light 30 to emit the ultraviolet light 30. However, in embodiments, if the controller 146 determines that the voltage of the low-voltage battery 82 is not greater than the predetermined voltage, then the controller 146 does not cause the source 28 of the ultraviolet light 30 to emit the ultraviolet light 30.

In embodiments of the vehicle 10 (FIGS. 3B, 3C) where the propulsion system 18 includes the electric motor 98 to propel the vehicle 10, upon receiving the command from the remote user interface 148 to cause of the source 28 of the ultraviolet light 30 to emit the ultraviolet light 30 into the interior 12, the controller 146 first determines whether the state-of-charge of the high-voltage battery 100 is greater than a predetermined state-of-charge. The controller 146 can determine the state-of-charge of the high-voltage battery 100 based on the signals from the voltage sensor 108 and the current sensor 110. The controller 146 can utilize various techniques to compute the state-of-charge. For example, an ampere-hour integration may be implemented in which the current through the high-voltage battery 100 is integrated over time. In addition, the state-of-charge can be estimated based on the output of the voltage sensor 108. The specific technique utilized may depend upon the chemical composition and characteristics of the high-voltage battery 100. In circumstances where the voltage of the low-voltage battery 82 is below the predetermined voltage, the controller 146 can utilize the high-voltage battery 100 to power the source 28 of the ultraviolet light 30 to emit the ultraviolet light 30 instead. However, in those circumstances, the controller 146 determines that the state-of-charge of the high-voltage battery 100 is greater than the predetermined state-of-charge before causing the source 28 of the ultraviolet light 30 to emit the ultraviolet light 30 into the interior 12. In embodiments, if the controller 146 determines that state-of-charge of the high-voltage battery 100 is not greater than the predetermined state-of-charge, then the controller 146 does not cause the source 28 of the ultraviolet light 30 to emit the ultraviolet light 30.

In embodiments of the vehicle 10 (e.g., FIGS. 3B, 3C) where the propulsion system 18 includes the electric motor 98 to propel the vehicle 10, upon receiving the command from the remote user interface 148 to cause the source 28 of the ultraviolet light 30 to emit the ultraviolet light 30 into the interior 12, the controller 146 first determines that the state-of-charge of the high-voltage battery 100 is not greater than the predetermined state-of-charge. In circumstances where the voltage of the low-voltage battery 82 is not greater than the pre-determined voltage and the state-of-charge of the high-voltage battery 100 is not greater than the predetermined state-of-charge, the controller 146 can nevertheless cause the source 28 of the ultraviolet light 30 to emit the ultraviolet light 30 if the high-voltage battery 100 is connected to the external power source 114. In other words, in embodiments, the controller 146 causes the source 28 of the ultraviolet light 30 to emit the ultraviolet light 30 despite the voltage of the low-voltage battery 82 being not greater than the predetermined voltage and the state-of-charge of the high-voltage battery 100 being not greater than the predetermined state-of-charge, as long as the high-voltage battery 100 is connected to the external power source 114. The external power source 114 provides the requisite electrical power to the source 28 of the ultraviolet light 30.

In embodiments of the vehicle 10 (e.g., FIGS. 3B, 3C) where the propulsion system 18 includes the electric motor 98 to propel the vehicle 10, upon receiving the command from the remote user interface 148 to cause the heat source 20 to increase the temperature of the interior 12, the controller 146 determines that the state-of-charge of the high-voltage battery 100 is greater than a predetermined state-of-charge before causing the heat source 20 to increase the temperature of the interior 12. In embodiments, the predetermined state-of-charge of the high-voltage battery 100 for purposes of determining whether to activate the heat source 20 to sanitize the interior 12 is different (e.g., greater) that the predetermined state-of-charge of the high-voltage battery 100 for purposes of determining whether to activate the source 28 of the ultraviolet light 30 to sanitize the interior 12. However, if the controller 146 determines that the high-voltage battery 100 is connected to the external power source 114, then the controller 146 nevertheless causes the heat source 20 to increase the temperature of the interior 12. The external power source 114 provides the requisite electrical power to the heat source 20.

Figure 6A:
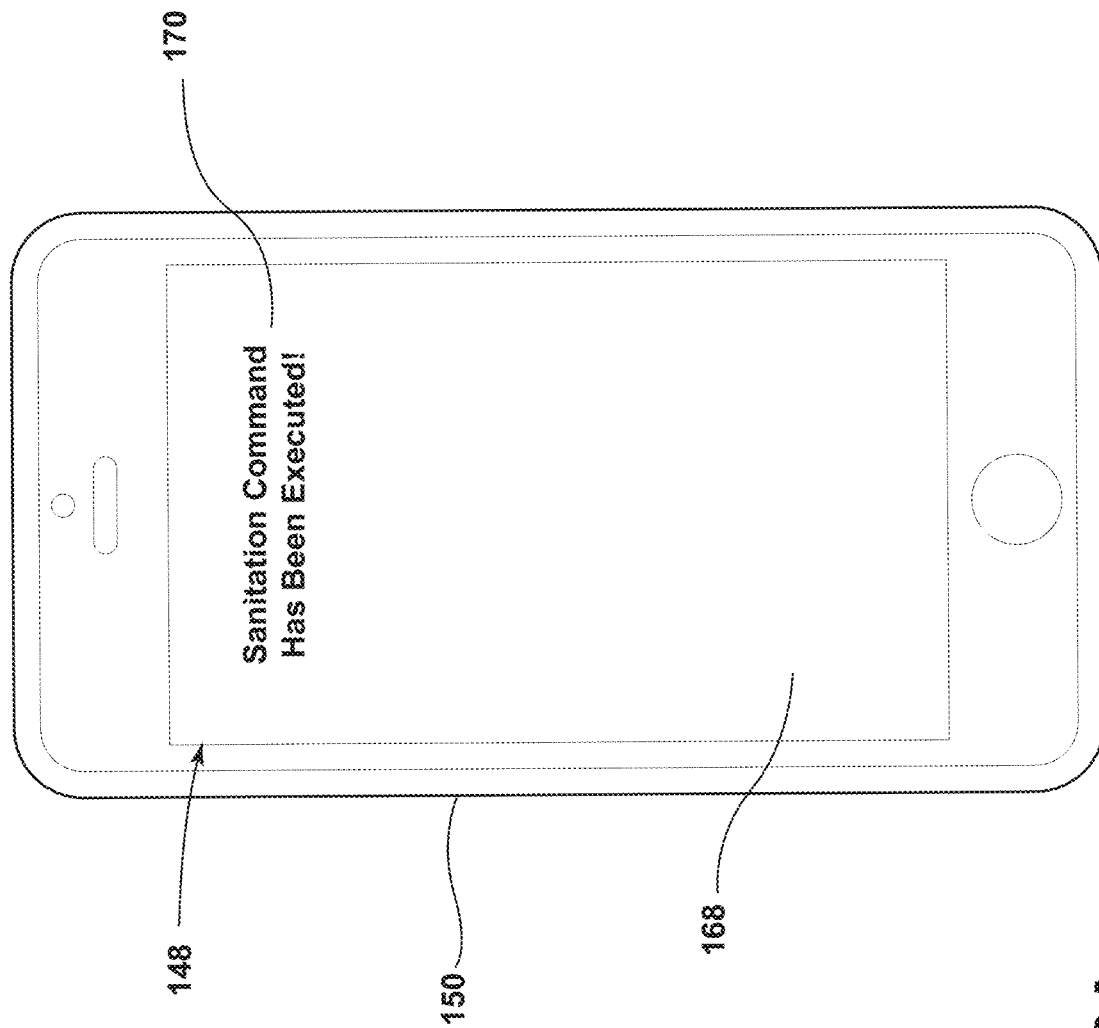
FIG. 6A is a view of the remote user interface of FIG. 5A, illustrating a communication from the vehicle displayed at the remote user interface to inform the person that the vehicle has successfully executed the sanitization command.
Figure 6B:
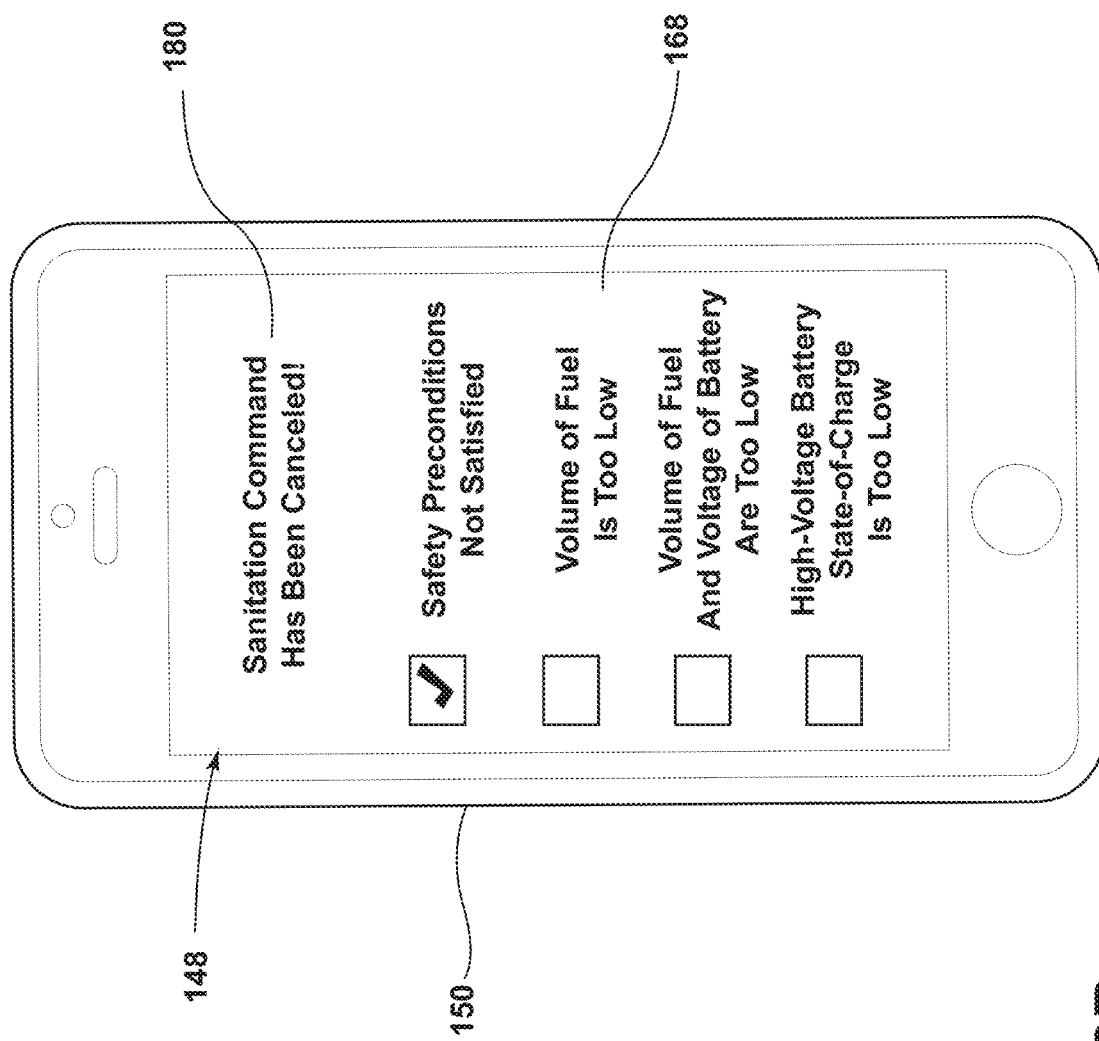
FIG. 6B is a view of the remote user interface of FIG. 5A, illustrating a communication from the vehicle displayed at the remote user interface to inform the person that the vehicle has cancelled the sanitization command, and optionally providing an explanation such as the "Volume of Fuel is Too Low;"
Figure 6C:
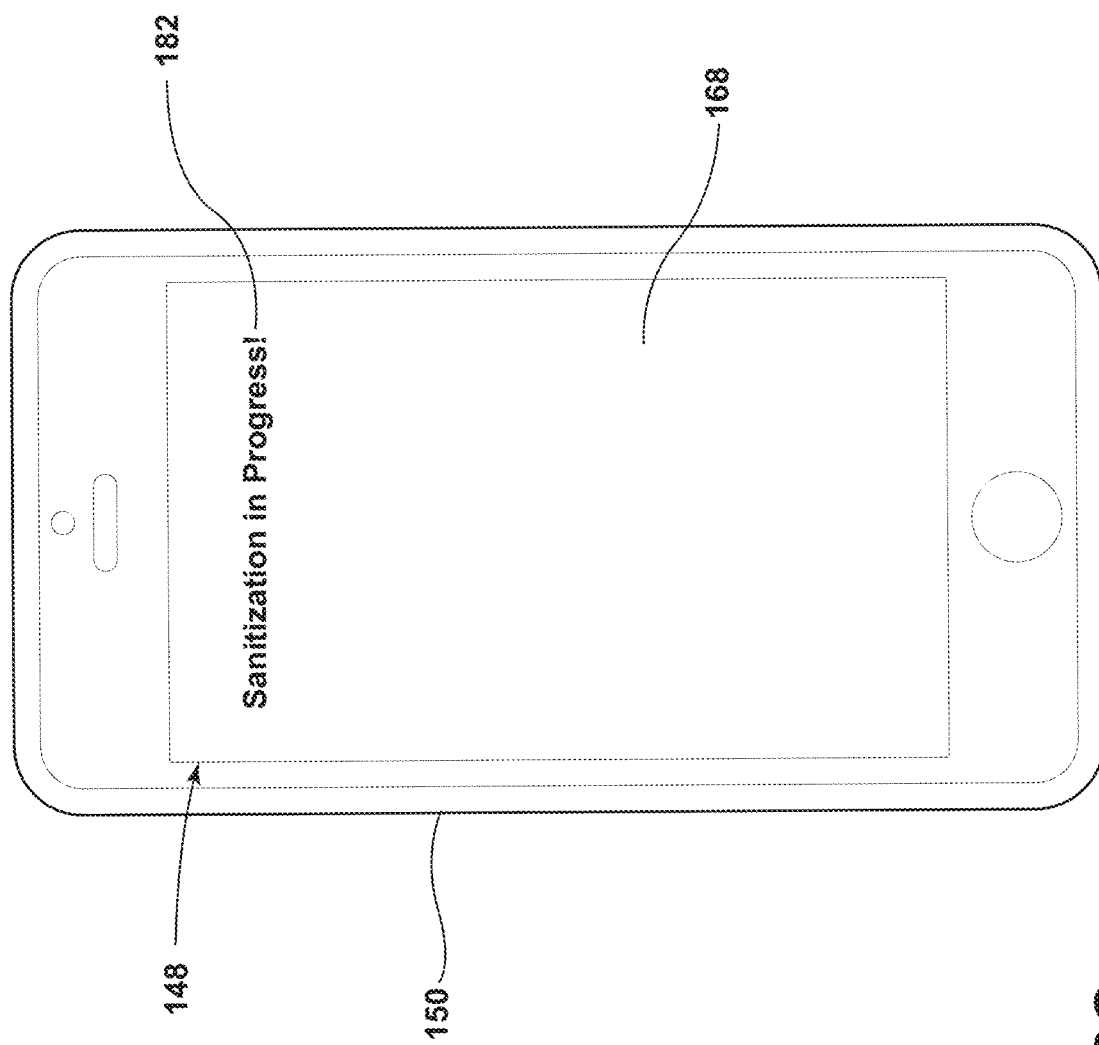
FIG. 6C is a view of the remote user interface of FIG. 5A, illustrating a communication from the vehicle display at the remote user interface to inform the person that the sanitization that the person had commanded via the remote user interface is in progress.

Referring now to FIG. 6, after the controller 146 performs the commanded sanitization, the controller 146 sends a communication 170 to the remote user interface 148 that the command has been executed. In other words, after the controller 146 causes (i) the heat source 20 to increase the temperature of the interior 12, (ii) the source 28 of the ultraviolet light 30 to emit the ultraviolet light into the interior 12, or both (i) and (ii), for a sufficient time to sanitize the interior 12, the controller 146 sends the communication 170 to the person 162 that the sanitization that the person 162 commanded via the remote user interface 148 has been executed. The person 162 thus knows that the interior 12 of the vehicle 10 has been sanitized. When the remote user interface 148 is the key fob 164, the communication 170 can be activation of a light source 165 on the key fob 164.

Figure 7:
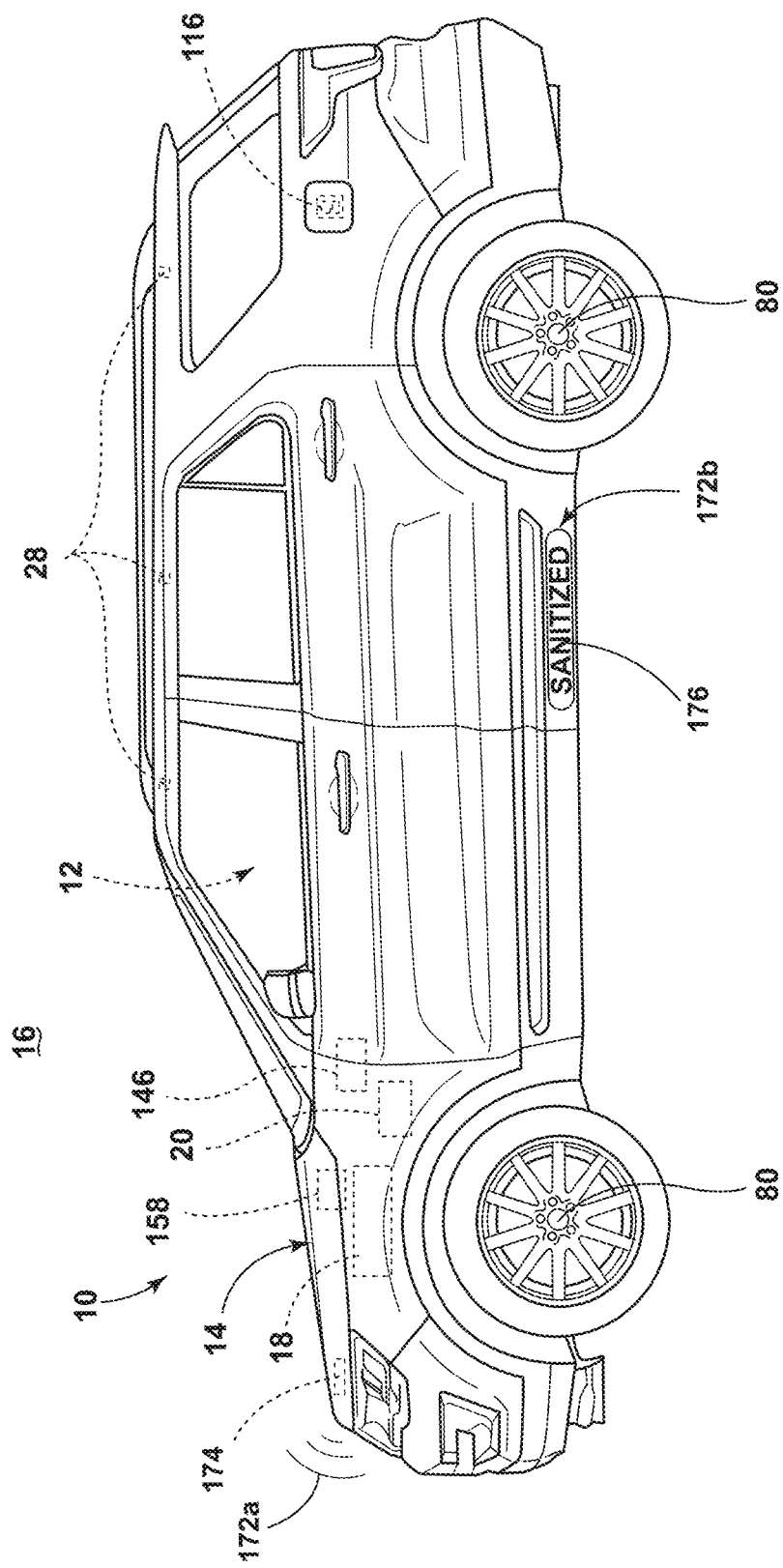
FIG. 7 is a side view of the vehicle of FIG. 1, illustrating the vehicle providing communications that are sensible from an external environment that the sanitization that the person commanded via the remote user interface has been completed, such as an audible noise from a horn of the vehicle or a visible display from a light source.

In addition, referring now additionally to FIG. 7, in embodiments, after the controller 146 performs the commanded sanitization, the controller 146 causes the vehicle 10 to send a communication 172 that is sensible from the external environment 16 that the sanitization has been completed. In other words, after the controller 146 causes (i) the heat source 20 to increase the temperature of the interior 12, (ii) the source 28 of the ultraviolet light 30 to emit the ultraviolet light 30 into the interior 12, or (iii) both (i) and (ii), for a sufficient time to sanitize the interior 12, the controller 146 causes the vehicle 10 to send the communication 172 that is sensible from the external environment 16 that the command to sanitize has been executed. In embodiments, the communication 172 is an audible noise 172a generated by a horn 174 of the vehicle 10. In embodiments, the communication 172 is a visible display 172b generated light source 176 of the vehicle 10 such as a lit "SANITIZED" or some other word or symbol to the external environment 16 that indicates that the command of sanitization has been executed. The light source 176 can be disposed at the charge port 116 in embodiments where the vehicle 10 has an electric motor 98 with the charging system 112 (e.g., FIGS. 3B and 3C). In embodiments, the communication 172 is an emission of visible light 172c into the interior 12 from a light source 178 (see FIG. 2) that indicates that the command of sanitization has been executed. The visible light 172c can be a color chosen to denote sanitization, such as blue, which provides an interesting visual effect when the external environment 16 is dark.

Figure 8:
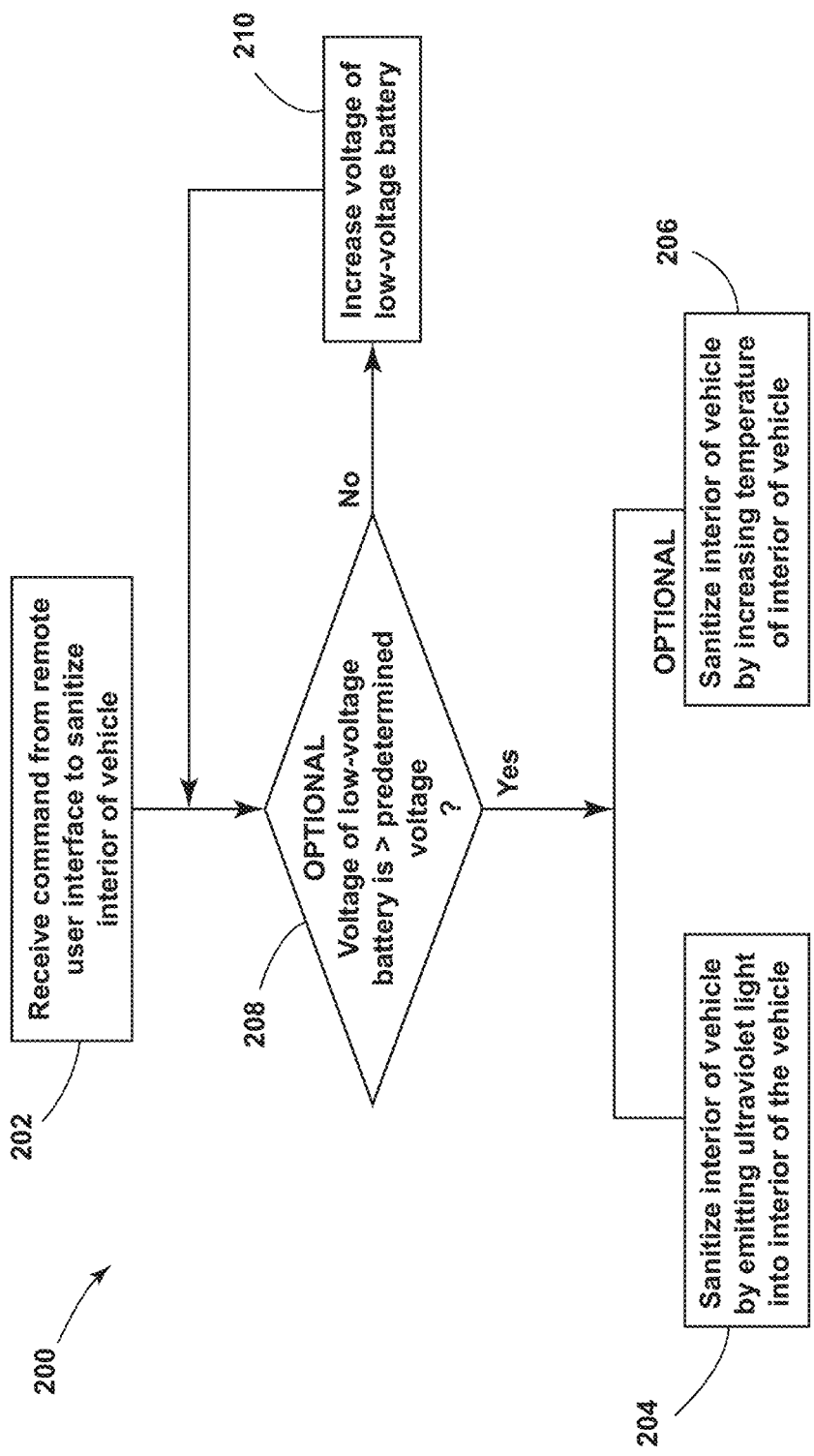
FIG. 8 is a schematic view of a method of sanitizing the interior of the vehicle of FIG. 1 using the remote user interface.

Referring now to FIG. 8, a method 200 of sanitizing the interior 12 of the vehicle 10 is disclosed. At a step 202, the method 200 includes receiving the command from the remote user interface 148 to sanitize the interior 12 of the vehicle 10. At a step 204, the method 200 further includes sanitizing the interior 12 of the vehicle 10 by emitting the ultraviolet light 30 into the interior 12 of the vehicle 10. In embodiments, at a step 206, the method 200 further includes sanitizing the interior 12 of the vehicle 10 by increasing the temperature of the interior 12 of the vehicle 10. The step 206 of increasing the temperature, if included, can occur simultaneously with the step of emitting the ultraviolet light 30.

In embodiments, the method 200 further includes, before the steps 204, 206 of sanitizing, a step 208 of determining whether the low-voltage battery 82 has a voltage that is greater than a predetermined voltage. If the determination of the step is "YES," the voltage of the low-voltage battery 82 is greater than the predetermined voltage, then the method 200 can proceed to one or more of the steps 204, 206 of sanitizing the interior 12 of the vehicle 10. If the determination of the step 208 is "NO," the voltage of the low-voltage battery 82 is not greater than the predetermined voltage, then the method 200 proceeds to a step 210 of increasing the voltage of the low-voltage battery 82. As discussed above, the combustion engine 40 can be started to increase the voltage of the battery, or the high-voltage battery 100 of the vehicle 10 can be connected to the external power source 114. The method 200 then proceeds back to the step 208 of determining whether the voltage of the low-voltage battery 82 is greater than the predetermined voltage.

Referring now to FIGS. 9A-9E, a method 300 of sanitizing the interior 12 of the vehicle 10 that includes the combustion engine 40 is herein described. At a step 302, the person 162 commands sanitization of the vehicle 10, such as via the remote user interface 148. The method 300 then proceeds to a step 304, where it is determined whether the person 162 specified the type of sanitization—that is, whether the person 162 commanded (as at FIG. 5A) sanitization via emission of the ultraviolet light 30 or via increasing the temperature of the interior 12, or both, or whether the person 162 commanded (as at FIG. 5B) just that the sanitization occur, leaving the determination of how sanitization will occur to the controller 146.

If the determination of the step 304 is "NO" (the person 162 did not specify), then the method 300 proceeds to a step 306. At the step 306, it is determined whether the temperature of the interior 12 of the vehicle 10 is greater than a predetermined temperature. If the determination is "YES," the temperature of the interior 12 of the vehicle 10 is greater than the predetermined temperature, then the method 300 proceeds to a step 308 (see FIG. 9B). At the step 308, the determination is made to proceed with sanitization via emission of the ultraviolet light 30 into the interior 12. The method 300 then proceeds to a step 310, where it is determined whether predetermined vehicle conditions are satisfied. If it is determined "NO," the vehicle conditions are not satisfied, then the method 300 proceeds to a step 312 where the determination is made (such as by the controller 146) to cancel the sanitization. The method 300 then proceeds to a step 314, where the person 162 is notified that the sanitization has been canceled. For example, the controller 146 can send via the communication module 158 a communication 180 to appear at the remote user interface 148 that the sanitization command has been canceled and, optionally, that the person 162 should make sure that the vehicle conditions have been satisfied. The method 300 then proceeds to a step 316, where the method 300 ends. The steps 312-316 are hereinafter referred to as a "Vehicle Conditions Subroutine." The vehicle conditions can include the conditions that the vehicle 10 is not moving, that the doors are closed and in a locked state, that the windowpanes are in a closed position, that the controller 146 determines from the signal from the occupancy sensor(s) 26 that no occupant is in the interior 12 of the vehicle 10. Various other sensors can provide signals to the controller 146 for the controller 146 to make the determination as to whether the vehicle conditions are satisfied.

If instead at the step 310, that "YES," the vehicle conditions are satisfied, then the method 300 proceeds to a step 318. At the step 318, it is determined whether the voltage of the low-voltage battery 82 is greater than a predetermined voltage. As described above, the controller 146 can make this determination based on the signal from the voltage sensor 108. If the determination is "YES," that the voltage of the low-voltage battery 82 is greater than the predetermined voltage, then the method 300 proceeds to a step 320. At the step 320, a communication 182 is sent to the person 162 that the sanitization that the person 162 had commanded is in progress (see FIG. 6C). The controller 146 can send the communication 182 through the communication module 158 to the remote user interface 148. The method 300 then proceeds to a step 322. At the step 322, the source 28 of the ultraviolet light 30 is activated and, thus, the source 28 emits the ultraviolet light 30 into the interior 12 of the vehicle 10, which sanitizes the interior 12. The controller 146 can activate the source 28 of the ultraviolet light 30. The method 300 then proceeds to a step 324 (see FIG. 9C), which is discussed further below.

If instead at the step 318, the determination is made that the voltage of the low-voltage battery 82 is not greater than the predetermined voltage, then the method 300 proceeds to a step 326. At the step 326, the determination is made as to whether the volume of the fuel 60 within the tank 64 of the vehicle 10 is greater than a predetermined volume. As discussed above, the controller 146 can make this determination considering the signal from the volume sensor 88. If the determination is "NO," the volume of the fuel 60 is not greater than the predetermined volume, then the method 300 proceeds to a step 328. At the step 328, the sanitization is canceled. The method 300 then proceeds to a step 330. At the step, the communication 180 is sent to the person 162 via the remote user interface 148 that the sanitization has been canceled and optionally with an explanation that the voltage of the low-voltage batter 82 and the volume of the fuel 60 is too low (see FIG. 6B). The method 300 then proceeds to a step 332, where the method 300 ends. The steps 328-332 are hereinafter collectively referred to as an "Insufficient Voltage and Volume of Fuel Subroutine."

If instead at the step 326, the determination is made that, "YES" the volume of the fuel 60 within the tank 64 of the vehicle 10 is greater than the predetermined volume, then the method 300 proceeds to a step 334. At the step 334, the combustion engine 40 of the vehicle 10 is started. The controller 146 can perform the step 334 by activating the pump 66 and the ignition system 74, among other things. The method 300 then proceeds to the step 320 mentioned above where the person 162 is notified that the sanitizing is in progress.

Figure 9A:
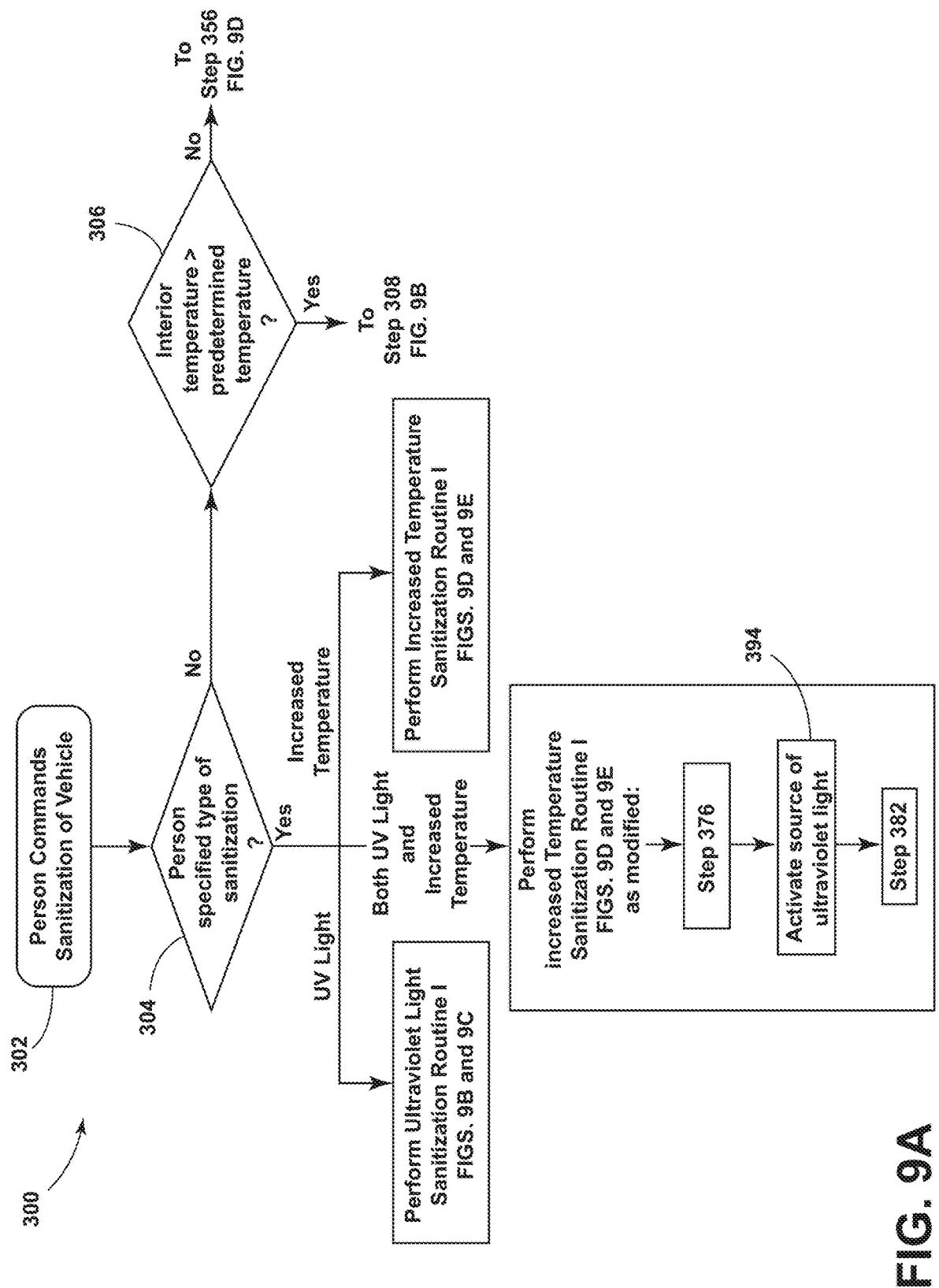
FIGS. 9A-9E are schematic views of another method of sanitizing the interior of the vehicle of FIG. 1 using the remote user interface, when the propulsion system of the vehicle is the combustion engine of FIG. 3A.
Figure 9B:
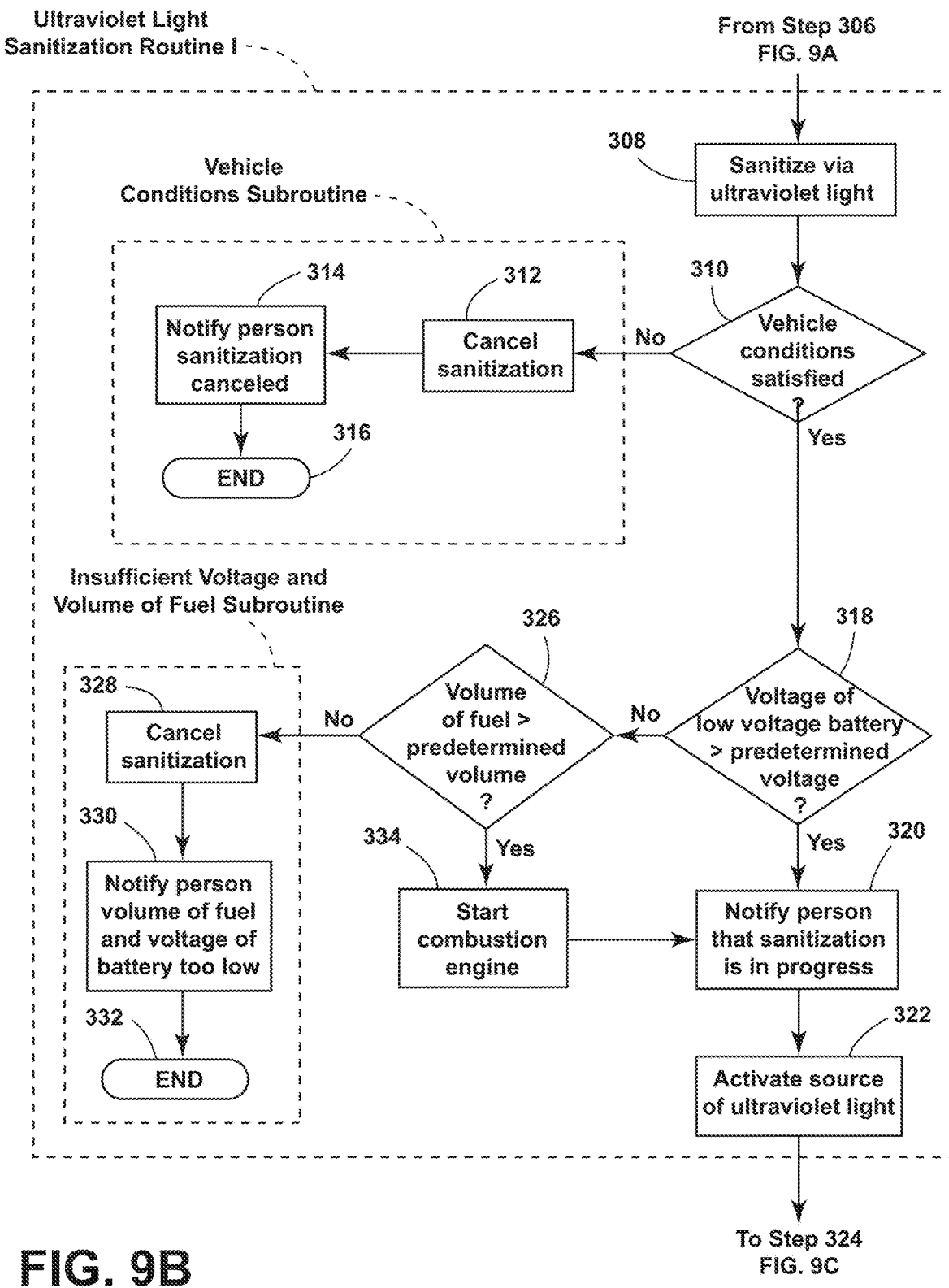
Figure 9C:
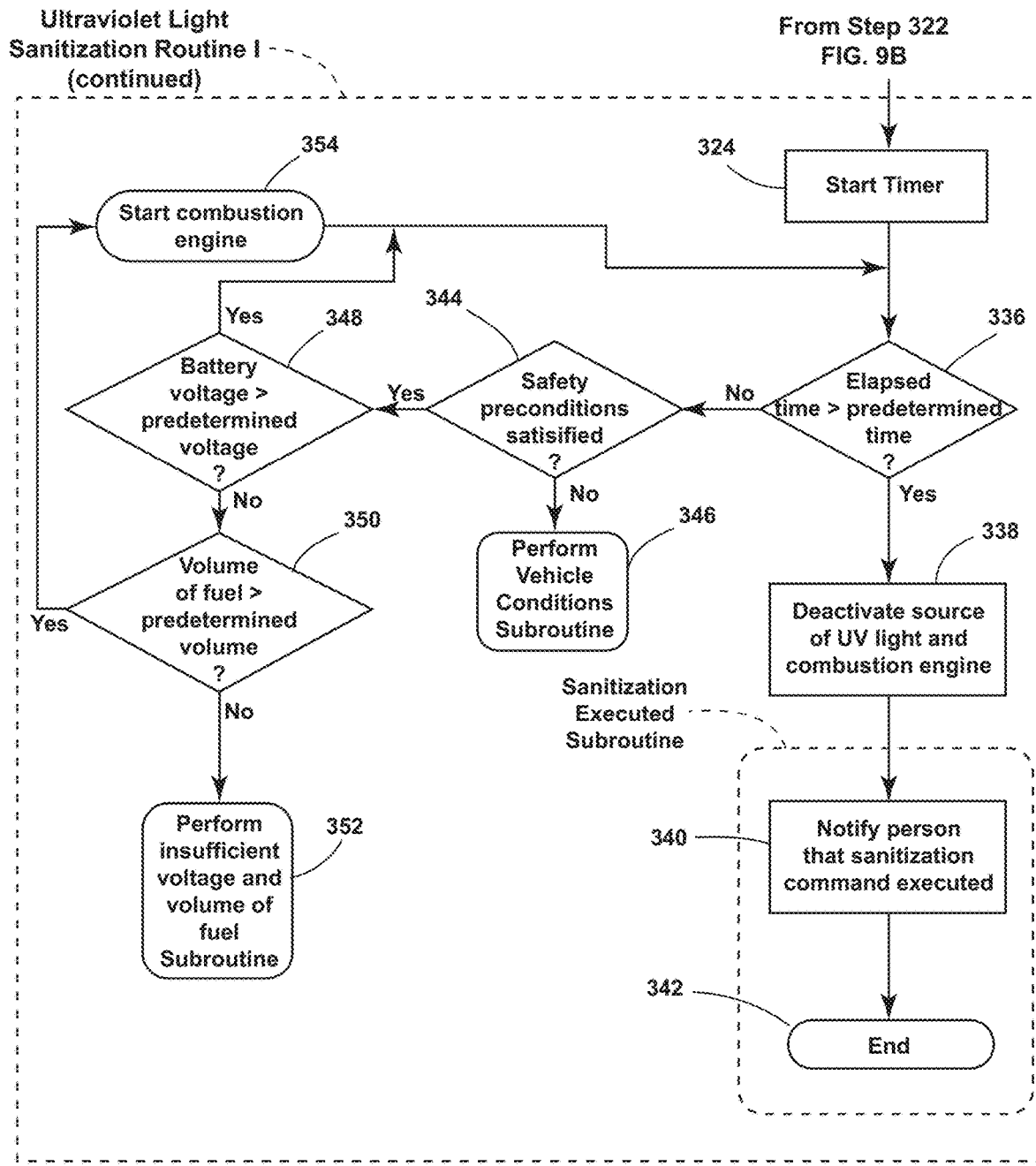

After activating the source 28 of the ultraviolet light 30 at the step 322, the method 300 proceeds to the step 324 (see FIG. 9C). At the step 324, a timer is started to measure the amount of time that the source 28 of the ultraviolet light 30 has been emitting the ultraviolet light 30. The controller 146 can perform the step 324. The method 300 then proceeds to a step 336, where it is determined whether the elapsed time that the source 28 of the ultraviolet light 30 has been emitting the ultraviolet light 30 is greater than a predetermined elapsed time. The predetermined elapsed time can be any period thought sufficient for the ultraviolet light 30 to sanitize the interior 12. In embodiments, the predetermined elapsed time is 5 minutes to 60 minutes. If it is determined that "YES," the elapsed time is greater than the predetermined elapsed time, then the method 300 continues to step 338. At the step 338, the source of ultraviolet light 30 and, if previously activated, the combustion engine 40 are deactivated, such as via the controller 146. The method 300 then proceeds to a step 340. At the step, the person 162 is sent the communication 170 that the sanitization command has been executed (see FIG. 6A). The controller 146 can send the communication 170 to the remote user interface 148. In addition, the controller 146 can cause the vehicle 10 to provide the communication 172 that is sensible from the external environment 16 that the command has been executed, as discussed above. The method 300 then proceeds to a step 342, where the method 300 ends. Steps 340 and 342 are hereinafter referred to as a "Sanitization Executed Subroutine."

If instead at the step 336, it is determined "NO", the elapsed time is not greater than the predetermined elapsed time, then the method 300 proceeds to a step 344. At the step 344, it is determined whether the vehicle conditions remain satisfied. If the determination is "NO," the vehicle conditions are not satisfied, then the method 300 proceeds to a step 346 where the source 28 of the ultraviolet light 30 and the combustion engine 40 (if activated) are deactivated and the Vehicle Conditions Subroutine is performed thus ending the method 300. If the determination is "YES," the vehicle conditions are satisfied, then the method 300 proceeds to a step 348. At the step 348, it is determined whether the voltage of the low-voltage battery 82 is greater than the predetermined voltage. If the determination is "YES," the voltage of the low-voltage battery 82 is still above the predetermined voltage, then the method 300 proceeds back to the step 336. If the determination is "NO," the voltage of the low-voltage battery 82 is not greater than the predetermined voltage, then the method 300 proceeds to a step 350. At the step 350, it is determined whether the volume of the fuel 60 is greater than the predetermined volume. If it is determined "NO," that the volume of the fuel 60 is not greater than the predetermined volume, then the method 300 proceeds to a step 352 where the source 28 of the ultraviolet light 30 and the combustion engine 40 (if activated) are deactivated and the Insufficient Voltage and Volume of Fuel Subroutine is executed thus ending the method. If it is determined "YES", the volume of the fuel 60 is greater than the predetermined volume, then the method 300 proceeds to a step 354. At the step 354, the combustion engine 40 is started if not already started. The method 300 then proceeds back to step 336 until it is determined that the elapsed time is greater than the predetermined elapsed time. The steps 308-354 are collectively hereinafter referred to as the "Ultraviolet Light Sanitization Routine I."

Figure 9D:
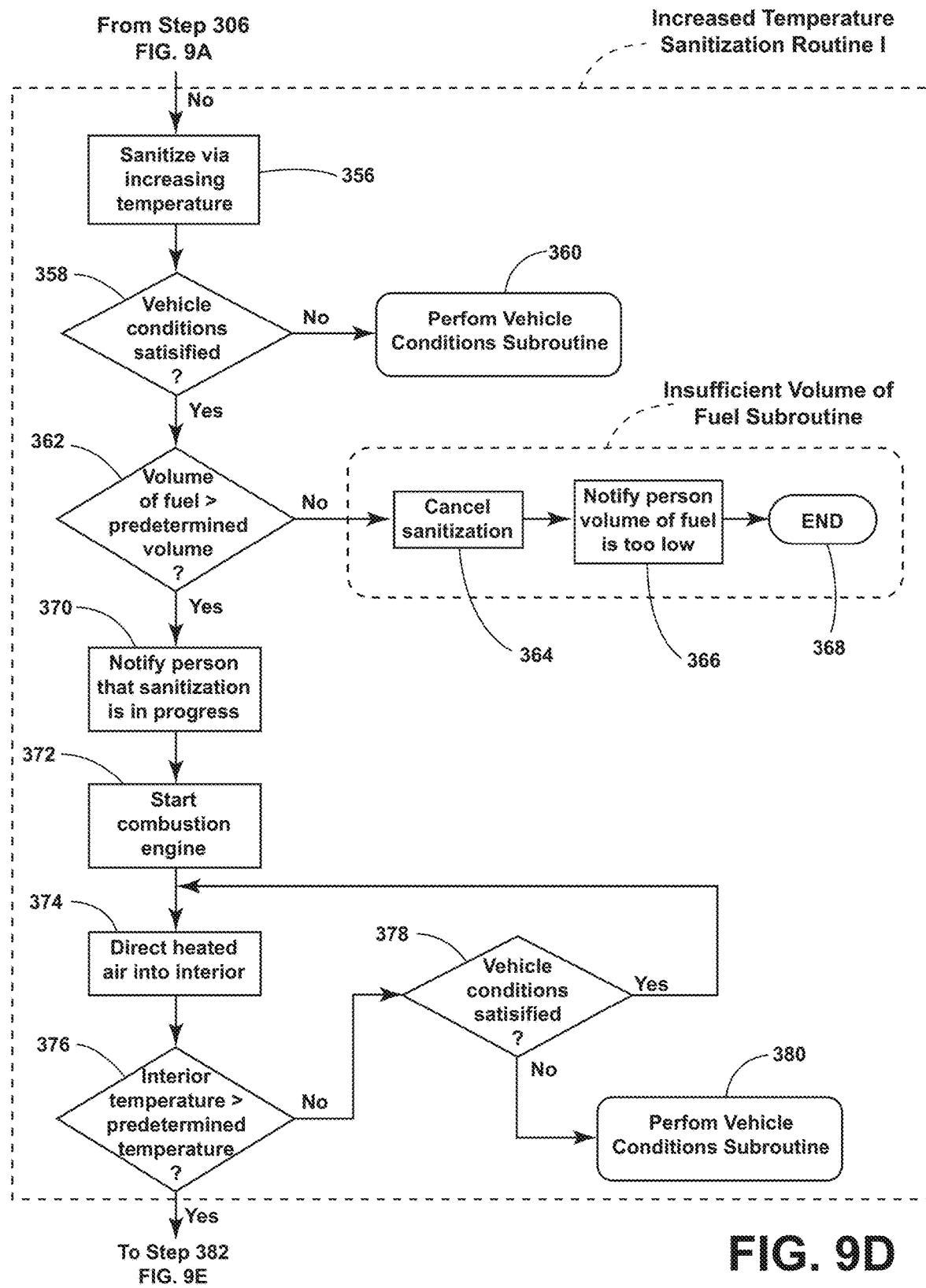
Figure 9E:
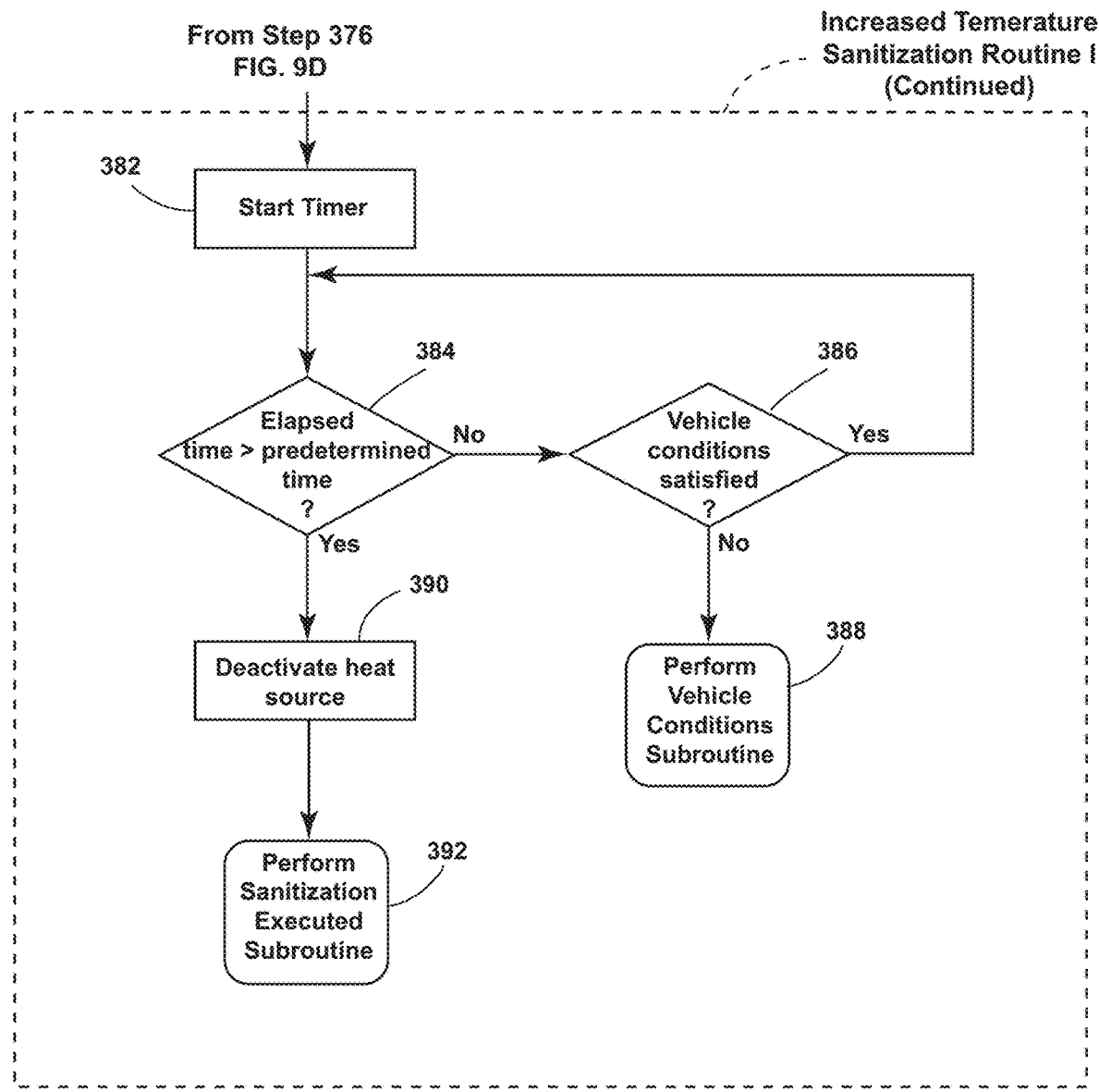

Returning now back to step 306 (FIG. 9A), if it is determined "NO," the temperature of the interior 12 is not greater than the predetermined temperature, then the method 300 proceeds to a step 356 (see FIG. 9D). At the step 356, it is determined to sanitize the interior 12 by increasing the temperature of the interior 12. The method 300 then proceeds to a step 358. At the step 358, the method 300 determines whether the vehicle 10 conditions are satisfied. If it is determined "NO," the vehicle conditions are not satisfied, then the method 300 proceeds to a step 360 where the Vehicle Conditions Subroutine (see FIG. 9B) is performed thus ending the method 300. If instead it is determined that "YES," the vehicle 10 conditions are satisfied, then the method 300 proceeds to a step 362. At the step 362, it is determined whether the volume of the fuel 60 is greater than a predetermined volume. This predetermined volume can be different than the predetermined volume of fuel 60 considered when increasing the voltage of the low-voltage battery 82 at the step 318. If at the step 362 it is determined "NO," that the volume of the fuel 60 is not greater than the predetermined volume, then the method 300 proceeds to a step 364 where it is determined to cancel the sanitization. The method 300 then proceeds to a step 366, where the person 162 is sent the communication 180 (see FIG. 6B) that the sanitization command has been canceled and optionally with the explanation that the volume of fuel 60 is too low. The method 300 then proceeds to a step 368 where the method 300 ends. The steps 364-368 are collectively hereinafter referred to as an "Insufficient Volume of Fuel Subroutine."

If instead at the step 362, it is determined that the volume of the fuel 60 is greater than the predetermined volume, then the method 300 proceeds to a step 370. At the step 370, the communication 182 is sent to the person 162 at the remote user interface 148 that the sanitization is in progress (see FIG. 6C). The method 300 then proceeds to a step 372, where the combustion engine 40 is started. The method 300 then proceeds to a step 374, where the heat source 20 is activated to increase the temperature of the interior 12 of the vehicle 10. Activating the heat source 20 can include passing the air 96 through the heat exchanger 90 to acquire heat that the combustion engine 40 generates and directing the air 96 into the interior 12, and well as activating the seat heating element(s) 182.

The method 300 then proceeds to a step 376. At the step 376, it is determined whether the temperature of the interior 12 is greater than a predetermined temperature. The predetermined temperature here can be different than the predetermined temperature utilized at the step 306 (see FIG. 9A). This predetermined temperature for the step 376 can be a higher temperature and sufficient to sanitize the vehicle 10. The controller 146 can make this determination using data from the temperature sensor 22. If the determination is "NO," the temperature of the interior 12 is not greater than the predetermined temperature, then the method 300 proceeds to a step 378. At the step 378, it is determined whether the vehicle conditions are satisfied. If it is determined "YES," the vehicle conditions are satisfied, then the method 300 returns to the step 374. If it is determined "NO," the vehicle conditions are not satisfied, then the method 300 proceeds to a step 380 where the combustion engine 40 is deactivated and the Vehicle Conditions Subroutine is performed thus ending the method 300. If instead at the step 376 it is determined "YES," the temperature of the interior 12 is greater than the predetermined temperature, then the method 300 proceeds to a step 382 (see FIG. 9E).

At the step 382, the timer is started to measure the amount of time that the temperature of the interior 12 has been greater than the predetermined temperature. The method 300 then proceeds to a step 384, where it is determined whether the amount of time (the elapsed time) that the temperature of the interior 12 has been greater than the predetermined temperature is greater than a predetermined elapsed time. If the determination is "NO," that the amount of time is not greater than the predetermined elapsed time, then the method 300 proceeds to a step 386. At the step 386, it is determined whether the vehicle 10 conditions remain satisfied. If the determination is "NO," the vehicle 10 conditions are not satisfied, then the method 300 proceeds to a step 388 where the heat source 20 is deactivated (including the combustion engine 40 and the seat heating element(s) 128) and the Vehicle Conditions Subroutine is performed thus ending the method 300. If the determination is "YES," the vehicle conditions are satisfied, then the method 300 proceeds back to the step 384. If at the step 384 if is determined that "YES," the amount of time is greater than the predetermined elapsed time, then the method 300 proceeds to a step 390. At the step 390, the heat source 20 is deactivated, which includes deactivating the combustion engine 40 and stopping flow of air 96 through the heat exchanger 90 and into the interior 12 and deactivating the seat heating element(s) 128, if activated. The method 300 then proceeds to a step 392 where the Sanitization Executed Subroutine is performed thus ending the method 300. The steps 356-392 are hereinafter referred to as the "Increased Temperature Sanitization Routine I."

Referring back to FIG. 9A, if instead at the step 304 it is determined that the person 162 did specify the type of sanitization, then if the person 162 chose sanitization via emission of the ultraviolet light 30, then the method 300 proceeds to perform the Ultraviolet Light Sanitization Routine I described above and then the method 300 ends. If the person 162 chose sanitization via increasing the temperature of the interior 12, then the method 300 proceeds to perform the Increased Temperature Sanitization Routine I described above and then the method 300 ends.

If the person 162 chose sanitization via both emission of the ultraviolet light 30 and increasing the temperature of the interior 12, then the method 300 proceeds to perform the Increased Temperature Sanitization Routine I described above, with the exception that after step 376 where it is determined "YES," the temperature of the interior 12 is greater than the predetermined temperature, and before step 382 where the timer is started, a step 394 is performed where the source 28 of the ultraviolet light 30 is activated. Further, at step 390, the source 28 is additionally deactivated.

Referring now to FIGS. 10A-10E, a method 400 of sanitizing the interior 12 of the vehicle 10 that includes the electric motor 98 is herein described. At a step 402, the method 400 begins with the person 162 commanding sanitization of the vehicle 10, such as via the remote user interface 148. The method 400 then proceeds to a step 404, where it is determined whether the person 162 specified the type of sanitization—that is, whether the person 162 commanded (as at FIG. 5A) sanitization via emission of the ultraviolet light 30 or via increasing the temperature of the interior 12, or both, or whether the person 162 commanded just that the sanitization occur, leaving the determination of how sanitization will occur to the controller 146.

If it is determined at step 404 that "NO" (the person 162 did not specify), then the method 400 proceeds to a step 406. At the step 406, it is determined whether the temperature of the interior 12 of the vehicle 10 is greater than a predetermined temperature. If the determination is "YES," then the method 400 proceeds to a step 408 (see FIG. 10B). At the step 408, the determination is made to proceed with sanitization via emission of the ultraviolet light 30 into the interior 12. The method 400 then proceeds to a step 410, where a determination is made as to whether the vehicle conditions are satisfied. If the response to the determination is "NO," then the method 400 proceeds to a step 412 where the Vehicle Conditions Subroutine is performed thus ending the method 400.

If instead at the step 410, it is determined "YES," the vehicle 10 conditions are satisfied, then the method 400 proceeds to a step 414. At the step 414, it is determined whether the voltage of the low-voltage battery 82 of the vehicle 10 is greater than the predetermined voltage. As described above, the controller 146 can make this determination based on the signal from the voltage sensor 84. If the determination is "YES," that is that the voltage of the low-voltage battery 82 is greater than the predetermined voltage, then the method 400 proceeds to a step 416. At the step 416, the communication 182 is sent to the person 162 that the sanitization that the person 162 had commanded is in progress (see FIG. 6C). The method 400 then proceeds to a step 418. At the step 418, the source 28 of the ultraviolet light 30 is activated and, thus, the source 28 emits the ultraviolet light 30 into the interior 12 of the vehicle 10, which sanitizes the interior 12. The method 400 then proceeds to a step 420 (see FIG. 10C), which is discussed further below.

If instead at the step 414, the determination is "NO," the voltage of the low-voltage battery 82 is not greater than the predetermined voltage, then the method 400 proceeds to a step 422. At the step 422, the determination is made as to whether the high-voltage battery 100 of the vehicle 10 is connected to the external power source 114. If the determination is "YES," the high-voltage battery 100 of the vehicle 10 is connected to the external power source 114, then the method 400 proceeds to a step 424. At the step 424, the DC-to-DC converter 122 is enabled. As discussed above, the DC-to-DC converter 122 steps down the voltage from the high-voltage battery 100 to a voltage more suitable for the source 28 of the ultraviolet light 30. The method 400 then proceeds back to the step 416, and the source 28 of the ultraviolet light 30 is powered with the high-voltage battery 100 source, while the external power source 114 is charging the high-voltage battery 100 source, instead of the low-voltage battery 82 source powering the source 28 of the ultraviolet light 30.

If instead at the step 422 the determination is made that "NO," the high-voltage battery 100 of the vehicle 10 is not connected to the external power source 114, then the method 400 proceeds to a step 426. At the step 426, it is determined whether the state-of-charge of the high-voltage battery 100 is greater than a predetermined state-of-charge. If is determined "NO," then the method proceeds to a step 428. At step 428, the determination is made to cancel the sanitization. The method then proceeds to a step 430. At the step 430, the communication 180 is sent to the person 162 at the remote user interface 148 that the sanitization has been canceled optionally with the explanation that the state-of-charge of the high-voltage battery 100 is too low. The method 400 then proceeds to a step 432 where the method 400 ends. The steps 428-432 are collectively hereinafter referred to as an "Insufficient State-of-Charge Subroutine."

Figure 10A:
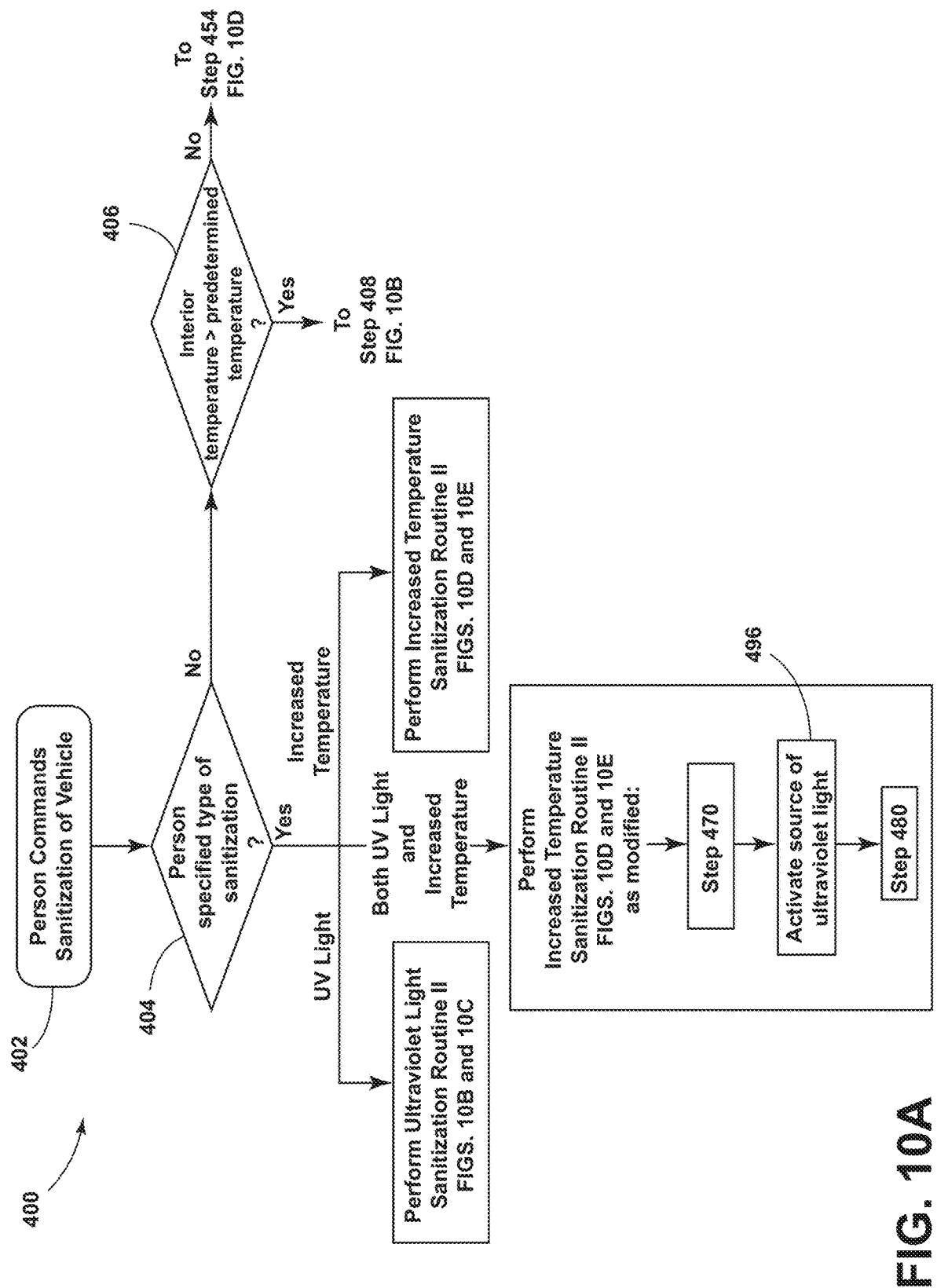
FIGS. 10A-10E are schematic views of another method of sanitizing the interior of the vehicle of FIG. 1 using the remote user interface, when the propulsion system of the vehicle is the electric motor of FIG. 3B.
Figure 10B:
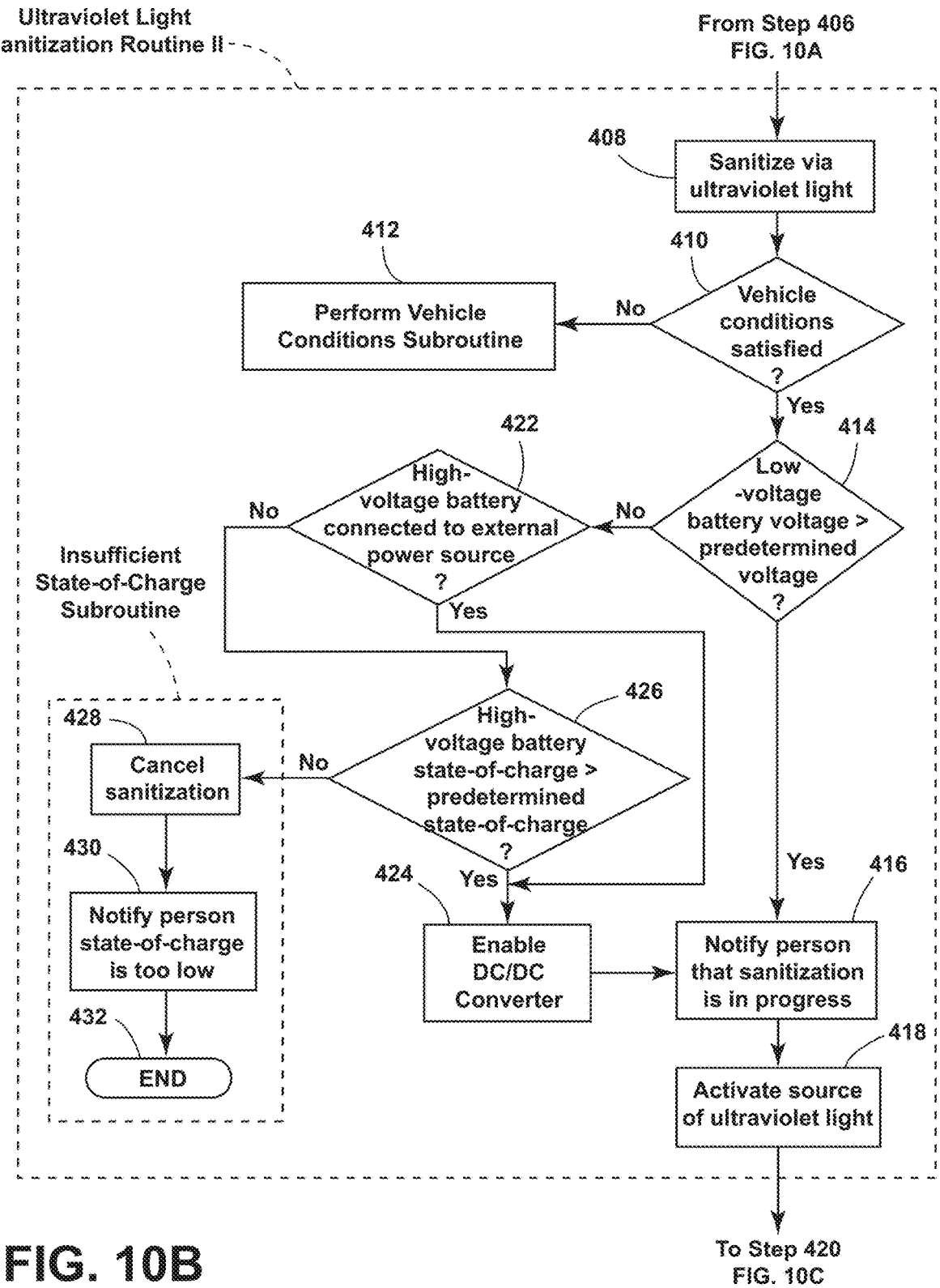
Figure 10C:
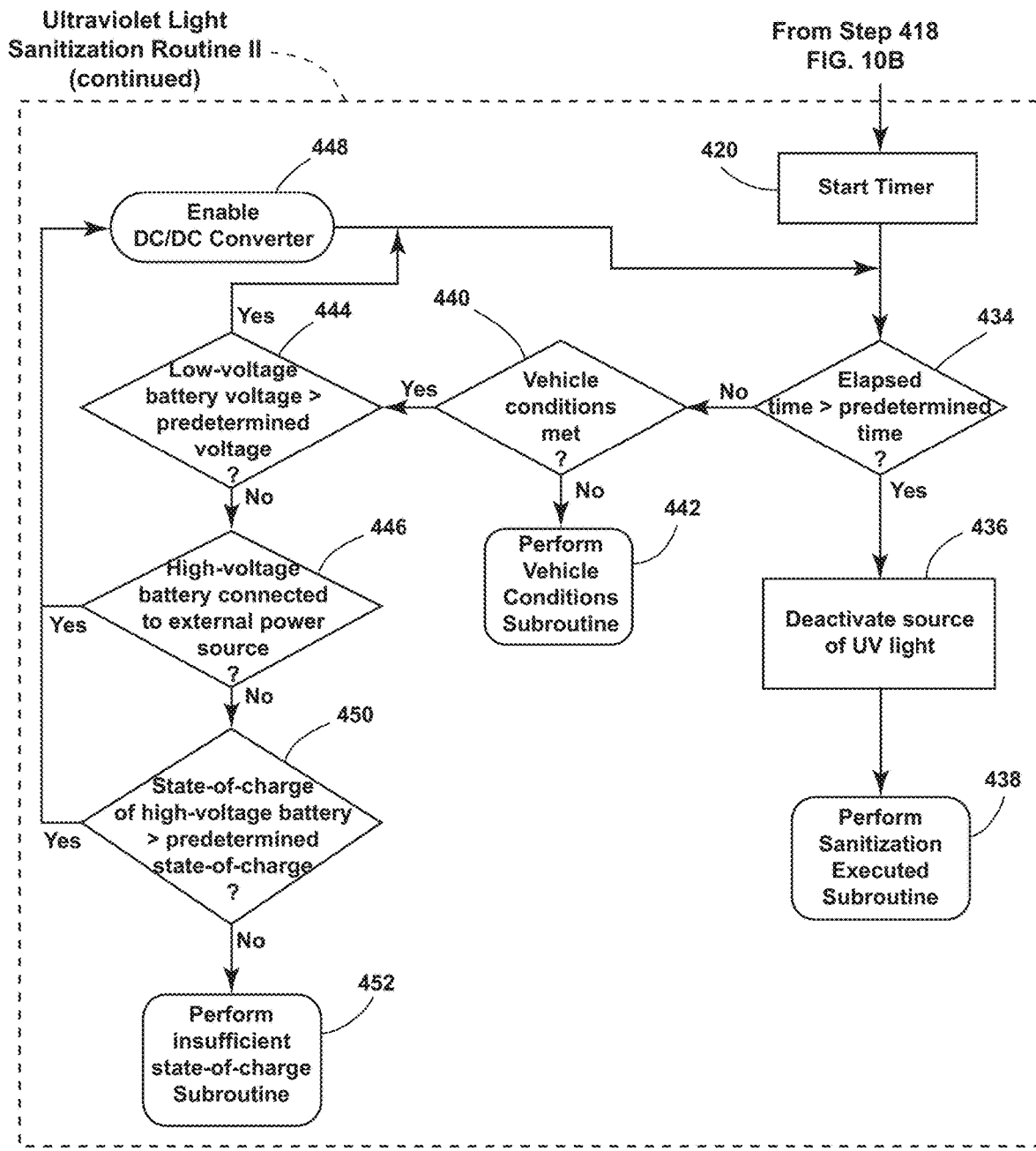

After activating the source 28 of the ultraviolet light 30 at the step 418, the method 400 proceeds to the step 420 (see FIG. 10C). At the step 420, a timer is started to measure the amount of time that the source 28 of the ultraviolet light 30 has been emitting the ultraviolet light 30. The method 400 then proceeds to a step 434, where it is determined whether the elapsed time that the source 28 of the ultraviolet light 30 has been emitting the ultraviolet light 30 is greater than a predetermined elapsed time. If it is determined "YES," the elapsed time is greater than the predetermined elapsed time, then the method 400 continues to a step 436. At the step 436, the source 28 of the ultraviolet light 30 is deactivated. The method 400 then proceeds to a step 438 where the Sanitization Executed Subroutine is performed thus ending the method 400.

If instead at the step 434, it is determined "NO", the elapsed time is not greater than the predetermined elapsed time, then the method 400 proceeds to a step 440. At the step 440, it is determined whether the vehicle conditions remain satisfied. If the determination is "NO," the vehicle conditions are not satisfied, then the method 400 proceeds to a step 442. At the step 442, the source 28 of the ultraviolet light 30 is deactivated and the Vehicle Conditions Subroutine is performed thus ending the method 400. If the determination is "YES," the vehicle conditions are satisfied, then the method 400 proceeds to a step 444. At the step 444, it is determined whether the voltage of the low-voltage battery 82 is still above the predetermined voltage. If the determination is "YES," the voltage of the low-voltage battery 82 is still above the predetermined voltage, then the method 400 proceeds back to the step 434. If the determination is "NO," the voltage of the low-voltage battery 82 is not above the predetermined voltage, then the method 400 proceeds to a step 446. At the step 446, it is determined whether the high-voltage battery 100 is connected to the external power source 114. If the determination is "YES," the high-voltage battery 100 is connected to the external power source 114, then the method 400 proceeds to a step 448. At the step, the DC-to-DC converter 122 is enabled, and the method 400 proceeds back to the step 434 until it is determined that the elapsed time is greater than the predetermined elapsed time. If instead at the step 446 the determination is "NO," the high-voltage battery 100 is not connected to the external power source 114, then the method 400 proceeds to a step 450. At the step 450, it is determined whether the state-of-charge of the high-voltage battery 100 is greater than the predetermined state-of-charge. If the determination is "YES," the state-of-charge of the high-voltage battery 100 is greater than the predetermined state-of-charge, then the method 400 proceeds to the step 448 described above and the high-voltage battery 100 powers the source 28 of the ultraviolet light 30. If the determination is "NO," the state-of-charge of the high-voltage battery 100 is not greater than the predetermined state-of-charge, then the method 400 proceeds to a step 452. At the step 452, the source 28 of the ultraviolet light 30 is deactivated and the Insufficient State-of-Charge Subroutine is performed and the method 400 ends. The steps 408-452 are collectively hereinafter referred to as the "Ultraviolet Light Sanitization Routine II."

Figure 10D:
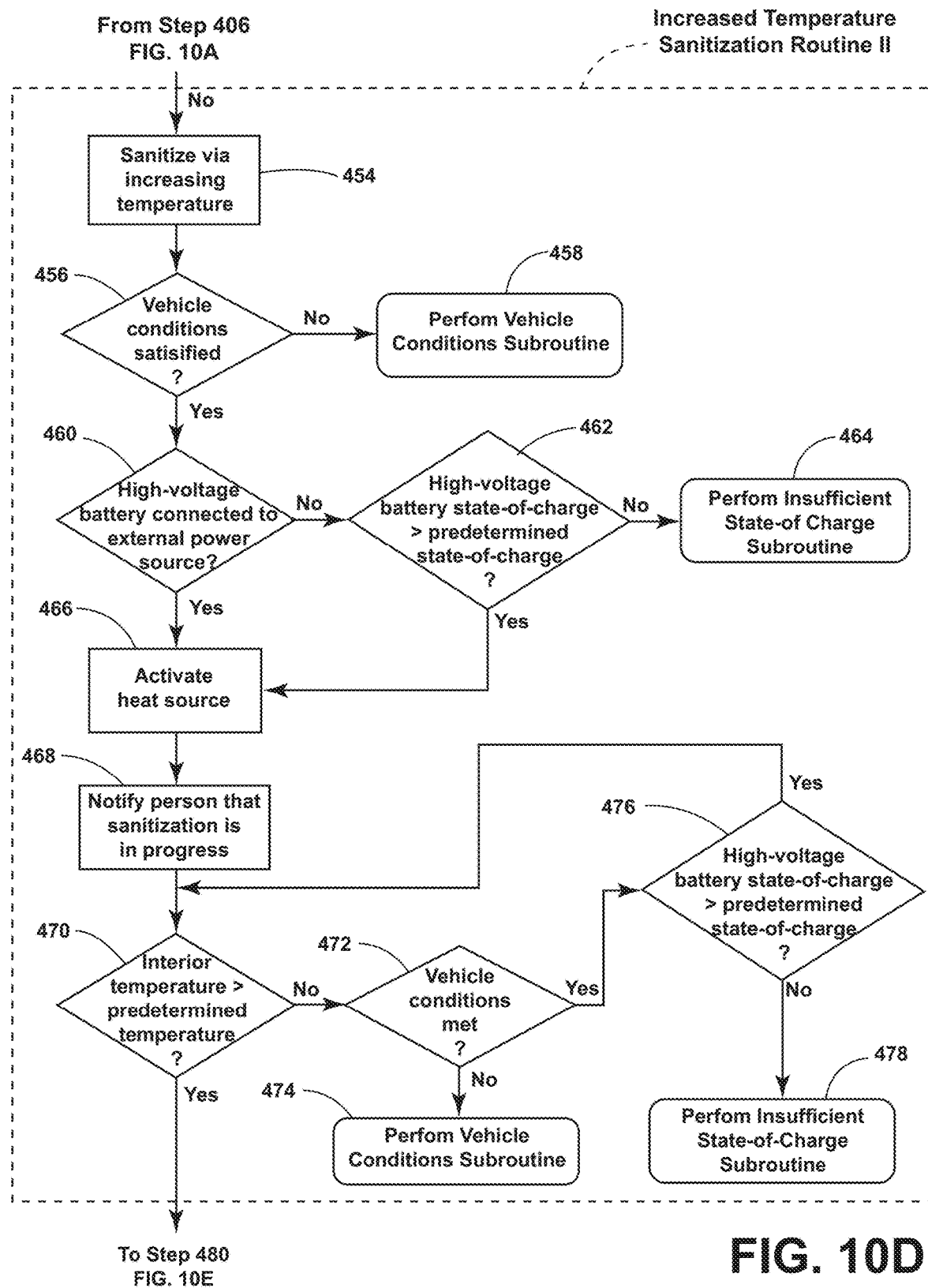
Figure 10E:
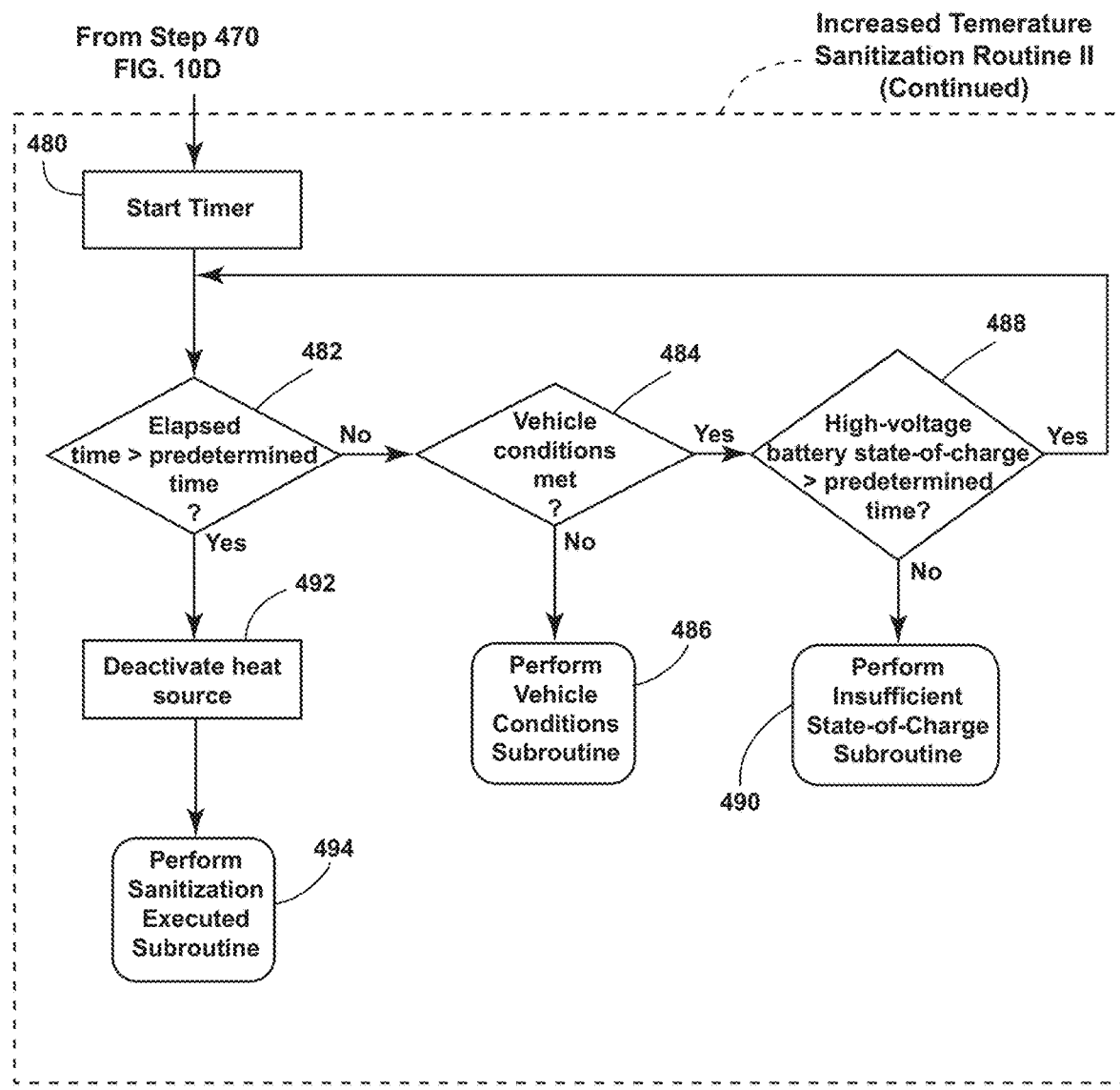

Returning now back to step 406 (see FIG. 10A), if it is determined "NO," the temperature of the interior 12 is not above the predetermined temperature, then the method 400 proceeds to a step 454 (see FIG. 10D). At the step 454, it is determined to sanitize the interior 12 by increasing the temperature of the interior 12. The method 400 then proceeds to a step 456. At the step 456, the method 400 determines whether the vehicle 10 conditions are satisfied. If it is determined that "NO," the vehicle conditions are not satisfied, then the method 400 proceeds to a step 458 where the Vehicle Conditions Subroutine is performed thus ending the method 400. If instead it is determined that "YES," the vehicle 10 conditions are satisfied, then the method 400 proceeds to a step 460. At the step 460, it is determined whether high-voltage battery 100 is connected to the external power source 114. If it is determined "NO," the high-voltage battery 100 is not connected to the external power source 114, then the method 400 proceeds to a step 462. At the step 462, it is determined whether the state-of-charge of the high-voltage battery 100 is greater than a predetermined state-of-charge. The predetermined state-of-charge for this step can be different (e.g., greater than) the predetermined state-of-charge for powering the source 28 of the ultraviolet light 30 at the step 450. If it is determined "NO," the state-of-charge of the high-voltage battery 100 is not greater than the predetermined state-of-charge, then the method 400 proceeds to a step 464 where the Insufficient State-of-Charge Subroutine is performed thus ending the method 400.

If instead at the step 464 it is determined "YES," the state-of-charge of the high-voltage battery 100 is greater than the predetermined state-of-charge, then the method 400 proceeds to a step 466. Likewise, if instead at the step 460 it is determined "YES," the high-voltage battery 100 is connected to the external power source 114, the method 400 proceeds to the step 466. At the step 466, the heat source 20 of the vehicle 10 is activated. In embodiments, the heat source 20 has a positive temperature coefficient, as discussed above, and the heat source 20 can heat the air 96 directed into the interior 12. Activation of the heat source 20 can further include the seat heating element(s) 128 disposed in the seating assemblies 24. The method 400 then proceeds to a step 468, where the communication 182 (see FIG. 6C) is sent to the person 162 at the remote user interface 148 that the sanitization is in progress.

The method 400 then proceeds to a step 470. At the step 470, it is determined whether the temperature of the interior 12 of the vehicle 10 is greater than a predetermined temperature (such as a temperature sufficient to sanitize the interior 12). If it is determined "NO," the temperature of the interior 12 is not greater than the predetermined temperature, then the method 400 proceeds to a step 472. At the step 472, it is determined whether the vehicle 10 conditions are satisfied. If it is determined "NO," the vehicle 10 conditions are not satisfied, then the method 400 proceeds to a step 474 where the heat source 20 is deactivated and the Vehicle Conditions Subroutine is performed thus ending the method 400. If it is determined "YES," the vehicle 10 conditions are satisfied, then the method 400 proceeds to a step 476. At the step 476, it is determined whether the state-of-charge of the high-voltage battery 100 is greater than the predetermined state-of-charge. If it is determined "YES," the state-of-charge of the high-voltage battery 100 is greater than the predetermined state-of-charge, then the method 400 proceeds back to the step 470. If instead it is determined "NO," the state-of-charge of the high-voltage battery 100 is not greater than the predetermined state-of-charge, then the method 400 proceeds to a step 478 where the heat source 20 is deactivated and the Insufficient State-of-Charge Subroutine is performed thus ending the method 400. If instead at the step 470 it is determined "YES," the temperature of the interior 12 is greater than the predetermined temperature, then the method 400 proceeds to a step 480 (see FIG. 10E).

At the step 480, the timer is started to measure the amount of time that the temperature of the interior 12 has been greater than the predetermined temperature. The method 400 then proceeds to a step 482, where it is determined whether the amount of time (the elapsed time) that the temperature of the interior 12 has been greater than the predetermined temperature is greater than a predetermined elapsed time. If the determination is "NO," that the amount of time is not greater than the predetermined elapsed time, then the method 400 proceeds to a step 484. At the step 484, it is determined whether the vehicle conditions remain satisfied. If the determination is "NO," the vehicle 10 conditions are not satisfied, then the method 400 proceeds to a step 486 where the heat source 20 is deactivated the Vehicle Conditions Subroutine is performed thus ending the method 400. If the determination is "YES," the vehicle 10 conditions are satisfied, then the method 400 proceeds to a step 488. At the step 488, it is determined whether the state-of-charge of the high-voltage battery 100 is greater than the predetermined state-of-charge. If it is determined "NO," the state-of-charge of the high-voltage battery 100 is not greater than the predetermined state-of-charge, then the method 400 proceeds to a step 490 where the heat source 20 is deactivated and the Insufficient State-of-Charge Subroutine is performed thus ending the method 400. If it is determined "YES," the state-of-charge of the high-voltage battery 100 is greater than the predetermined state-of-charge, then the method 400 proceeds back to the step 482.

If at step 482 if is determined that "YES," the amount of time is greater than the predetermined elapsed time, then the method 400 proceeds to a step 492. At the step 492, the heat source 20 is deactivated, which includes deactivating the heating element 126 and the seat heating element(s) 128 and stopping flow of air 96 into the interior 12. The method 400 then proceeds to a step 494 where the Sanitization Executed Subroutine (see FIG. 9C) is performed thus ending the method 400. The steps 454-494 are collectively hereinafter referred to as the "Increased Temperature Sanitization Routine II."

Referring back to FIG. 10A, if instead at the step 404 it is determined "YES," the person 162 did specify the type of sanitization, then if the person 162 chose sanitization via emission of the ultraviolet light 30, then the method 400 proceeds to perform the Ultraviolet Light Sanitization Routine II thus ending the method 400. If the person 162 chose sanitization via increasing the temperature of the interior 12, then the method 400 proceeds to perform the Increased Temperature Sanitization Routine II described above and then the method 400 ends.

If the person 162 chose sanitization via both emission of the ultraviolet light 30 and increasing the temperature of the interior 12, then the method 400 proceeds to perform the Increased Temperature Sanitization Routine II described above, with the exception that after step 470 where it is determined "YES," the temperature of the interior 12 is greater than the predetermined temperature, and before step 480 where the timer is started, a step 496 is performed where the source 28 of the ultraviolet light 30 is activated. Further at a step 492, the source 28 is additionally deactivated.

Referring now to FIGS. 11A-11H, a method 500 of sanitizing the interior 12 of the vehicle 10 that includes the combustion engine 40 and the electric motor 98 is herein described. At a step 502, the method 500 begins with the person 162 commanding sanitization of the vehicle 10, such as via the remote user interface 148. The method 500 then proceeds to a step 504, where it is determined whether the person 162 specified the type of sanitization—that is, whether the person 162 commanded (as at FIG. 5A) sanitization via emission of the ultraviolet light 30 or via increasing the temperature of the interior 12, or both, or whether the person 162 commanded (as at FIG. 5B) just that the sanitization occur, leaving the determination of how sanitization will occur to the controller 146.

If the determination of the step 504 is "NO" (the person 162 did not specify), then the method 500 proceeds to a step 506. At the step 506, it is determined whether the temperature of the interior 12 of the vehicle 10 is greater than a predetermined temperature. If the determination is "YES," then the method 500 proceeds to a step 508 (see FIG. 11B). At the step 508, the determination is made to proceed with sanitization via emission of the ultraviolet light 30 into the interior 12. The method 500 then proceeds to a step 510, where a determination as to whether the vehicle 10 conditions are satisfied. If the response to the determination is "NO," then the method 500 proceeds to a step 512 where the Vehicle Conditions Subroutine (see FIG. 9B) is performed and the method 500 ends.

If instead at the step 510, it is determined "YES," the vehicle 10 conditions are satisfied, then the method 500 proceeds to a step 514. At the step 514, it is determined whether the voltage of the low-voltage battery 82 of the vehicle 10 is greater than the predetermined voltage. If the determination is "YES," the voltage of the low-voltage battery 82 is greater than the predetermined voltage, then the method 500 proceeds to a step 516. At the step 516, the communication 182 is sent to the person 162 that the sanitization that the person 162 had commanded is in progress (see FIG. 6C). The method 500 then proceeds to a step 518. At the step 518, the source 28 of the ultraviolet light 30 is activated and, thus, the source 28 emits the ultraviolet light 30 into the interior 12 of the vehicle 10, which sanitizes the interior 12. The method 500 then proceeds to a step 520 (see FIG. 11C), which is discussed further below.

If instead at the step 514, the determination is made that the voltage of the low-voltage battery 82 is below the predetermined voltage, then the method 500 proceeds to a step 522. At the step 522, the determination is made as to whether the high-voltage battery 100 of the vehicle 10 is connected to the external power source 114. If the determination is "YES," the high-voltage battery 100 of the vehicle 10 is connected to the external power source 114, then the method 500 proceeds to a step 524. At the step 524, the DC-to-DC converter 122 is enabled. The method 500 then proceeds back to the step 516, and the source 28 of the ultraviolet light 30 is powered with the high-voltage battery 100, while the external power source 114 is charging the high-voltage battery 100, instead of the low-voltage battery 82.

If instead at the step 522 the determination is made that "NO," the high-voltage battery 100 of the vehicle 10 is not connected to the external power source 114, then the method 500 proceeds to a step 526. At the step 526, it is determined whether the state-of-charge of the high-voltage battery 100 is greater than a predetermined state-of-charge. If it is determined "YES," the state-of-charge of the high-voltage battery 100 is greater than the predetermined state-of-charge, then the method 500 proceeds to the step 524. If it is determined "NO," the state-of-charge of the high-voltage battery 100 is not greater than the predetermined state-of-charge, then the method 500 proceeds to a step 528. At the step 528, it is determined whether the volume of fuel 60 within the tank 64 is greater than a predetermined volume. If it is determined "NO," the volume of fuel 60 within the tank 64 is not greater than the predetermined volume, then the method 500 proceeds to a step 530 where the Insufficient Fuel Subroutine is performed thus ending the method 500. If it is determined "YES," the volume of fuel 60 within the tank 64 is greater than the predetermined volume, then the method 500 proceeds to a step 532. At the step, the combustion engine 40 of the vehicle 10 is activated and the method 500 proceeds back to the step 524 with the combustion engine 40 providing the electrical power to operate the source 28 of the ultraviolet light 30.

Figure 11B:
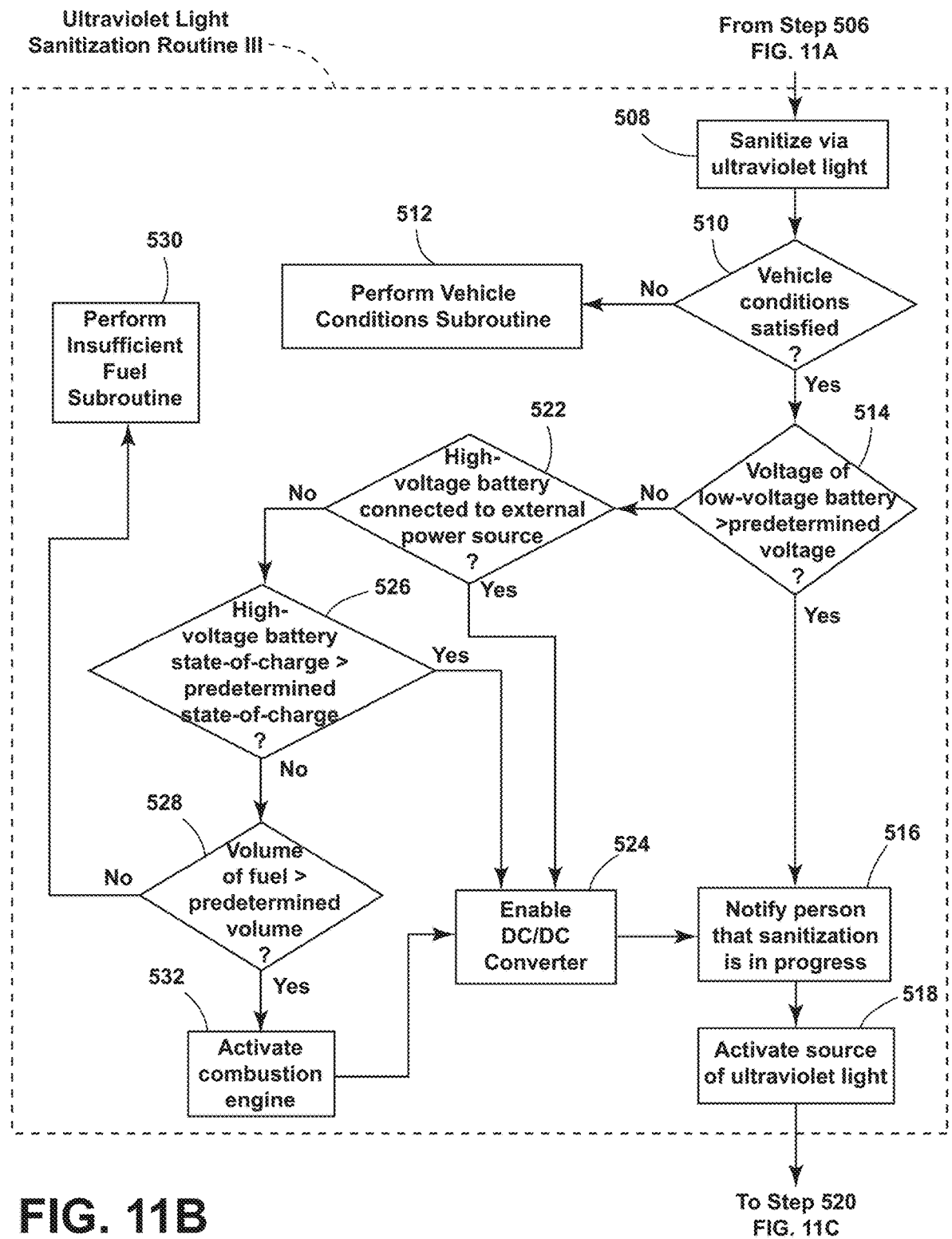
Figure 11C:
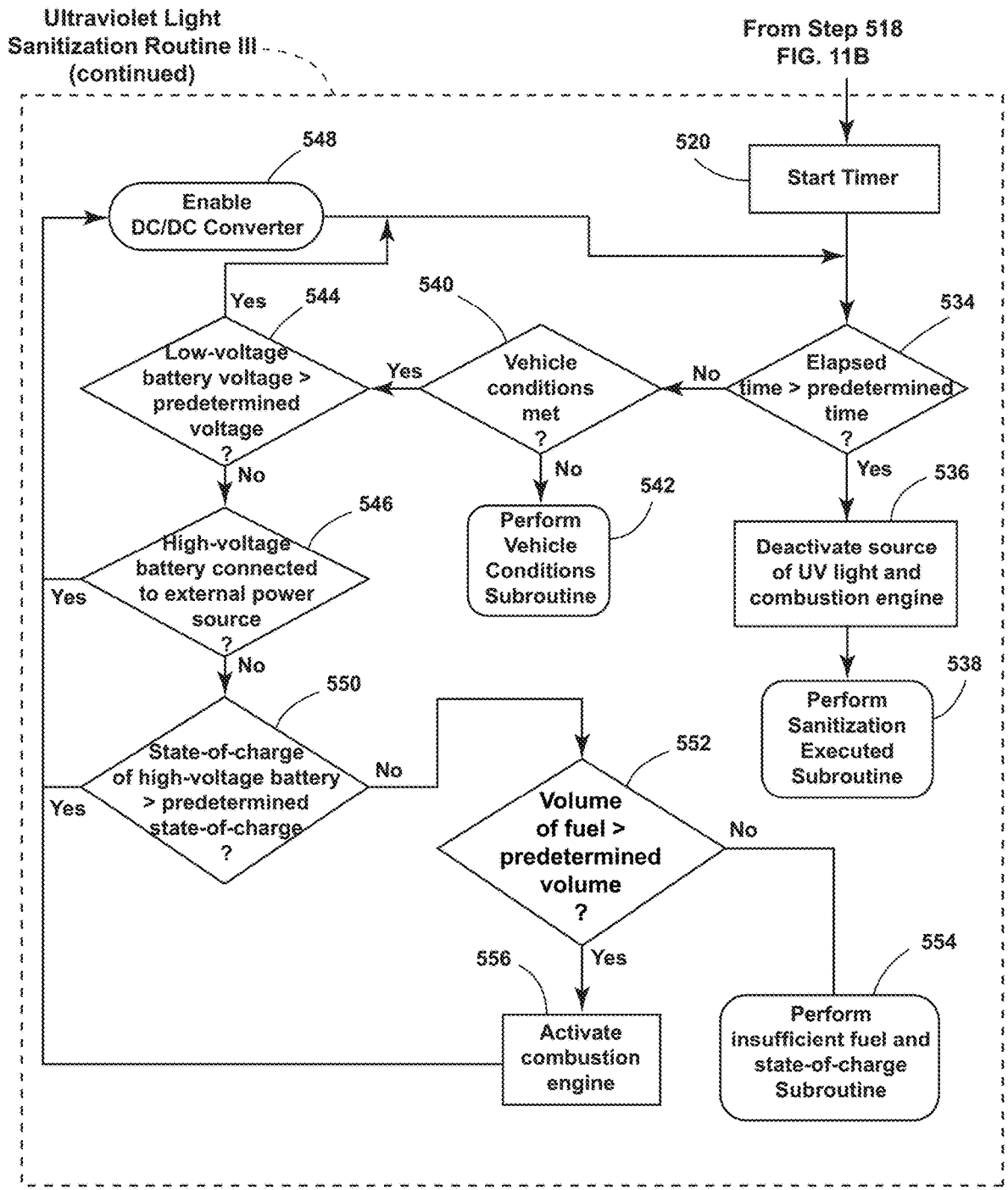

After activating the source 28 of the ultraviolet light 30 at the step 518, the method 500 proceeds to the step 520 (see FIG. 11C). At the step 520, a timer is started to measure the amount of time that the source 28 of the ultraviolet light 30 has been emitting the ultraviolet light 30. The method 500 then proceeds to a step 534, where it is determined whether the elapsed time that the source 28 of the ultraviolet light 30 has been emitting the ultraviolet light 30 is greater than a predetermined elapsed time. If it is determined that the elapsed time is greater than the predetermined elapsed time, then the method 500 continues to a step 536. At the step 536, the source 28 of the ultraviolet light 30 and the combustion engine 40, if already activated, are deactivated. The method 500 then proceeds to a step 538 where the Sanitization Executed Subroutine is performed thus ending the method 500.

If instead at the step 534, it is determined "NO", the elapsed time is not greater than the predetermined elapsed time, then the method 500 proceeds to a step 540. At the step 540, it is determined whether the vehicle 10 conditions remain satisfied. If the determination is "NO," the vehicle conditions are not satisfied, then the method 500 proceeds to a step 542. At the step 542, the source 28 of the ultraviolet light 30 and the combustion engine 40, if already activated, are deactivated and the Vehicle Conditions Subroutine is performed thus ending the method 500. If the determination is "YES," the vehicle conditions are satisfied, then the method 500 proceeds to a step 544. At the step 544, it is determined whether the voltage of the low-voltage battery 82 is above the predetermined voltage. If the determination is "YES," the voltage of the low-voltage battery 82 is above the predetermined voltage, then the method 500 proceeds back to the step 534. If the determination is "NO," the voltage of the low-voltage battery 82 is not above the predetermined voltage, then the method 500 proceeds to a step 546. At the step 546, it is determined whether the high-voltage battery 100 is connected to the external power source 114. If the determination is "YES," the high-voltage battery 100 is connected to the external power source 114, then the method 500 proceeds to a step 548. At the step 548, the DC-to-DC converter 122 is enabled, and the method 500 proceeds back to the step 534 until it is determined that the elapsed time is greater than the predetermined elapsed time. If instead at the step 546 the determination is "NO," the high-voltage battery 100 is not connected to the external power source 114, then the method 500 proceeds to a step 550. At the step 550, it is determined whether the state-of-charge of the high-voltage battery 100 is greater than the predetermined state-of-charge. If the determination is "YES," the state-of-charge of the high voltage battery is greater than the predetermined state-of-charge, then the method 500 proceeds to the step 548 described above and the high-voltage battery 100 powers the source 28 of the ultraviolet light 30. If the determination is "NO," the state-of-charge of the high-voltage battery 100 is not greater than the predetermined state-of-charge, then the method 500 proceeds to a step 552. At the step 552, it is determined whether the volume of fuel 60 in the tank 64 is greater than a predetermined volume. If it is determined "NO," that the volume of fuel 60 in the tank 64 is not greater than a predetermined volume, then the method 500 proceeds to a step 554 where the source 28 of the ultraviolet light 30 and the combustion engine 40, if already activated, are deactivated and the Insufficient Fuel and State-of-Charge Subroutine is performed and the method 500 ends. If it is determined "YES," that the volume of fuel 60 in the tank 64 is greater than the predetermined volume, then the method 500 proceeds to a step 556. At the step 556, the combustion engine 40 is activated or remains activated is previously activated. The method 500 then proceeds to the step 548, and the combustion engine 40 provides the power to operate the source 28 of the ultraviolet light 30. The steps 510-556 of the method 500 are collectively hereinafter referred to as the "Ultraviolet Light Sanitization Routine III."

Figure 11D:
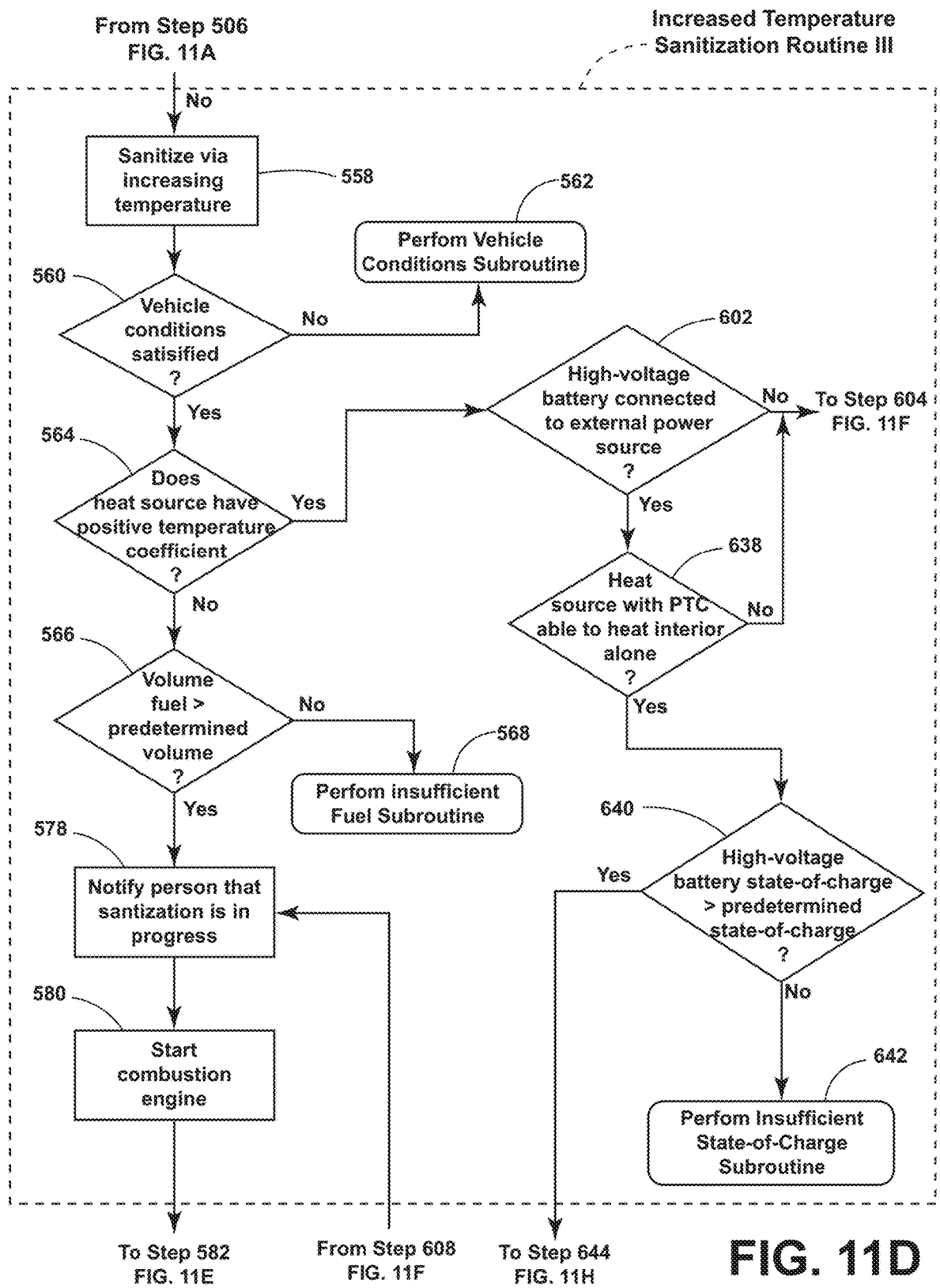
Figure 11E:
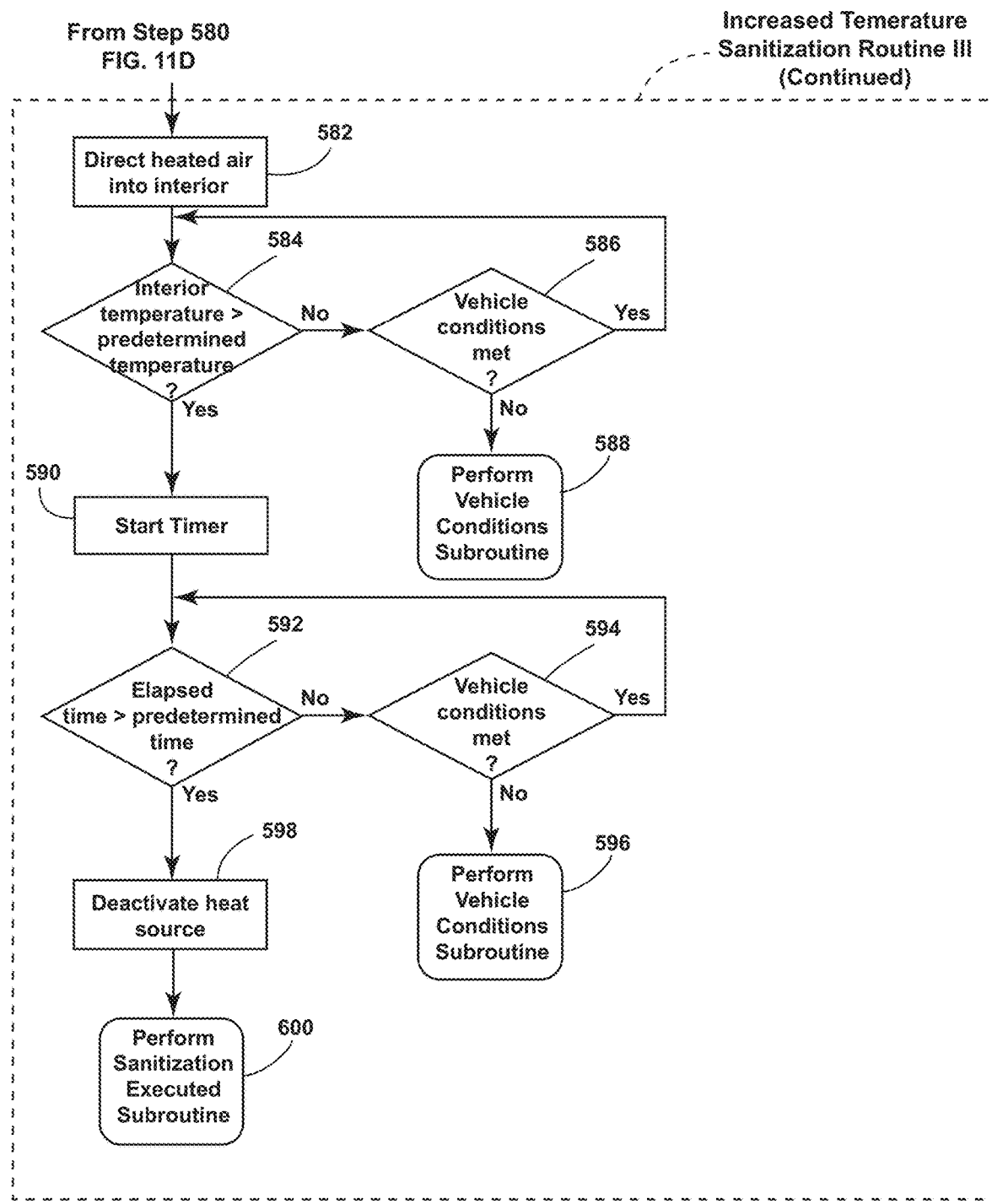
Figure 11F:
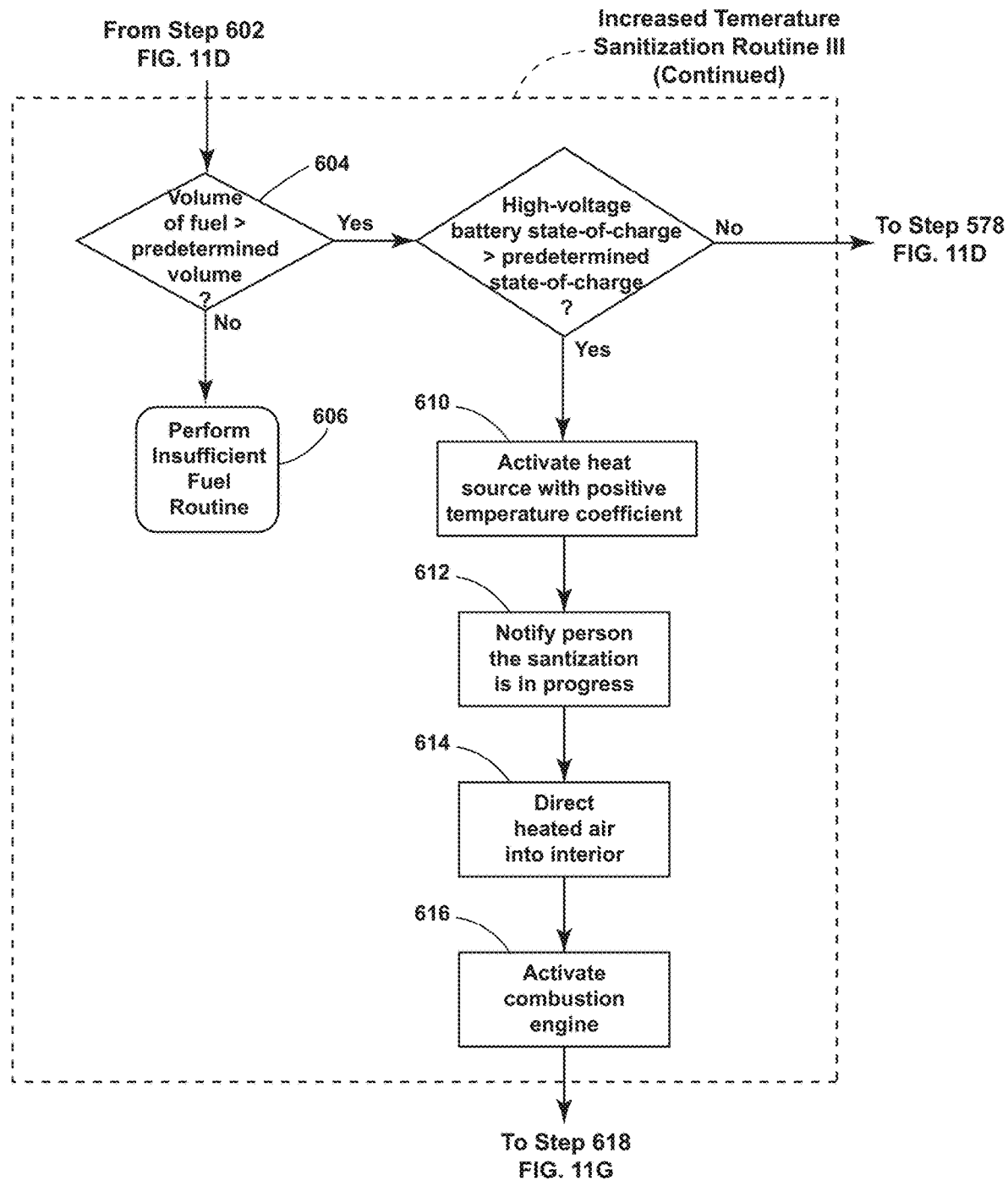
Figure 11H:
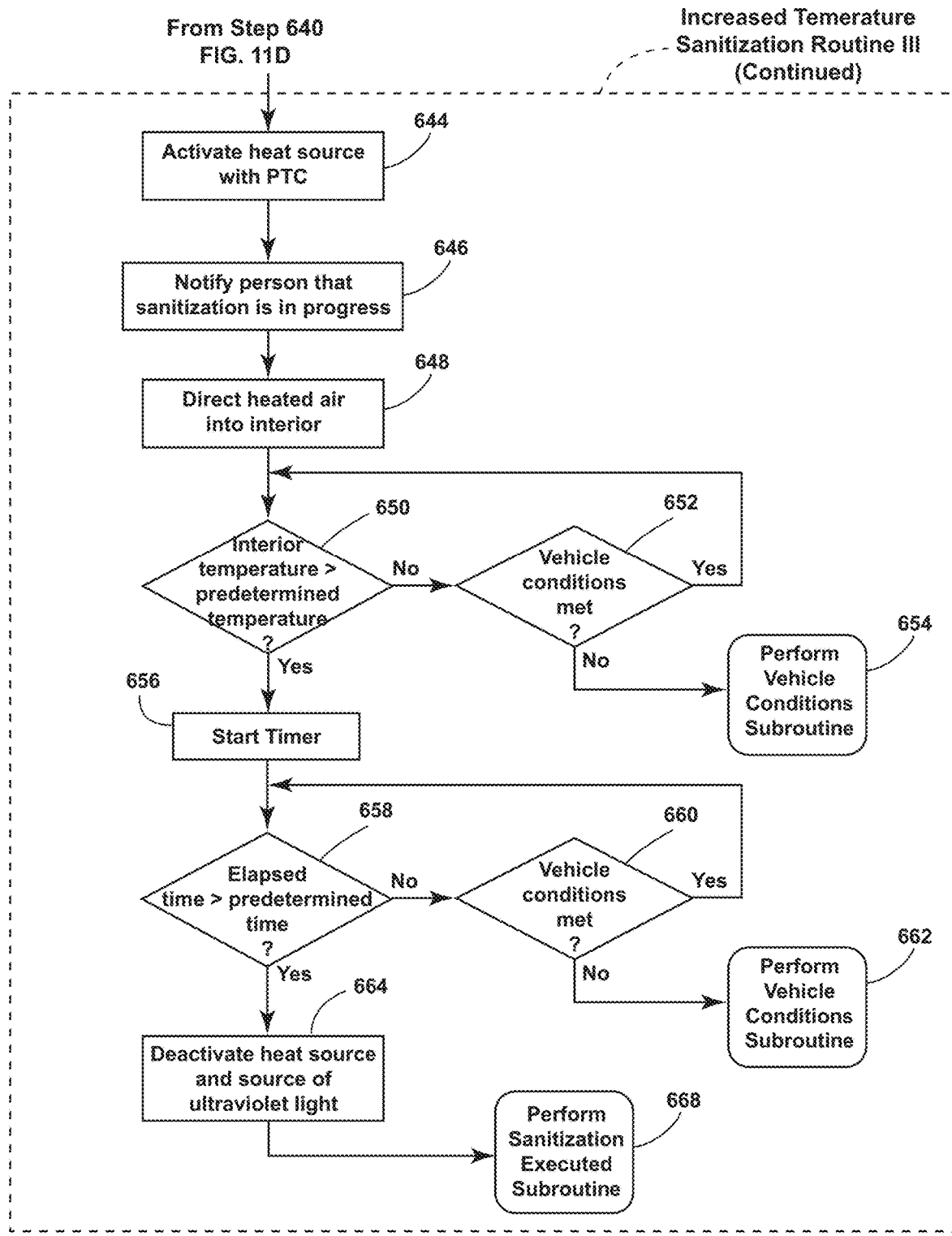

Returning now back to the step 506 (see FIG. 11A), if it is determined "NO," the temperature of the interior 12 is not above the predetermined temperature, then the method 500 proceeds to a step 558 (see FIG. 11D). At the step 558, it is determined to sanitize the interior 12 by increasing the temperature of the interior 12. The method 500 then proceeds to a step 560. At the step 560, the method 500 determines whether the vehicle 10 conditions are satisfied. If it is determined that "NO," the vehicle conditions are not satisfied, then the method 500 proceeds to a step 562 where the Vehicle Conditions Subroutine (see FIG. 9B) is performed ending the method 500. If instead it is determined that "YES," the vehicle 10 conditions are satisfied, then the method 500 proceeds to a step 564.

At the step 564, it is determined whether the heat source 20 (such as the heating element 126) has positive temperature coefficient. If it is determined that "NO," the heat source 20 does not have positive temperature coefficient, then the method 500 proceeds to a step 566. At the step 566, it is determined whether the volume of fuel 60 in the tank 64 is greater than a predetermined volume. If it is determined that "NO," the volume of fuel 60 in the tank 64 is not greater than the predetermined volume, then the method 500 proceeds to a step 568 where the Insufficient Fuel Subroutine is performed thus ending the method 500. If it is determined that "YES," the volume of fuel 60 in the tank 64 is greater than the predetermined volume, then the method 500 proceeds to a step 578. At the step 578, the person 162 is sent the communication 182 (see FIG. 6C) that sanitization is in progress. The method 500 then proceeds to a step 580. At the step 580, the combustion engine 40 to provide heat to the heat exchanger 90 as the heat source 20 to heat the air 96 is directed into the interior 12. The seat heating element(s) 128 can also be activated as part of the heat source 20. The method 500 then proceeds to a step 582 (see FIG. 11E).

At the step 582, the air 96, heated, is directed into the interior 12 via the heat exchanger 90 in thermal communication with the combustion engine 40. The method 500 then proceeds to a step 584. At the step 584, it is determined whether temperature of the interior 12 of the vehicle 10 is greater than a predetermined temperature (such as a temperature sufficient to sanitize the interior 12). If it is determined "NO," the temperature of the interior 12 is not greater than the predetermined temperature, then the method 500 proceeds to a step 586. At the step 586, it is determined whether the vehicle conditions are satisfied. If it is determined "NO," the vehicle conditions are not satisfied, then the method 500 proceeds to a step 588 where the combustion engine 30 is deactivated and the Vehicle Conditions Subroutine is performed thus ending the method 500 ends. If it is determined "YES," the vehicle 10 conditions are satisfied, then the method 500 proceeds back to the step 584 until the temperature of the interior 12 is greater than the predetermined temperature. If instead at the step 584 it is determined "YES," the temperature of the interior 12 is greater than the predetermined temperature, then the method 500 proceeds to a step 590.

At the step 590, the timer is started to measure the amount of time that the temperature of the interior 12 has been greater than the predetermined temperature. The method 500 then proceeds to a step 592, where it is determined whether the amount of time (the elapsed time) that the temperature of the interior 12 has been greater than the predetermined temperature is greater than a predetermined elapsed time. If the determination is "NO," that the amount of time is not greater than the predetermined elapsed time, then the method 500 proceeds to a step 594. At the step 594, it is determined whether the vehicle conditions remain satisfied. If the determination is "YES," the vehicle 10 conditions are satisfied, then the method 500 proceeds back to the step 592. If the determination is "NO," the vehicle conditions are not satisfied, then the method 500 proceeds to a step 596 where the combustion engine 30 is deactivated and the Vehicle Conditions Subroutine (see FIG. 9B) is performed thus ending the method 500.

If at step 592 if is determined that "YES," the amount of time is greater than the predetermined elapsed time, then the method 500 proceeds to a step 598. At the step 598, the heat source 20 is deactivated, which includes deactivating the combustion engine 40 and the seat heating element(s) 128, if previously activated, and stopping flow of air 96 into the interior 12. The method 500 then proceeds to a step 600 where the Sanitization Executed Subroutine is performed thus ending the method 500.

Referring back to FIG. 11D, if instead at step 564, it is determined that the heat source 20 has a positive temperature coefficient, then the method 500 proceeds to a step 602. At the step 602, it is determined whether the high-voltage battery 100 is connected to the external power source 114. If it is determined "NO," the high-voltage battery 100 is not connected to the external power source 114, then the method 500 proceeds to a step 604 (see FIG. 11F). At the step 604, it is determined whether the volume of the fuel 60 in the tank 64 is greater than a predetermined volume. If it is determined "NO," the volume of the fuel 60 in the tank 64 is not greater than the predetermined volume, then the method 500 proceeds to a step 606 wherein the Insufficient Fuel Subroutine is performed thus ending the method 500. If however it is determined "YES," the volume of the fuel 60 is greater than the predetermined volume, then the method 500 proceeds to a step 608. At the step 608, it is determined whether the state-of-charge of the high-voltage battery 100 is greater than a predetermined state-of-charge. If it is determined "NO," the state-of-charge of the high-voltage battery 100 is not greater than the predetermined state-of-charge, then the method 500 returns to the step 578 (see FIG. 11D). If it is determined "YES," the state-of-charge of the high-voltage battery 100 is greater than the predetermined state-of-charge, then the method 500 proceeds to a step 610.

At the step 610, the heat source 20 with the positive temperature coefficient, that is, the heating element 126 is activated (and optionally the seat heating element(s) 128). The method 500 then proceeds to a step 612. At the step, the person 162 is sent the communication 182 that sanitization is in progress (see FIG. 6C). The method 500 then proceeds to a step 614. At the step 614, the air 96 that the heating element 126 with the positive temperature coefficient heats is directed into the interior 12 of the vehicle 10, raising the temperature of the interior 12. The method 500 then proceeds to a step 616. At the step 616, the combustion engine 40 is activated. The combustion engine 40 helps generate electrical power to operate the heat source 20 and also generates heat from which the air 96 is additionally heated via the heat exchanger 90 to be directed into the interior 12. The method 500 then proceeds to a step 618 (see FIG. 11G).

At the step 618, it is determined whether the temperature of the interior 12 of the vehicle 10 is greater than a predetermined temperature (such as a temperature sufficient to sanitize the interior 12). If it is determined "NO," the temperature of the interior 12 is not greater than the predetermined temperature, then the method 500 proceeds to a step 620. At the step 620, it is determined whether the vehicle conditions are satisfied. If the determination is "NO," the vehicle conditions are not satisfied, then the method 500 proceeds to a step 622 where the heating element 126 and the combustion engine 30 are deactivated and the Vehicle Conditions Subroutine is performed thus ending the method 500. If the determination is "YES," the vehicle conditions are satisfied, then the method 500 proceeds back to step 618 until the temperature of the interior 12 is greater than the predetermined temperature.

If instead at the step 618, the determination is "YES," the temperature of the interior 12 is greater than the predetermined temperature, then the method 500 proceeds to a step 624. At the step 624, the heating element 126 with the positive temperature coefficient is deactivated. The method then proceeds to a step 626. At the step 626, the timer is started to measure the amount of time that the temperature of the interior 12 has been greater than the predetermined temperature. The method 500 then proceeds to a step 628, where it is determined whether the amount of time (the elapsed time) that the temperature of the interior 12 has been greater than the predetermined temperature is greater than a predetermined elapsed time. If the determination is "NO," that the amount of time is not greater than the predetermined elapsed time, then the method 500 proceeds to a step 630. At the step 630, it is determined whether the vehicle conditions remain satisfied. If the determination is "YES," the vehicle conditions are satisfied, then the method 500 proceeds back to the step 628. If the determination is "NO," the vehicle conditions are not satisfied, then the method 500 proceeds to a step 632 where the heat source 20 is deactivated the Vehicle Conditions Subroutine is performed thus ending the method 500.

If at the step 628 if is determined that "YES," the amount of time is greater than the predetermined elapsed time, then the method 500 proceeds to a step 634. At the step 634, the heat source 20 is deactivated, which includes deactivating the combustion engine 40 and stopping flow of the air 96 into the interior 12. The method 500 then proceeds to a step 636 where the Sanitization Executed Subroutine is performed thus ending the method 500.

Referring back to the step 602 at FIG. 11D, if is determined that "YES," the high-voltage battery 100 is connected to the external power source 114, then the method 500 proceeds to a step 638. At the step 638, it is determined whether the heating element 126 (the heat source 20 with the positive temperature coefficient) is able to heat the interior 12 without the assistance of the combustion engine 40 also producing heat that is transferred to the interior 12. In embodiments, whether the heating element 126 with the positive temperature coefficient is so able is predetermined. If it is determined "NO," the heating element 126 with the positive temperature coefficient is unable to heat the interior 12 without the assistance of the combustion engine 40 also producing heat that is transferred to the interior 12, then the method 500 proceeds to the step 604 (see FIG. 11F).

However, it is determined "YES," the heating element 126 with the positive temperature coefficient is able to heat the interior 12 without the assistance of the combustion engine 40 also producing heat that is transferred to the interior 12, then the method 500 proceeds to a step 640. At the step 640, it is determined whether the state-of-charge of the high-voltage battery 100 is greater than a predetermined state-of-charge. If it is determined "NO," the state-of-charge of the high-voltage battery 100 is not greater than the predetermined state-of-charge, then the method 500 proceeds to a step 642 where the Insufficient State-of-Charge Subroutine is performed thus ending the method 500. If it is determined "YES," the state-of-charge of the high-voltage battery 100 is greater than the predetermined state-of-charge, then the method 500 proceeds to a step 644 (see FIG. 11H).

At the step 644, the heating element 126 with the positive temperature coefficient is activated. The method 500 then proceeds to a step 646. At the step 646, the communication 182 is sent to the person 162 at the remote user interface 148 that the sanitization is in progress (see FIG. 6C). The method 500 then proceeds to a step 648 where the heating element 126 heats the air 96 that is directed into the interior 12 (without additional heat from the combustion engine 40). The seat heating element(s) 128 may also be activated. The method 500 then proceeds to a step 650. At the step 650, it is determined whether the temperature of the interior 12 is greater than a predetermined temperature. If the determination is "NO," the temperature of the interior 12 is not greater than the predetermined temperature, then the method 500 proceeds to a step 652. At the step 652, it is determined whether the vehicle conditions are satisfied. If it is determined "YES," the vehicle conditions are satisfied, then the method 500 returns to the step 650. If it is determined "NO," the vehicle conditions are not satisfied, then the method 500 proceeds to a step 654 where the Vehicle Conditions Subroutine is performed thus ending the method 500. If instead at the step 650 it is determined "YES," the temperature of the interior 12 is greater than the predetermined temperature, then the method 500 proceeds to a step 656.

At the step 656, the timer is started to measure the amount of time that the temperature of the interior 12 has been greater than the predetermined temperature. The method 500 then proceeds to a step 658, where it is determined whether the amount of time (the elapsed time) that the temperature of the interior 12 has been greater than the predetermined temperature is greater than a predetermined elapsed time. If the determination is "NO," that the amount of time is not greater than the predetermined elapsed time, then the method 500 proceeds to a step 660. At the step 660, it is determined whether the vehicle conditions remain satisfied. If the determination is "NO," the vehicle conditions are not satisfied, then the method 500 proceeds to a step 662 where the Vehicle Conditions Subroutine is performed thus ending the method 500. If the determination is "YES," the vehicle conditions are satisfied, then the method 500 proceeds back to the step 658. If at the step 658 if is determined that "YES," the amount of time is greater than the predetermined elapsed time, then the method 500 proceeds to a step 664. At the step 664, the heat source 20 is deactivated, which includes deactivating heating element 126 and the seat heating element(s) 128 if activated. The method 500 then proceeds to a step 668, to perform the Sanitization Executed Subroutine thus ending the method 500. The steps 560-668 are collectively hereinafter referred to as the "Increased Temperature Sanitization Routine III."

Referring back to FIG. 11A, if instead at the step 504 it is determined that the person 162 did specify the type of sanitization, then if the person 162 chose sanitization via emission of the ultraviolet light 30, then the method 500 proceeds to perform the Ultraviolet Light Sanitization Routine III described above and then the method 500 ends. If the person 162 chose sanitization via increasing the temperature of the interior 12, then the method 500 proceeds to perform the Increased Temperature Sanitization Routine III described above and then the method 500 ends.

If the person 162 chose sanitization via both emission of the ultraviolet light 30 and increasing the temperature of the interior 12, then the method 500 proceeds to perform the Increased Temperature Sanitization Routine III described above and then the method 500 ends, with the exception that (i) after the step 584 where it is determined "YES," the temperature of the interior 12 is greater than the predetermined temperature, and before step 590 where the timer is started, a step 670 is performed where the source 28 of the ultraviolet light 30 is activated, (ii) after the step 618 where it is determined "YES," the temperature of the interior 12 is greater than the predetermined temperature, and before step 626 where the timer is started, a step 672 is performed where the source 28 of the ultraviolet light 30 is activated, and (iii) after the step 650 where it is determined "YES," the temperature of the interior 12 is greater than the predetermined temperature, and before step 656 where the timer is started, a step 674 is performed where the source 28 of the ultraviolet light 30 is activated.

In any of the methods 300, 400, 500 described above, the person 162 could have specified that the sanitization via the ultraviolet light 30 was to occur only at one or more of the first zone 34, the second zone 36, or the third zone 38. For example, the person 162 could have selected at the remote user interface 148 that sanitization via the ultraviolet light 30 shall occur at the first zone 34. The controller 146 then activates only the source 28a to emit the ultraviolet light into the first zone 34, while leaving the sources 28b, 28c deactivated so the ultraviolet light 30 would not be emitted therefrom into the second zone 36 and the third zone 38.

Because the vehicle 10 and methods described allow the person 162 to achieve sanitization of the interior 12 of the vehicle 10 via the remote user interface 148, the person 162 does not need to actually enter the interior 12 of the vehicle 10 while the vehicle 10 is a not-sanitized state in order to sanitize the interior 12. The person 162 is informed that the vehicle 10 has sanitized itself.

It is to be understood that variations and modifications can be made on the aforementioned structure without departing from the concepts of the present invention, and further it is to be understood that such concepts are intended to be covered by the following claims unless these claims by their language expressly state otherwise.

What is claimed is:

1. A vehicle comprising: an interior; a source of ultraviolet light disposed to emit the ultraviolet light into the interior; a heat source, separate from the source of the ultraviolet light, in thermal communication with the interior; a combustion engine that combusts fuel to propel the vehicle, a battery in electrical communication with the source of the ultraviolet light, the battery having a voltage; and a controller in communication with the heat source, the battery, and the source of the ultraviolet light, wherein, the controller is configured to cause, upon receiving a command from a remote user interface to sanitize the interior, (i) the heat source to increase a temperature of the interior and (ii) the source of the ultraviolet light to emit the ultraviolet light into the interior; and upon receiving the command from the remote user interface, and the voltage of the battery is below a predetermined voltage, the controller is further configured to start the combustion engine to increase the voltage of the battery to the predetermined voltage before causing the source of the ultraviolet light to emit the ultraviolet light into the interior.

2. The vehicle of claim 1 further comprising: wherein, the vehicle does not further include an electric motor configured to propel the vehicle.

3. The vehicle of claim 1 further comprising: a fuel tank that contains the fuel, the fuel tank in fluid communication with the combustion engine; and a volume sensor configured to produce a signal from which a volume of the fuel within the fuel tank can be calculated or estimated, the volume sensor in communication with the controller; wherein, the controller, as a function of the signal from the volume sensor, is configured to determine that the volume of the fuel is above a predetermined volume before starting the combustion engine to increase the voltage of the battery.

4. The vehicle of claim 3, wherein
the heat source is a heat exchanger in thermal communication with the combustion engine and the interior of the vehicle;
the controller, as a function of the signal from the volume sensor, is configured to determine that the volume of the fuel is above a second predetermined volume before starting the combustion engine to increase the temperature of the interior via the heat exchanger; and
the second predetermined volume is greater than the predetermined volume.

5. The vehicle of claim 1 further comprising: a temperature sensor configured to produce a signal from which the temperature of the interior of the vehicle can be determined, the temperature sensor in communication with the controller, wherein, the heat source is a heat exchanger in thermal communication with the combustion engine and the interior of the vehicle; and wherein, the controller, as a function of the signal from the temperature sensor, is configured to determine that the temperature of the interior of the vehicle is less than a predetermined temperature before starting the combustion engine to increase the temperature of the interior via the heat exchanger.

6. The vehicle of claim 1 further comprising: an electric motor configured to propel the vehicle; wherein, the heat source has a positive temperature coefficient.

7. The vehicle of claim 1, wherein after the controller causes (i) the heat source to increase the temperature of the interior and (ii) the source of the ultraviolet light to emit the ultraviolet light into the interior, the controller is configured to cause a communication to the remote user interface that the command has been executed.

8. The vehicle of claim 1, wherein after the controller causes (i) the heat source to increase the temperature of the interior and (ii) the source of the ultraviolet light to emit the ultraviolet light into the interior, the controller causes the vehicle to send a communication that is sensible from an external environment that the command has been executed.

9. The vehicle of claim 1 further comprising:
an occupancy sensor configured to produce a signal from which an occupancy of the vehicle can be determined, the sensor in communication with the controller;
wherein, the controller, as a function of the signal from the occupancy sensor, determines that no occupant occupies the interior of the vehicle before causing the source of the ultraviolet light to emit the ultraviolet light into the interior.

10. A vehicle comprising: an interior; a source of ultraviolet light disposed to emit the ultraviolet light into the interior;
a heat source, separate from the source of the ultraviolet light, in thermal communication with the interior; a battery in electrical communication with the heat source and configured to be connected to an external power source that is external to the vehicle, the battery having a state-of-charge; an electric motor configured to propel the vehicle; and a controller in communication with the heat source, the battery, and the source of the ultraviolet light, wherein, the controller is configured to cause, upon receiving a command from a remote user interface to sanitize the interior, (i) the heat source to increase a temperature of the interior and (ii) the source of the ultraviolet light to emit the ultraviolet light into the interior; and wherein, upon receiving the command from the remote user interface to sanitize the interior, the controller is configured to determine (i) that the state-of-charge of the battery is less than a predetermined state-of-charge and (ii) that the battery is connected to the external power source, before causing the heat source to increase the temperature of the interior of the vehicle.

11. The vehicle of claim 10 further comprising:
a second battery in electrical communication with the source of the ultraviolet light and in communication with the controller, the second battery having a voltage; wherein, upon receiving the command from the remote user interface, the controller is further configured to determine that the voltage of the second battery is above a predetermined voltage before causing the source of the ultraviolet light to emit the ultraviolet light into the interior.

12. The vehicle of claim 11, wherein: the second battery has a state-of-charge; and upon receiving the command from the user interface, the controller is further configured to determine that the state-of-charge of the second battery is above a predetermined state-of-charge before causing the source of the ultraviolet light to emit the ultraviolet light into the interior.

13. The vehicle of claim 11, wherein the second battery has a state-of-charge;
the second battery is connected to the external power source; and upon receiving the command from the user interface, the controller is further configured to determine that the state-of-charge of the second battery is below a predetermined state-of-charge but additionally determines that the second battery is connected to the external power source before causing the source of the ultraviolet light to emit the ultraviolet light into the interior.

14. The vehicle of claim 10, wherein the vehicle does not further include a combustion engine configured to propel the vehicle.

15. The vehicle of claim 10, wherein the heat source has a positive temperature coefficient.

16. A vehicle comprising: an interior; a source of ultraviolet light disposed to emit the ultraviolet light into the interior; a combustion engine that combusts fuel to propel the vehicle; a fuel tank that contains the fuel, the fuel tank in fluid communication with the combustion engine; a volume sensor configured to produce a signal from which a volume of the fuel can be calculated or estimated, the volume sensor in communication with the controller; a heat exchanger in thermal communication with the combustion engine and the interior of the vehicle; and
a controller in communication with the heat exchanger, the source of the ultraviolet light, the combustion engine, and the volume sensor; wherein, the controller is configured to cause, upon receiving a command to sanitize the interior from a remote user interface, (i) the heat exchanger to increase a temperature of the interior and (ii) the source of the ultraviolet light to emit the ultraviolet light into the interior; and wherein, the controller, as a function of the signal from the volume sensor, is configured to determine that the volume of the fuel is above a predetermined volume before starting the combustion engine to increase the temperature of the interior via the heat exchanger.

* * * * *